(12) United States Patent
Rebollo Garcia et al.

(10) Patent No.: US 10,508,310 B2
(45) Date of Patent: Dec. 17, 2019

(54) METHOD OF PREDICTING A RESPONSE TO AN ANTI-TUMOR TREATMENT

(71) Applicants: SORBONNE UNIVERSITE, Paris (FR); INSTITUT CURIE, Paris (FR)

(72) Inventors: Angelita Rebollo Garcia, Paris (FR); Fariba Nemati, Paris (FR); Didier Decaudin, Verrieres le Buisson (FR)

(73) Assignees: SORBONNE UNIVERSITE, Paris (FR); INSTITUT CURIE, Paris (FR)

( * ) Notice: Subject to any disclaimer, the term of this patent is extended or adjusted under 35 U.S.C. 154(b) by 458 days.

(21) Appl. No.: 15/102,539

(22) PCT Filed: Dec. 9, 2014

(86) PCT No.: PCT/EP2014/077024
§ 371 (c)(1),
(2) Date: Jun. 8, 2016

(87) PCT Pub. No.: WO2015/086583
PCT Pub. Date: Jun. 18, 2015

(65) Prior Publication Data
US 2016/0312293 A1    Oct. 27, 2016

(30) Foreign Application Priority Data

Dec. 9, 2013 (EP) .................................. 13306688

(51) Int. Cl.
| | | |
|---|---|---|
| *C12Q 1/68* | (2018.01) | |
| *C12Q 1/6886* | (2018.01) | |
| *A61K 38/17* | (2006.01) | |
| *A61K 38/48* | (2006.01) | |
| *A61K 39/00* | (2006.01) | |

(52) U.S. Cl.
CPC ........ *C12Q 1/6886* (2013.01); *A61K 38/1709* (2013.01); *A61K 38/4873* (2013.01); *C12Y 304/22* (2013.01); *C12Q 2600/106* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

2008/0076134 A1    3/2008    Muraca

FOREIGN PATENT DOCUMENTS

| CA | 2 767 659 | 1/2011 |
|---|---|---|
| WO | WO 2011/084108 | 7/2011 |
| WO | WO 2012/042038 | 4/2012 |
| WO | WO 2012/052758 | 4/2012 |
| WO | WO 2013/050331 | 4/2013 |
| WO | WO 2013/098339 | 7/2013 |

OTHER PUBLICATIONS

Written Opinion in International Application No. PCT/EP2014/077024, Apr. 2, 2015, pp. 1-4.
Database NCBI [Online] Accession No. GPL96, "Affymetrix GeneChip Human Genome U133 Array Set HG-U133A" Mar. 11, 2002, pp. 1-511, XP-002355386.

*Primary Examiner* — James Martinell
(74) *Attorney, Agent, or Firm* — Saliwanchik, Lloyd & Eisenschenk

(57) ABSTRACT

The invention provides an in vitro method for determining the likelihood for a patient affected with a tumor to respond to a treatment with a pro-apoptotic peptide able to disrupt interaction between caspase 9 and PP2A, which method comprises determining expression level of at least each of VIM, MK167, TCF7L2, NEK2, BIRC5, MCL1, and PLK1 genes, in a biological sample of said patient.

4 Claims, No Drawings
Specification includes a Sequence Listing.

SEQUENCE LISTING

<160> NUMBER OF SEQ ID NOS: 78

<210> SEQ ID NO 1
<211> LENGTH: 18
<212> TYPE: PRT
<213> ORGANISM: Homo sapiens

<400> SEQUENCE: 1

Tyr Val Glu Thr Leu Asp Gly Ile Phe Glu Gln Trp Ala His Ser Glu
1               5                   10                  15

Asp Leu

<210> SEQ ID NO 2

```
<211> LENGTH: 20
<212> TYPE: PRT
<213> ORGANISM: Homo sapiens

<400> SEQUENCE: 2

Asp Thr Leu Asp His Ile Arg Ala Leu Asp Arg Leu Gln Glu Val Pro
1               5                   10                  15

His Glu Gly Pro
            20

<210> SEQ ID NO 3
<211> LENGTH: 16
<212> TYPE: PRT
<213> ORGANISM: Artificial Sequence
<220> FEATURE:
<223> OTHER INFORMATION: proapoptotic peptide
<220> FEATURE:
<221> NAME/KEY: SITE
<222> LOCATION: (2)..(2)
<223> OTHER INFORMATION: Xaa can be any naturally occurring amino acid
<220> FEATURE:
<221> NAME/KEY: SITE
<222> LOCATION: (7)..(7)
<223> OTHER INFORMATION: Xaa can be any naturally occurring amino acid
<220> FEATURE:
<221> NAME/KEY: SITE
<222> LOCATION: (9)..(9)
<223> OTHER INFORMATION: Xaa can be any naturally occurring amino acid
<220> FEATURE:
<221> NAME/KEY: SITE
<222> LOCATION: (14)..(14)
<223> OTHER INFORMATION: Xaa can be any naturally occurring amino acid
<220> FEATURE:
<221> NAME/KEY: SITE
<222> LOCATION: (16)..(16)
<223> OTHER INFORMATION: Xaa can be any naturally occurring amino acid

<400> SEQUENCE: 3

Tyr Xaa Glu Thr Leu Asp Xaa Ile Xaa Glu Gln Trp Ala Xaa Ser Xaa
1               5                   10                  15

<210> SEQ ID NO 4
<211> LENGTH: 18
<212> TYPE: PRT
<213> ORGANISM: Homo sapiens

<400> SEQUENCE: 4

Tyr Val Glu Thr Leu Asp Asp Ile Phe Glu Gln Trp Ala His Ser Glu
1               5                   10                  15

Asp Leu

<210> SEQ ID NO 5
<211> LENGTH: 20
<212> TYPE: PRT
<213> ORGANISM: Homo sapiens

<400> SEQUENCE: 5

Asp Thr Leu Asp His Ile Arg Ala Leu Asp Arg Leu Gln Glu Val Pro
1               5                   10                  15

His Glu Gly Pro
            20

<210> SEQ ID NO 6
<211> LENGTH: 19
<212> TYPE: PRT
<213> ORGANISM: Homo sapiens

<400> SEQUENCE: 6
```

```
Thr Leu Asp His Ile Arg Ala Leu Asp Arg Leu Gln Glu Val Pro His
 1               5                  10                  15

Glu Gly Pro

<210> SEQ ID NO 7
<211> LENGTH: 18
<212> TYPE: PRT
<213> ORGANISM: Homo sapiens

<400> SEQUENCE: 7

Leu Asp His Ile Arg Ala Leu Asp Arg Leu Gln Glu Val Pro His Glu
 1               5                  10                  15

Gly Pro

<210> SEQ ID NO 8
<211> LENGTH: 17
<212> TYPE: PRT
<213> ORGANISM: Homo sapiens

<400> SEQUENCE: 8

Asp His Ile Arg Ala Leu Asp Arg Leu Gln Glu Val Pro His Glu Gly
 1               5                  10                  15

Pro

<210> SEQ ID NO 9
<211> LENGTH: 16
<212> TYPE: PRT
<213> ORGANISM: Homo sapiens

<400> SEQUENCE: 9

His Ile Arg Ala Leu Asp Arg Leu Gln Glu Val Pro His Glu Gly Pro
 1               5                  10                  15

<210> SEQ ID NO 10
<211> LENGTH: 19
<212> TYPE: PRT
<213> ORGANISM: Homo sapiens

<400> SEQUENCE: 10

Asp Thr Leu Asp His Ile Arg Ala Leu Asp Arg Leu Gln Glu Val Pro
 1               5                  10                  15

His Glu Gly

<210> SEQ ID NO 11
<211> LENGTH: 18
<212> TYPE: PRT
<213> ORGANISM: Homo sapiens

<400> SEQUENCE: 11

Asp Thr Leu Asp His Ile Arg Ala Leu Asp Arg Leu Gln Glu Val Pro
 1               5                  10                  15

His Glu

<210> SEQ ID NO 12
<211> LENGTH: 17
<212> TYPE: PRT
<213> ORGANISM: Homo sapiens

<400> SEQUENCE: 12

Asp Thr Leu Asp His Ile Arg Ala Leu Asp Arg Leu Gln Glu Val Pro
 1               5                  10                  15
```

His

<210> SEQ ID NO 13
<211> LENGTH: 16
<212> TYPE: PRT
<213> ORGANISM: Homo sapiens

<400> SEQUENCE: 13

Asp Thr Leu Asp His Ile Arg Ala Leu Asp Arg Leu Gln Glu Val Pro
1               5                   10                  15

<210> SEQ ID NO 14
<211> LENGTH: 18
<212> TYPE: PRT
<213> ORGANISM: Homo sapiens

<400> SEQUENCE: 14

Thr Leu Asp His Ile Arg Ala Leu Asp Arg Leu Gln Glu Val Pro His
1               5                   10                  15

Glu Gly

<210> SEQ ID NO 15
<211> LENGTH: 16
<212> TYPE: PRT
<213> ORGANISM: Homo sapiens

<400> SEQUENCE: 15

Leu Asp His Ile Arg Ala Leu Asp Arg Leu Gln Glu Val Pro His Glu
1               5                   10                  15

<210> SEQ ID NO 16
<211> LENGTH: 17
<212> TYPE: PRT
<213> ORGANISM: Homo sapiens

<400> SEQUENCE: 16

Thr Leu Asp His Ile Arg Ala Leu Asp Arg Leu Gln Glu Val Pro His
1               5                   10                  15

Glu

<210> SEQ ID NO 17
<211> LENGTH: 17
<212> TYPE: PRT
<213> ORGANISM: Homo sapiens

<400> SEQUENCE: 17

Leu Asp His Ile Arg Ala Leu Asp Arg Leu Gln Glu Val Pro His Glu
1               5                   10                  15

Gly

<210> SEQ ID NO 18
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: SITE
<222> LOCATION: (1)..(1)
<223> OTHER INFORMATION: Xaa can be any naturally occurring amino acid
<220> FEATURE:
<221> NAME/KEY: SITE
<222> LOCATION: (7)..(7)
<223> OTHER INFORMATION: Xaa can be any naturally occurring amino acid

```
<220> FEATURE:
<221> NAME/KEY: SITE
<222> LOCATION: (10)..(11)
<223> OTHER INFORMATION: Xaa can be any naturally occurring amino acid

<400> SEQUENCE: 18

Xaa Lys Lys Lys Ile Lys Xaa Glu Ile Xaa Xaa
1               5                   10

<210> SEQ ID NO 19
<211> LENGTH: 18
<212> TYPE: PRT
<213> ORGANISM: Artificial Sequence
<220> FEATURE:
<223> OTHER INFORMATION: cell penetrating peptide

<400> SEQUENCE: 19

Arg Gln Lys Arg Leu Ile Arg Gln Lys Arg Leu Ile Arg Gln Lys Arg
1               5                   10                  15

Leu Ile

<210> SEQ ID NO 20
<211> LENGTH: 18
<212> TYPE: PRT
<213> ORGANISM: Artificial Sequence
<220> FEATURE:
<223> OTHER INFORMATION: cell penetrating peptide

<400> SEQUENCE: 20

Arg His Ser Arg Ile Gly Arg His Ser Arg Ile Gly Arg His Ser Arg
1               5                   10                  15

Ile Gly

<210> SEQ ID NO 21
<211> LENGTH: 16
<212> TYPE: PRT
<213> ORGANISM: Artificial Sequence
<220> FEATURE:
<223> OTHER INFORMATION: cell penetrating peptide

<400> SEQUENCE: 21

Arg His Ser Arg Ile Gly Ile Ile Gln Gln Arg Arg Thr Arg Asn Gly
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: cell penetrating peptide

<400> SEQUENCE: 22

Arg His Ser Arg Ile Gly Val Thr Arg Gln Arg Arg Ala Arg Asn Gly
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: cell penetrating peptide

<400> SEQUENCE: 23

Arg Arg Arg Arg Arg Arg Arg Ser Arg Gly Arg Arg Thr Tyr
1               5                   10                  15
```

```
<210> SEQ ID NO 24
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: SITE
<222> LOCATION: (1)..(1)
<223> OTHER INFORMATION: Xaa can be any naturally occurring amino acid
<220> FEATURE:
<221> NAME/KEY: SITE
<222> LOCATION: (7)..(7)
<223> OTHER INFORMATION: Xaa can be any naturally occurring amino acid
<220> FEATURE:
<221> NAME/KEY: SITE
<222> LOCATION: (10)..(10)
<223> OTHER INFORMATION: Xaa can be any naturally occurring amino acid

<400> SEQUENCE: 24

Xaa Lys Lys Lys Ile Lys Xaa Glu Ile Xaa
 1               5                  10

<210> SEQ ID NO 25
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: SITE
<222> LOCATION: (8)..(8)
<223> OTHER INFORMATION: Xaa can be any naturally occurring amino acid

<400> SEQUENCE: 25

Val Lys Lys Lys Lys Ile Lys Xaa Glu Ile Lys Ile
 1               5                  10

<210> SEQ ID NO 26
<211> LENGTH: 12
<212> TYPE: PRT
<213> ORGANISM: Artificial Sequence
<220> FEATURE:
<223> OTHER INFORMATION: cell penetrating peptide

<400> SEQUENCE: 26

Val Lys Lys Lys Lys Ile Lys Arg Glu Ile Lys Ile
 1               5                  10

<210> SEQ ID NO 27
<211> LENGTH: 12
<212> TYPE: PRT
<213> ORGANISM: Artificial Sequence
<220> FEATURE:
<223> OTHER INFORMATION: cell penetrating peptide

<400> SEQUENCE: 27

Val Lys Lys Lys Lys Ile Lys Ala Glu Ile Lys Ile
 1               5                  10

<210> SEQ ID NO 28
<211> LENGTH: 12
<212> TYPE: PRT
<213> ORGANISM: Artificial Sequence
<220> FEATURE:
<223> OTHER INFORMATION: cell penetrating peptide

<400> SEQUENCE: 28

Val Lys Lys Lys Lys Ile Lys Lys Glu Ile Lys Ile
```

<210> SEQ ID NO 29
<211> LENGTH: 12
<212> TYPE: PRT
<213> ORGANISM: Artificial Sequence
<220> FEATURE:
<223> OTHER INFORMATION: cell penetrating peptide

<400> SEQUENCE: 29

```
Val Lys Lys Lys Lys Ile Lys Asn Glu Ile Lys Ile
1               5                   10
```

<210> SEQ ID NO 30
<211> LENGTH: 9
<212> TYPE: PRT
<213> ORGANISM: Artificial Sequence
<220> FEATURE:
<223> OTHER INFORMATION: cell penetrating peptide

<400> SEQUENCE: 30

```
Arg Lys Lys Arg Arg Gln Arg Arg Arg
1               5
```

<210> SEQ ID NO 31
<211> LENGTH: 11
<212> TYPE: PRT
<213> ORGANISM: Artificial Sequence
<220> FEATURE:
<223> OTHER INFORMATION: cell penetrating peptide

<400> SEQUENCE: 31

```
Tyr Gly Arg Lys Lys Arg Arg Gln Arg Arg Arg
1               5                   10
```

<210> SEQ ID NO 32
<211> LENGTH: 9
<212> TYPE: PRT
<213> ORGANISM: Artificial Sequence
<220> FEATURE:
<223> OTHER INFORMATION: cell penetrating peptide

<400> SEQUENCE: 32

```
Arg Arg Arg Arg Arg Arg Arg Arg Arg
1               5
```

<210> SEQ ID NO 33
<211> LENGTH: 11
<212> TYPE: PRT
<213> ORGANISM: Artificial Sequence
<220> FEATURE:
<223> OTHER INFORMATION: cell penetrating peptide

<400> SEQUENCE: 33

```
Arg Arg Arg Arg Arg Arg Arg Arg Arg Arg Arg
1               5                   10
```

<210> SEQ ID NO 34
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 34

```
Gly Leu Phe Glu Ala Ile Glu Gly Phe Ile Glu Asn Gly Trp Glu Gly
1               5                   10                  15
```

Met Ile Asp Gly Trp Tyr Gly Arg Arg Arg Arg Arg Arg Arg
            20                  25                  30

<210> SEQ ID NO 35
<211> LENGTH: 16
<212> TYPE: PRT
<213> ORGANISM: Artificial Sequence
<220> FEATURE:
<223> OTHER INFORMATION: cell penetrating peptide

<400> SEQUENCE: 35

Arg Gln Ile Lys Ile Trp Phe Gln Asn Arg Arg Met Lys Trp Lys Lys
1               5                   10                  15

<210> SEQ ID NO 36
<211> LENGTH: 27
<212> TYPE: PRT
<213> ORGANISM: Artificial Sequence
<220> FEATURE:
<223> OTHER INFORMATION: cell penetrating peptide

<400> SEQUENCE: 36

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 37
<211> LENGTH: 33
<212> TYPE: PRT
<213> ORGANISM: Artificial Sequence
<220> FEATURE:
<223> OTHER INFORMATION: cell penetrating peptide

<400> SEQUENCE: 37

Gly Asp Cys Leu Pro His Leu Lys Leu Cys Lys Glu Asn Lys Asp Cys
1               5                   10                  15

Cys Ser Lys Lys Cys Lys Arg Arg Gly Thr Asn Ile Glu Lys Arg Cys
            20                  25                  30

Arg

<210> SEQ ID NO 38
<211> LENGTH: 10
<212> TYPE: PRT
<213> ORGANISM: Artificial Sequence
<220> FEATURE:
<223> OTHER INFORMATION: cell penetrating peptide

<400> SEQUENCE: 38

Lys Lys Lys Lys Lys Lys Lys Lys Lys Lys
1               5                   10

<210> SEQ ID NO 39
<211> LENGTH: 11
<212> TYPE: PRT
<213> ORGANISM: Artificial Sequence
<220> FEATURE:
<223> OTHER INFORMATION: cell penetrating peptide

<400> SEQUENCE: 39

Tyr Ala Arg Ala Ala Ala Arg Gln Ala Arg Ala
1               5                   10

<210> SEQ ID NO 40

```
<211> LENGTH: 12
<212> TYPE: PRT
<213> ORGANISM: Artificial Sequence
<220> FEATURE:
<223> OTHER INFORMATION: cell penetrating peptide

<400> SEQUENCE: 40

Pro Leu Ser Ser Ile Phe Ser Arg Ile Gly Asp Pro
1               5                   10

<210> SEQ ID NO 41
<211> LENGTH: 28
<212> TYPE: PRT
<213> ORGANISM: Artificial Sequence
<220> FEATURE:
<223> OTHER INFORMATION: cell penetrating peptide

<400> SEQUENCE: 41

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 42
<211> LENGTH: 35
<212> TYPE: DNA
<213> ORGANISM: Artificial Sequence
<220> FEATURE:
<223> OTHER INFORMATION: cell penetrating peptide

<400> SEQUENCE: 42
gggarkkaak aarkkaakaa rkkaakaark kaaka                          35

<210> SEQ ID NO 43
<211> LENGTH: 19
<212> TYPE: PRT
<213> ORGANISM: Artificial Sequence
<220> FEATURE:
<223> OTHER INFORMATION: cell penetrating peptide

<400> SEQUENCE: 43

Leu Leu Ile Ile Leu Arg Arg Arg Arg Ile Arg Lys Gln Ala His Ala
1               5                   10                  15

His Ser Lys

<210> SEQ ID NO 44
<211> LENGTH: 23
<212> TYPE: PRT
<213> ORGANISM: Artificial Sequence
<220> FEATURE:
<223> OTHER INFORMATION: cell penetrating peptide

<400> SEQUENCE: 44

Leu Ile Arg Leu Trp Ser His Leu Ile His Ile Trp Phe Gln Asn Arg
1               5                   10                  15

Arg Leu Lys Trp Lys Lys Lys
            20

<210> SEQ ID NO 45
<211> LENGTH: 22
<212> TYPE: PRT
<213> ORGANISM: Artificial Sequence
<220> FEATURE:
<223> OTHER INFORMATION: cell penetrating peptide

<400> SEQUENCE: 45
```

Thr Pro Trp Trp Arg Leu Trp Thr Lys Trp His His Lys Arg Arg Asp
1               5                   10                  15

Leu Pro Arg Lys Pro Glu
            20

<210> SEQ ID NO 46
<211> LENGTH: 20
<212> TYPE: PRT
<213> ORGANISM: Artificial Sequence
<220> FEATURE:
<223> OTHER INFORMATION: cell penetrating peptide

<400> SEQUENCE: 46

Gly Leu Trp Arg Ala Leu Trp Arg Leu Leu Arg Ser Leu Trp Arg Leu
1               5                   10                  15

Leu Trp Arg Ala
            20

<210> SEQ ID NO 47
<211> LENGTH: 24
<212> TYPE: PRT
<213> ORGANISM: Artificial Sequence
<220> FEATURE:
<223> OTHER INFORMATION: cell penetrating peptide

<400> SEQUENCE: 47

Asp Ser His Ala Lys Arg His His Gly Tyr Lys Arg Lys Phe His Glu
1               5                   10                  15

Lys His His Ser His Arg Gly Tyr
            20

<210> SEQ ID NO 48
<211> LENGTH: 16
<212> TYPE: PRT
<213> ORGANISM: Artificial Sequence
<220> FEATURE:
<223> OTHER INFORMATION: cell penetrating peptide

<400> SEQUENCE: 48

Lys Lys Lys Glu Glu Arg Ala Asp Leu Ile Ala Tyr Leu Lys Lys Ala
1               5                   10                  15

<210> SEQ ID NO 49
<211> LENGTH: 30
<212> TYPE: PRT
<213> ORGANISM: Artificial Sequence
<220> FEATURE:
<223> OTHER INFORMATION: chimeric peptide

<400> SEQUENCE: 49

Val Lys Lys Lys Lys Ile Lys Arg Glu Ile Lys Ile Tyr Val Glu Thr
1               5                   10                  15

Leu Asp Gly Ile Phe Glu Gln Trp Ala His Ser Glu Asp Leu
            20                  25                  30

<210> SEQ ID NO 50
<211> LENGTH: 30
<212> TYPE: PRT
<213> ORGANISM: Artificial Sequence
<220> FEATURE:
<223> OTHER INFORMATION: chimeric peptide

<400> SEQUENCE: 50

Val Lys Lys Lys Lys Ile Lys Arg Glu Ile Lys Ile Tyr Ile Glu Thr

```
1               5                   10                  15
Leu Asp Gly Ile Leu Glu Gln Trp Ala Arg Ser Glu Asp Leu
            20                  25                  30
```

<210> SEQ ID NO 51
<211> LENGTH: 30
<212> TYPE: PRT
<213> ORGANISM: Artificial Sequence
<220> FEATURE:
<223> OTHER INFORMATION: chimeric peptide

<400> SEQUENCE: 51

```
Val Lys Lys Lys Lys Ile Lys Ala Glu Ile Lys Ile Tyr Val Glu Thr
1               5                   10                  15
Leu Asp Gly Ile Phe Glu Gln Trp Ala His Ser Glu Asp Leu
            20                  25                  30
```

<210> SEQ ID NO 52
<211> LENGTH: 30
<212> TYPE: PRT
<213> ORGANISM: Artificial Sequence
<220> FEATURE:
<223> OTHER INFORMATION: chimeric peptide

<400> SEQUENCE: 52

```
Val Lys Lys Lys Lys Ile Lys Ala Glu Ile Lys Ile Tyr Ile Glu Thr
1               5                   10                  15
Leu Asp Gly Ile Leu Glu Gln Trp Ala Arg Ser Glu Asp Leu
            20                  25                  30
```

<210> SEQ ID NO 53
<211> LENGTH: 30
<212> TYPE: PRT
<213> ORGANISM: Artificial Sequence
<220> FEATURE:
<223> OTHER INFORMATION: chimeric peptide

<400> SEQUENCE: 53

```
Val Lys Lys Lys Lys Ile Lys Lys Glu Ile Lys Ile Tyr Val Glu Thr
1               5                   10                  15
Leu Asp Gly Ile Phe Glu Gln Trp Ala His Ser Glu Asp Leu
            20                  25                  30
```

<210> SEQ ID NO 54
<211> LENGTH: 30
<212> TYPE: PRT
<213> ORGANISM: Artificial Sequence
<220> FEATURE:
<223> OTHER INFORMATION: chimeric peptide

<400> SEQUENCE: 54

```
Val Lys Lys Lys Lys Ile Lys Lys Glu Ile Lys Ile Tyr Ile Glu Thr
1               5                   10                  15
Leu Asp Gly Ile Leu Glu Gln Trp Ala Arg Ser Glu Asp Leu
            20                  25                  30
```

<210> SEQ ID NO 55
<211> LENGTH: 30
<212> TYPE: PRT
<213> ORGANISM: Artificial Sequence
<220> FEATURE:
<223> OTHER INFORMATION: chimeric peptide

<400> SEQUENCE: 55

Val Lys Lys Lys Lys Ile Lys Asn Glu Ile Lys Ile Tyr Val Glu Thr
1               5                   10                  15

Leu Asp Gly Ile Phe Glu Gln Trp Ala His Ser Glu Asp Leu
            20                  25                  30

<210> SEQ ID NO 56
<211> LENGTH: 30
<212> TYPE: PRT
<213> ORGANISM: Artificial Sequence
<220> FEATURE:
<223> OTHER INFORMATION: chimeric peptide

<400> SEQUENCE: 56

Val Lys Lys Lys Lys Ile Lys Asn Glu Ile Lys Ile Tyr Ile Glu Thr
1               5                   10                  15

Leu Asp Gly Ile Leu Glu Gln Trp Ala Arg Ser Glu Asp Leu
            20                  25                  30

<210> SEQ ID NO 57
<211> LENGTH: 32
<212> TYPE: PRT
<213> ORGANISM: Artificial Sequence
<220> FEATURE:
<223> OTHER INFORMATION: chimeric peptide

<400> SEQUENCE: 57

Val Lys Lys Lys Lys Ile Lys Arg Glu Ile Lys Ile Asp Thr Leu Asp
1               5                   10                  15

His Ile Arg Ala Leu Asp Arg Leu Gln Glu Val Pro His Glu Gly Pro
            20                  25                  30

<210> SEQ ID NO 58
<211> LENGTH: 38
<212> TYPE: PRT
<213> ORGANISM: Artificial Sequence
<220> FEATURE:
<223> OTHER INFORMATION: chimeric peptide

<400> SEQUENCE: 58

Arg Gln Lys Arg Leu Ile Arg Gln Lys Arg Leu Ile Arg Gln Lys Arg
1               5                   10                  15

Leu Ile Asp Thr Leu Asp His Ile Arg Ala Leu Asp Arg Leu Gln Glu
            20                  25                  30

Val Pro His Glu Gly Pro
        35

<210> SEQ ID NO 59
<211> LENGTH: 38
<212> TYPE: PRT
<213> ORGANISM: Artificial Sequence
<220> FEATURE:
<223> OTHER INFORMATION: chimeric peptide

<400> SEQUENCE: 59

Arg His Ser Arg Ile Gly Arg His Ser Arg Ile Gly Arg His Ser Arg
1               5                   10                  15

Ile Gly Asp Thr Leu Asp His Ile Arg Ala Leu Asp Arg Leu Gln Glu
            20                  25                  30

Val Pro His Glu Gly Pro
        35

<210> SEQ ID NO 60
<211> LENGTH: 36

```
<212> TYPE: PRT
<213> ORGANISM: Artificial Sequence
<220> FEATURE:
<223> OTHER INFORMATION: chimeric peptide

<400> SEQUENCE: 60

Arg His Ser Arg Ile Gly Ile Ile Gln Gln Arg Arg Thr Arg Asn Gly
1               5                   10                  15

Asp Thr Leu Asp His Ile Arg Ala Leu Asp Arg Leu Gln Glu Val Pro
            20                  25                  30

His Glu Gly Pro
        35

<210> SEQ ID NO 61
<211> LENGTH: 36
<212> TYPE: PRT
<213> ORGANISM: Artificial Sequence
<220> FEATURE:
<223> OTHER INFORMATION: chimeric peptide

<400> SEQUENCE: 61

Arg His Ser Arg Ile Gly Val Thr Arg Gln Arg Arg Ala Arg Asn Gly
1               5                   10                  15

Asp Thr Leu Asp His Ile Arg Ala Leu Asp Arg Leu Gln Glu Val Pro
            20                  25                  30

His Glu Gly Pro
        35

<210> SEQ ID NO 62
<211> LENGTH: 35
<212> TYPE: PRT
<213> ORGANISM: Artificial Sequence
<220> FEATURE:
<223> OTHER INFORMATION: chimeric peptide

<400> SEQUENCE: 62

Arg Arg Arg Arg Arg Arg Arg Ser Arg Gly Arg Arg Arg Thr Tyr Asp
1               5                   10                  15

Thr Leu Asp His Ile Arg Ala Leu Asp Arg Leu Gln Glu Val Pro His
            20                  25                  30

Glu Gly Pro
        35

<210> SEQ ID NO 63
<211> LENGTH: 2151
<212> TYPE: DNA
<213> ORGANISM: Homo sapiens
<220> FEATURE:
<221> NAME/KEY: CDS
<222> LOCATION: (414)..(1814)

<400> SEQUENCE: 63
gcctctccaa aggctgcaga agtttcttgc taacaaaaag tccgcacatt cgagcaaaga      60
caggctttag cgagttatta aaaacttagg ggcgctcttg tcccccacag ggcccgaccg     120
cacacagcaa ggcgatggcc cagctgtaag ttggtagcac tgagaactag cagcgcgcgc     180
ggagcccgct gagacttgaa tcaatctggt ctaacggttt cccctaaacc gctaggagcc     240
ctcaatcggc gggacagcag ggcgcgtcct ctgccactct cgctccgagg tccccgcgcc     300
agagacgcag ccgcgctccc accacccaca cccaccgcgc cctcgttcgc ctcttctccg     360
ggagccagtc cgcgccaccg ccgccgccca ggccatcgcc accctccgca gcc atg       416
                                                              Met
```

-continued

| | | | | | | | | | | | | | | | | |
|---|---|---|---|---|---|---|---|---|---|---|---|---|---|---|---|---|
| tcc | acc | agg | tcc | gtg | tcc | tcg | tcc | tcc | tac | cgc | agg | atg | ttc | ggc | ggc | 464 |
| Ser | Thr | Arg | Ser | Val | Ser | Ser | Ser | Ser | Tyr | Arg | Arg | Met | Phe | Gly | Gly | |
| | | 5 | | | | | 10 | | | | | 15 | | | | |
| ccg | ggc | acc | gcg | agc | cgg | ccg | agc | tcc | agc | cgg | agc | tac | gtg | act | acg | 512 |
| Pro | Gly | Thr | Ala | Ser | Arg | Pro | Ser | Ser | Ser | Arg | Ser | Tyr | Val | Thr | Thr | |
| | | | 20 | | | | | 25 | | | | | 30 | | | |
| tcc | acc | cgc | acc | tac | agc | ctg | ggc | agc | gcg | ctg | cgc | ccc | agc | acc | agc | 560 |
| Ser | Thr | Arg | Thr | Tyr | Ser | Leu | Gly | Ser | Ala | Leu | Arg | Pro | Ser | Thr | Ser | |
| | 35 | | | | | 40 | | | | | 45 | | | | | |
| cgc | agc | ctc | tac | gcc | tcg | tcc | ccg | ggc | ggc | gtg | tat | gcc | acg | cgc | tcc | 608 |
| Arg | Ser | Leu | Tyr | Ala | Ser | Ser | Pro | Gly | Gly | Val | Tyr | Ala | Thr | Arg | Ser | |
| 50 | | | | | 55 | | | | | 60 | | | | | 65 | |
| tct | gcc | gtg | cgc | ctg | cgg | agc | agc | gtg | ccc | ggg | gtg | cgg | ctc | ctg | cag | 656 |
| Ser | Ala | Val | Arg | Leu | Arg | Ser | Ser | Val | Pro | Gly | Val | Arg | Leu | Leu | Gln | |
| | | | 70 | | | | | 75 | | | | | 80 | | | |
| gac | tcg | gtg | gac | ttc | tcg | ctg | gcc | gac | gcc | atc | aac | acc | gag | ttc | aag | 704 |
| Asp | Ser | Val | Asp | Phe | Ser | Leu | Ala | Asp | Ala | Ile | Asn | Thr | Glu | Phe | Lys | |
| | | | | 85 | | | | | 90 | | | | | 95 | | |
| aac | acc | cgc | acc | aac | gag | aag | gtg | gag | ctg | cag | gag | ctg | aat | gac | cgc | 752 |
| Asn | Thr | Arg | Thr | Asn | Glu | Lys | Val | Glu | Leu | Gln | Glu | Leu | Asn | Asp | Arg | |
| | | 100 | | | | | 105 | | | | | 110 | | | | |
| ttc | gcc | aac | tac | atc | gac | aag | gtg | cgc | ttc | ctg | gag | cag | cag | aat | aag | 800 |
| Phe | Ala | Asn | Tyr | Ile | Asp | Lys | Val | Arg | Phe | Leu | Glu | Gln | Gln | Asn | Lys | |
| | 115 | | | | | 120 | | | | | 125 | | | | | |
| atc | ctg | ctg | gcc | gag | ctc | gag | cag | ctc | aag | ggc | caa | ggc | aag | tcg | cgc | 848 |
| Ile | Leu | Leu | Ala | Glu | Leu | Glu | Gln | Leu | Lys | Gly | Gln | Gly | Lys | Ser | Arg | |
| 130 | | | | | 135 | | | | | 140 | | | | | 145 | |
| ctg | ggg | gac | ctc | tac | gag | gag | gag | atg | cgg | gag | ctg | cgc | cgg | cag | gtg | 896 |
| Leu | Gly | Asp | Leu | Tyr | Glu | Glu | Glu | Met | Arg | Glu | Leu | Arg | Arg | Gln | Val | |
| | | | | 150 | | | | | 155 | | | | | 160 | | |
| gac | cag | cta | acc | aac | gac | aaa | gcc | cgc | gtc | gag | gtg | gag | cgc | gac | aac | 944 |
| Asp | Gln | Leu | Thr | Asn | Asp | Lys | Ala | Arg | Val | Glu | Val | Glu | Arg | Asp | Asn | |
| | | | 165 | | | | | 170 | | | | | 175 | | | |
| ctg | gcc | gag | gac | atc | atg | cgc | ctc | cgg | gag | aaa | ttg | cag | gag | gag | atg | 992 |
| Leu | Ala | Glu | Asp | Ile | Met | Arg | Leu | Arg | Glu | Lys | Leu | Gln | Glu | Glu | Met | |
| | 180 | | | | | 185 | | | | | 190 | | | | | |
| ctt | cag | aga | gag | gaa | gcc | gaa | aac | acc | ctg | caa | tct | ttc | aga | cag | gat | 1040 |
| Leu | Gln | Arg | Glu | Glu | Ala | Glu | Asn | Thr | Leu | Gln | Ser | Phe | Arg | Gln | Asp | |
| 195 | | | | | 200 | | | | | 205 | | | | | | |
| gtt | gac | aat | gcg | tct | ctg | gca | cgt | ctt | gac | ctt | gaa | cgc | aaa | gtg | gaa | 1088 |
| Val | Asp | Asn | Ala | Ser | Leu | Ala | Arg | Leu | Asp | Leu | Glu | Arg | Lys | Val | Glu | |
| 210 | | | | | 215 | | | | | 220 | | | | | 225 | |
| tct | ttg | caa | gaa | gag | att | gcc | ttt | ttg | aag | aaa | ctc | cac | gaa | gag | gaa | 1136 |
| Ser | Leu | Gln | Glu | Glu | Ile | Ala | Phe | Leu | Lys | Lys | Leu | His | Glu | Glu | Glu | |
| | | | | 230 | | | | | 235 | | | | | 240 | | |
| atc | cag | gag | ctg | cag | gct | cag | att | cag | gaa | cag | cat | gtc | caa | atc | gat | 1184 |
| Ile | Gln | Glu | Leu | Gln | Ala | Gln | Ile | Gln | Glu | Gln | His | Val | Gln | Ile | Asp | |
| | | | 245 | | | | | 250 | | | | | 255 | | | |
| gtg | gat | gtt | tcc | aag | cct | gac | ctc | acg | gct | gcc | ctg | cgt | gac | gta | cgt | 1232 |
| Val | Asp | Val | Ser | Lys | Pro | Asp | Leu | Thr | Ala | Ala | Leu | Arg | Asp | Val | Arg | |
| | | | 260 | | | | | 265 | | | | | 270 | | | |
| cag | caa | tat | gaa | agt | gtg | gct | gcc | aag | aac | ctg | cag | gag | gca | gaa | gaa | 1280 |
| Gln | Gln | Tyr | Glu | Ser | Val | Ala | Ala | Lys | Asn | Leu | Gln | Glu | Ala | Glu | Glu | |
| | 275 | | | | | 280 | | | | | 285 | | | | | |
| tgg | tac | aaa | tcc | aag | ttt | gct | gac | ctc | tct | gag | gct | gcc | aac | cgg | aac | 1328 |
| Trp | Tyr | Lys | Ser | Lys | Phe | Ala | Asp | Leu | Ser | Glu | Ala | Ala | Asn | Arg | Asn | |
| 290 | | | | | 295 | | | | | 300 | | | | | 305 | |
| aat | gac | gcc | ctg | cgc | cag | gca | aag | cag | gag | tcc | act | gag | tac | cgg | aga | 1376 |

```
Asn Asp Ala Leu Arg Gln Ala Lys Gln Glu Ser Thr Glu Tyr Arg Arg
            310                 315                 320 cag gtg cag tcc ctc acc tgt gaa gtg gat gcc ctt aaa gga acc aat      1424
Gln Val Gln Ser Leu Thr Cys Glu Val Asp Ala Leu Lys Gly Thr Asn
            325                 330                 335 gag tcc ctg gaa cgc cag atg cgt gaa atg gaa gag aac ttt gcc gtt      1472
Glu Ser Leu Glu Arg Gln Met Arg Glu Met Glu Glu Asn Phe Ala Val
            340                 345                 350 gaa gct gct aac tac caa gac act att ggc cgc ctg cag gat gag att      1520
Glu Ala Ala Asn Tyr Gln Asp Thr Ile Gly Arg Leu Gln Asp Glu Ile
            355                 360                 365 cag aat atg aag gag gaa atg gct cgt cac ctt cgt gaa tac caa gac      1568
Gln Asn Met Lys Glu Glu Met Ala Arg His Leu Arg Glu Tyr Gln Asp
370                 375                 380                 385 ctg ctc aat gtt aag atg gcc ctt gac att gag att gcc acc tac agg      1616
Leu Leu Asn Val Lys Met Ala Leu Asp Ile Glu Ile Ala Thr Tyr Arg
                390                 395                 400 aag ctg ctg gaa ggc gag gag agc agg att tct ctg cct ctt cca aac      1664
Lys Leu Leu Glu Gly Glu Glu Ser Arg Ile Ser Leu Pro Leu Pro Asn
                405                 410                 415 ttt tcc tcc ctg aac ctg agg gaa act aat ctg gat tca ctc cct ctg      1712
Phe Ser Ser Leu Asn Leu Arg Glu Thr Asn Leu Asp Ser Leu Pro Leu
                420                 425                 430 gtt gat acc cac tca aaa agg aca ctt ctg att aag acg gtt gaa act      1760
Val Asp Thr His Ser Lys Arg Thr Leu Leu Ile Lys Thr Val Glu Thr
435                 440                 445 aga gat gga cag gtt atc aac gaa act tct cag cat cac gat gac ctt      1808
Arg Asp Gly Gln Val Ile Asn Glu Thr Ser Gln His His Asp Asp Leu
450                 455                 460                 465 gaa taa aaattgcaca cactcagtgc agcaatatat taccagcaag aataaaaaag       1864
Glu aaatccatat cttaaagaaa cagcttttcaa gtgcctttct gcagttttttc aggagcgcaa   1924 gatagatttg gaataggaat aagctctagt tcttaacaac cgacactcct acaagattta    1984
gaaaaaagtt tacaacataa tctagtttac agaaaaatct tgtgctagaa tacttttttaa   2044 aaggtattt gaataccatt aaaactgctt ttttttttcc agcaagtatc caaccaactt     2104
ggttctgctt caataaatct ttggaaaaac tcaaaaaaaa aaaaaaa                  2151

<210> SEQ ID NO 64
<211> LENGTH: 466
<212> TYPE: PRT
<213> ORGANISM: Homo sapiens

<400> SEQUENCE: 64

Met Ser Thr Arg Ser Val Ser Ser Ser Tyr Arg Arg Met Phe Gly Gly
1               5                   10                  15

Gly Pro Gly Thr Ala Ser Arg Pro Ser Ser Ser Arg Ser Tyr Val Thr
            20                  25                  30

Thr Ser Thr Arg Thr Tyr Ser Leu Gly Ser Ala Leu Arg Pro Ser Thr
        35                  40                  45

Ser Arg Ser Leu Tyr Ala Ser Ser Pro Gly Gly Val Tyr Ala Thr Arg
    50                  55                  60

Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
```

```
                100               105               110
Arg Phe Ala Asn Tyr Ile Asp Lys Val Arg Phe Leu Glu Gln Gln Asn
            115                 120                 125
Lys Ile Leu Leu Ala Glu Leu Glu Gln Leu Lys Gly Gln Gly Lys Ser
        130                 135                 140
Arg Leu Gly Asp Leu Tyr Glu Glu Glu Met Arg Glu Leu Arg Arg Gln
145                 150                 155                 160
Val Asp Gln Leu Thr Asn Asp Lys Ala Arg Val Glu Val Glu Arg Asp
                165                 170                 175
Asn Leu Ala Glu Asp Ile Met Arg Leu Arg Glu Lys Leu Gln Glu Glu
            180                 185                 190
Met Leu Gln Arg Glu Glu Ala Glu Asn Thr Leu Gln Ser Phe Arg Gln
        195                 200                 205
Asp Val Asp Asn Ala Ser Leu Ala Arg Leu Asp Leu Glu Arg Lys Val
210                 215                 220
Glu Ser Leu Gln Glu Glu Ile Ala Phe Leu Lys Lys Leu His Glu Glu
225                 230                 235                 240
Glu Ile Gln Glu Leu Gln Ala Gln Ile Gln Glu Gln His Val Gln Ile
                245                 250                 255
Asp Val Asp Val Ser Lys Pro Asp Leu Thr Ala Ala Leu Arg Asp Val
            260                 265                 270
Arg Gln Gln Tyr Glu Ser Val Ala Ala Lys Asn Leu Gln Glu Ala Glu
        275                 280                 285
Glu Trp Tyr Lys Ser Lys Phe Ala Asp Leu Ser Glu Ala Ala Asn Arg
290                 295                 300
Asn Asn Asp Ala Leu Arg Gln Ala Lys Gln Glu Ser Thr Glu Tyr Arg
305                 310                 315                 320
Arg Gln Val Gln Ser Leu Thr Cys Glu Val Asp Ala Leu Lys Gly Thr
                325                 330                 335
Asn Glu Ser Leu Glu Arg Gln Met Arg Glu Met Glu Glu Asn Phe Ala
            340                 345                 350
Val Glu Ala Ala Asn Tyr Gln Asp Thr Ile Gly Arg Leu Gln Asp Glu
        355                 360                 365
Ile Gln Asn Met Lys Glu Glu Met Ala Arg His Leu Arg Glu Tyr Gln
370                 375                 380
Asp Leu Leu Asn Val Lys Met Ala Leu Asp Ile Glu Ile Ala Thr Tyr
385                 390                 395                 400
Arg Lys Leu Leu Glu Gly Glu Glu Ser Arg Ile Ser Leu Pro Leu Pro
                405                 410                 415
Asn Phe Ser Ser Leu Asn Leu Arg Glu Thr Asn Leu Asp Ser Leu Pro
            420                 425                 430
Leu Val Asp Thr His Ser Lys Arg Thr Leu Leu Ile Lys Thr Val Glu
        435                 440                 445
Thr Arg Asp Gly Gln Val Ile Asn Glu Thr Ser Gln His His Asp Asp
450                 455                 460
Leu Glu
465

<210> SEQ ID NO 65
<211> LENGTH: 12507
<212> TYPE: DNA
<213> ORGANISM: Homo sapiens
<220> FEATURE:
<221> NAME/KEY: CDS
<222> LOCATION: (196)..(9966)
```

<400> SEQUENCE: 65

```
taccgggcgg aggtgagcgc ggcgccggct cctcctgcgg cggactttgg gtgcgacttg      60
acgagcggtg gttcgacaag tggccttgcg ggccggatcg tcccagtgga agagttgtaa     120
atttgcttct ggccttcccc tacgattat acctggcctt cccctacgga ttatactcaa     180
cttactgttt agaaa atg tgg ccc acg aga cgc ctg gtt act atc aaa agg     231
              Met Trp Pro Thr Arg Arg Leu Val Thr Ile Lys Arg
                1               5                  10 agc ggg gtc gac ggt ccc cac ttt ccc ctg agc ctc agc acc tgc ttg      279
Ser Gly Val Asp Gly Pro His Phe Pro Leu Ser Leu Ser Thr Cys Leu
         15                  20                  25 ttt gga agg ggt att gaa tgt gac atc cgt atc cag ctt cct gtt gtg      327
Phe Gly Arg Gly Ile Glu Cys Asp Ile Arg Ile Gln Leu Pro Val Val
     30                  35                  40 tca aaa caa cat tgc aaa att gaa atc cat gag cag gag gca ata tta      375
Ser Lys Gln His Cys Lys Ile Glu Ile His Glu Gln Glu Ala Ile Leu
 45                  50                  55                  60 cat aat ttc agt tcc aca aat cca aca caa gta aat ggg tct gtt att      423
His Asn Phe Ser Ser Thr Asn Pro Thr Gln Val Asn Gly Ser Val Ile
                 65                  70                  75 gat gag cct gta cgg cta aaa cat gga gat gta ata act att att gat      471
Asp Glu Pro Val Arg Leu Lys His Gly Asp Val Ile Thr Ile Ile Asp
             80                  85                  90 cgt tcc ttc agg tat gaa aat gaa agt ctt cag aat gga agg aag tca      519
Arg Ser Phe Arg Tyr Glu Asn Glu Ser Leu Gln Asn Gly Arg Lys Ser
         95                 100                 105 act gaa ttt cca aga aaa ata cgt gaa cag gag cca gca cgt cgt gtc      567
Thr Glu Phe Pro Arg Lys Ile Arg Glu Gln Glu Pro Ala Arg Arg Val
    110                 115                 120 tca aga tct agc ttc tct tct gac cct gat gag aaa gct caa gat tcc      615
Ser Arg Ser Ser Phe Ser Ser Asp Pro Asp Glu Lys Ala Gln Asp Ser
125                 130                 135                 140 aag gcc tat tca aaa atc act gaa gga aaa gtt tca gga aat cct cag      663
Lys Ala Tyr Ser Lys Ile Thr Glu Gly Lys Val Ser Gly Asn Pro Gln
                145                 150                 155 gta cat atc aag aat gtc aaa gaa gac agt acc gca gat gac tca aaa      711
Val His Ile Lys Asn Val Lys Glu Asp Ser Thr Ala Asp Asp Ser Lys
            160                 165                 170 gac agt gtt gct cag gga aca act aat gtt cat tcc tca gaa cat gct      759
Asp Ser Val Ala Gln Gly Thr Thr Asn Val His Ser Ser Glu His Ala
        175                 180                 185 gga cgt aat ggc aga aat gca gct gat ccc att tct ggg gat ttt aaa      807
Gly Arg Asn Gly Arg Asn Ala Ala Asp Pro Ile Ser Gly Asp Phe Lys
    190                 195                 200 gaa att tcc agc gtt aaa tta gtg agc cgt tat gga gaa ttg aag tct      855
Glu Ile Ser Ser Val Lys Leu Val Ser Arg Tyr Gly Glu Leu Lys Ser
205                 210                 215                 220 gtt ccc act aca caa tgt ctt gac aat agc aaa aaa aat gaa tct ccc      903
Val Pro Thr Thr Gln Cys Leu Asp Asn Ser Lys Lys Asn Glu Ser Pro
                225                 230                 235 ttt tgg aag ctt tat gag tca gtg aag aaa gag ttg gat gta aaa tca      951
Phe Trp Lys Leu Tyr Glu Ser Val Lys Lys Glu Leu Asp Val Lys Ser
            240                 245                 250 caa aaa gaa aat gtc cta cag tat tgt aga aaa tct gga tta caa act      999
Gln Lys Glu Asn Val Leu Gln Tyr Cys Arg Lys Ser Gly Leu Gln Thr
        255                 260                 265 gat tac gca aca gag aaa gaa agt gct gat ggt tta cag ggg gag acc     1047
Asp Tyr Ala Thr Glu Lys Glu Ser Ala Asp Gly Leu Gln Gly Glu Thr
```

-continued

| | | | | | | | | | | | | |
|---|---|---|---|---|---|---|---|---|---|---|---|---|
| | | 270 | | | 275 | | | | 280 | | | |
| caa | ctg | ttg | gtc | tcg | cgt | aag | tca | aga | cca | aaa | tct | ggt ggg agc ggc | 1095 |
| Gln | Leu | Leu | Val | Ser | Arg | Lys | Ser | Arg | Pro | Lys | Ser | Gly Gly Ser Gly |
| 285 | | | | | 290 | | | | 295 | | | 300 |
| cac | gct | gtg | gca | gag | cct | gct | tca | cct | gaa | caa | gag | ctt gac cag aac | 1143 |
| His | Ala | Val | Ala | Glu | Pro | Ala | Ser | Pro | Glu | Gln | Glu | Leu Asp Gln Asn |
| | | | | 305 | | | | 310 | | | | 315 |
| aag | ggg | aag | gga | aga | gac | gtg | gag | tct | gtt | cag | act | ccc agc aag gct | 1191 |
| Lys | Gly | Lys | Gly | Arg | Asp | Val | Glu | Ser | Val | Gln | Thr | Pro Ser Lys Ala |
| | | | 320 | | | | | 325 | | | | 330 |
| gtg | ggc | gcc | agc | ttt | cct | ctc | tat | gag | ccg | gct | aaa | atg aag acc cct | 1239 |
| Val | Gly | Ala | Ser | Phe | Pro | Leu | Tyr | Glu | Pro | Ala | Lys | Met Lys Thr Pro |
| | | | 335 | | | | 340 | | | | | 345 |
| gta | caa | tat | tca | cag | caa | caa | aat | tct | cca | caa | aaa | cat aag aac aaa | 1287 |
| Val | Gln | Tyr | Ser | Gln | Gln | Gln | Asn | Ser | Pro | Gln | Lys | His Lys Asn Lys |
| 350 | | | | | 355 | | | | 360 | | | |
| gac | ctg | tat | act | act | ggt | aga | aga | gaa | tct | gtg | aat | ctg ggt aaa agt | 1335 |
| Asp | Leu | Tyr | Thr | Thr | Gly | Arg | Arg | Glu | Ser | Val | Asn | Leu Gly Lys Ser |
| 365 | | | | 370 | | | | 375 | | | | 380 |
| gaa | ggc | ttc | aag | gct | ggt | gat | aaa | act | ctt | act | ccc | agg aag ctt tca | 1383 |
| Glu | Gly | Phe | Lys | Ala | Gly | Asp | Lys | Thr | Leu | Thr | Pro | Arg Lys Leu Ser |
| | | | | 385 | | | | 390 | | | | 395 |
| act | aga | aat | cga | aca | cca | gct | aaa | gtt | gaa | gat | gca | gct gac tct gcc | 1431 |
| Thr | Arg | Asn | Arg | Thr | Pro | Ala | Lys | Val | Glu | Asp | Ala | Ala Asp Ser Ala |
| | | | 400 | | | | 405 | | | | | 410 |
| act | aag | cca | gaa | aat | ctc | tct | tcc | aaa | acc | aga | gga | agt att cct aca | 1479 |
| Thr | Lys | Pro | Glu | Asn | Leu | Ser | Ser | Lys | Thr | Arg | Gly | Ser Ile Pro Thr |
| | | 415 | | | | 420 | | | | 425 | | |
| gat | gtg | gaa | gtt | ctg | cct | acg | gaa | act | gaa | att | cac | aat gag cca ttt | 1527 |
| Asp | Val | Glu | Val | Leu | Pro | Thr | Glu | Thr | Glu | Ile | His | Asn Glu Pro Phe |
| | 430 | | | | 435 | | | | 440 | | | |
| tta | act | ctg | tgg | ctc | act | caa | gtt | gag | agg | aag | atc | caa aag gat tcc | 1575 |
| Leu | Thr | Leu | Trp | Leu | Thr | Gln | Val | Glu | Arg | Lys | Ile | Gln Lys Asp Ser |
| 445 | | | | 450 | | | | 455 | | | | 460 |
| ctc | agc | aag | cct | gag | aaa | ttg | ggc | act | aca | gct | gga | cag atg tgc tct | 1623 |
| Leu | Ser | Lys | Pro | Glu | Lys | Leu | Gly | Thr | Thr | Ala | Gly | Gln Met Cys Ser |
| | | | 465 | | | | 470 | | | | | 475 |
| ggg | tta | cct | ggt | ctt | agt | tca | gtt | gat | atc | aac | aac | ttt ggt gat tcc | 1671 |
| Gly | Leu | Pro | Gly | Leu | Ser | Ser | Val | Asp | Ile | Asn | Asn | Phe Gly Asp Ser |
| | | 480 | | | | 485 | | | | | 490 | |
| att | aat | gag | agt | gag | gga | ata | cct | ttg | aaa | aga | agg | cgt gtg tcc ttt | 1719 |
| Ile | Asn | Glu | Ser | Glu | Gly | Ile | Pro | Leu | Lys | Arg | Arg | Arg Val Ser Phe |
| | | 495 | | | | 500 | | | | 505 | | |
| ggt | ggg | cac | cta | aga | cct | gaa | cta | ttt | gat | gaa | aac | ttg cct cct aat | 1767 |
| Gly | Gly | His | Leu | Arg | Pro | Glu | Leu | Phe | Asp | Glu | Asn | Leu Pro Pro Asn |
| | 510 | | | | 515 | | | | 520 | | | |
| acg | cct | ctc | aaa | agg | gga | gaa | gcc | cca | acc | aaa | aga | aag tct ctg gta | 1815 |
| Thr | Pro | Leu | Lys | Arg | Gly | Glu | Ala | Pro | Thr | Lys | Arg | Lys Ser Leu Val |
| 525 | | | | 530 | | | | 535 | | | | 540 |
| atg | cac | act | cca | cct | gtc | ctg | aag | aaa | atc | atc | aag | gaa cag cct caa | 1863 |
| Met | His | Thr | Pro | Pro | Val | Leu | Lys | Lys | Ile | Ile | Lys | Glu Gln Pro Gln |
| | | | | 545 | | | | 550 | | | | 555 |
| cca | tca | gga | aaa | caa | gag | tca | ggt | tca | gaa | atc | cat | gtg gaa gtg aag | 1911 |
| Pro | Ser | Gly | Lys | Gln | Glu | Ser | Gly | Ser | Glu | Ile | His | Val Glu Val Lys |
| | | | 560 | | | | | 565 | | | | 570 |
| gca | caa | agc | ttg | gtt | ata | agc | cct | cca | gct | cct | agt | cct agg aaa act | 1959 |
| Ala | Gln | Ser | Leu | Val | Ile | Ser | Pro | Pro | Ala | Pro | Ser | Pro Arg Lys Thr |
| | | 575 | | | | 580 | | | | 585 | | |
| cca | gtt | gcc | agt | gat | caa | cgc | cgt | agg | tcc | tgc | aaa | aca gcc cct gct | 2007 |

-continued

```
              Pro Val Ala Ser Asp Gln Arg Arg Ser Cys Lys Thr Ala Pro Ala
              590                 595                 600 tcc agc agc aaa tct cag aca gag gtt cct aag aga gga ggg aga aag     2055
Ser Ser Ser Lys Ser Gln Thr Glu Val Pro Lys Arg Gly Gly Arg Lys
605                 610                 615                 620 agt ggc aac ctg cct tca aag aga gtg tct atc agc cga agt caa cat     2103
Ser Gly Asn Leu Pro Ser Lys Arg Val Ser Ile Ser Arg Ser Gln His
                625                 630                 635 gat att tta cag atg ata tgt tcc aaa aga aga agt ggt gct tcg gaa     2151
Asp Ile Leu Gln Met Ile Cys Ser Lys Arg Arg Ser Gly Ala Ser Glu
            640                 645                 650 gca aat ctg att gtt gca aaa tca tgg gca gat gta gta aaa ctt ggt     2199
Ala Asn Leu Ile Val Ala Lys Ser Trp Ala Asp Val Val Lys Leu Gly
        655                 660                 665 gca aaa caa aca caa act aaa gtc ata aaa cat ggt cct caa agg tca     2247
Ala Lys Gln Thr Gln Thr Lys Val Ile Lys His Gly Pro Gln Arg Ser
    670                 675                 680 atg aac aaa agg caa aga aga cct gct act cca aag aag cct gtg ggc     2295
Met Asn Lys Arg Gln Arg Arg Pro Ala Thr Pro Lys Lys Pro Val Gly
685                 690                 695                 700 gaa gtt cac agt caa ttt agt aca ggc cac gca aac tct cct tgt acc     2343
Glu Val His Ser Gln Phe Ser Thr Gly His Ala Asn Ser Pro Cys Thr
                705                 710                 715 ata ata ata ggg aaa gct cat act gaa aaa gta cat gtg cct gct cga     2391
Ile Ile Ile Gly Lys Ala His Thr Glu Lys Val His Val Pro Ala Arg
            720                 725                 730 ccc tac aga gtg ctc aac aac ttc att tcc aac caa aaa atg gac ttt     2439
Pro Tyr Arg Val Leu Asn Asn Phe Ile Ser Asn Gln Lys Met Asp Phe
        735                 740                 745 aag gaa gat ctt tca gga ata gct gaa atg ttc aag acc cca gtg aag     2487
Lys Glu Asp Leu Ser Gly Ile Ala Glu Met Phe Lys Thr Pro Val Lys
    750                 755                 760 gag caa ccg cag ttg aca agc aca tgt cac atc gct att tca aat tca     2535
Glu Gln Pro Gln Leu Thr Ser Thr Cys His Ile Ala Ile Ser Asn Ser
765                 770                 775                 780 gag aat ttg ctt gga aaa cag ttt caa gga act gat tca gga gaa gaa     2583
Glu Asn Leu Leu Gly Lys Gln Phe Gln Gly Thr Asp Ser Gly Glu Glu
                785                 790                 795 cct ctg ctc ccc acc tca gag agt ttt gga gga aat gtg ttc ttc agt     2631
Pro Leu Leu Pro Thr Ser Glu Ser Phe Gly Gly Asn Val Phe Phe Ser
            800                 805                 810 gca cag aat gca gca aaa cag cca tct gat aaa tgc tct gca agc cct     2679
Ala Gln Asn Ala Ala Lys Gln Pro Ser Asp Lys Cys Ser Ala Ser Pro
        815                 820                 825 ccc tta aga cgg cag tgt att aga gaa aat gga aac gta gca aaa acg     2727
Pro Leu Arg Arg Gln Cys Ile Arg Glu Asn Gly Asn Val Ala Lys Thr
    830                 835                 840 ccc agg aac acc tac aaa atg act tct ctg gag aca aaa act tca gat     2775
Pro Arg Asn Thr Tyr Lys Met Thr Ser Leu Glu Thr Lys Thr Ser Asp
845                 850                 855                 860 act gag aca gag cct tca aaa aca gta tcc act gca aac agg tca gga     2823
Thr Glu Thr Glu Pro Ser Lys Thr Val Ser Thr Ala Asn Arg Ser Gly
                865                 870                 875 agg tct aca gag ttc agg aat ata cag aag cta cct gtg gaa agt aag     2871
Arg Ser Thr Glu Phe Arg Asn Ile Gln Lys Leu Pro Val Glu Ser Lys
            880                 885                 890 agt gaa gaa aca aat aca gaa att gtt gag tgc atc cta aaa aga ggt     2919
Ser Glu Glu Thr Asn Thr Glu Ile Val Glu Cys Ile Leu Lys Arg Gly
        895                 900                 905
```

-continued

| | |
|---|---|
| cag aag gca aca cta cta caa caa agg aga gaa gga gag atg aag gaa<br>Gln Lys Ala Thr Leu Leu Gln Gln Arg Arg Glu Gly Glu Met Lys Glu<br>910                    915                    920 | 2967 |
| ata gaa aga cct ttt gag aca tat aag gaa aat att gaa tta aaa gaa<br>Ile Glu Arg Pro Phe Glu Thr Tyr Lys Glu Asn Ile Glu Leu Lys Glu<br>925                    930                    935                    940 | 3015 |
| aac gat gaa aag atg aaa gca atg aag aga tca aga act tgg ggg cag<br>Asn Asp Glu Lys Met Lys Ala Met Lys Arg Ser Arg Thr Trp Gly Gln<br>945                    950                    955 | 3063 |
| aaa tgt gca cca atg tct gac ctg aca gac ctc aag agc ttg cct gat<br>Lys Cys Ala Pro Met Ser Asp Leu Thr Asp Leu Lys Ser Leu Pro Asp<br>960                    965                    970 | 3111 |
| aca gaa ctc atg aaa gac acg gca cgt ggc cag aat ctc ctc caa acc<br>Thr Glu Leu Met Lys Asp Thr Ala Arg Gly Gln Asn Leu Leu Gln Thr<br>975                    980                    985 | 3159 |
| caa gat cat gcc aag gca cca aag agt gag aaa ggc aaa atc act aaa<br>Gln Asp His Ala Lys Ala Pro Lys Ser Glu Lys Gly Lys Ile Thr Lys<br>990                    995                    1000 | 3207 |
| atg ccc tgc cag tca tta caa cca gaa cca ata aac acc cca aca<br>Met Pro Cys Gln Ser Leu Gln Pro Glu Pro Ile Asn Thr Pro Thr<br>1005                  1010                    1015 | 3252 |
| cac aca aaa caa cag ttg aag gca tcc ctg ggg aaa gta ggt gtg<br>His Thr Lys Gln Gln Leu Lys Ala Ser Leu Gly Lys Val Gly Val<br>1020                  1025                    1030 | 3297 |
| aaa gaa gag ctc cta gca gtc ggc aag ttc aca cgg acg tca ggg<br>Lys Glu Glu Leu Leu Ala Val Gly Lys Phe Thr Arg Thr Ser Gly<br>1035                  1040                    1045 | 3342 |
| gag acc acg cac acg cac aga gag cca gca gga gat ggc aag agc<br>Glu Thr Thr His Thr His Arg Glu Pro Ala Gly Asp Gly Lys Ser<br>1050                  1055                    1060 | 3387 |
| atc aga acg ttt aag gag tct cca aag cag atc ctg gac cca gca<br>Ile Arg Thr Phe Lys Glu Ser Pro Lys Gln Ile Leu Asp Pro Ala<br>1065                  1070                    1075 | 3432 |
| gcc cgt gta act gga atg aag aag tgg cca aga acg cct aag gaa<br>Ala Arg Val Thr Gly Met Lys Lys Trp Pro Arg Thr Pro Lys Glu<br>1080                  1085                    1090 | 3477 |
| gag gcc cag tca cta gaa gac ctg gct ggc ttc aaa gag ctc ttc<br>Glu Ala Gln Ser Leu Glu Asp Leu Ala Gly Phe Lys Glu Leu Phe<br>1095                  1100                    1105 | 3522 |
| cag aca cca ggt ccc tct gag gaa tca atg act gat gag aaa act<br>Gln Thr Pro Gly Pro Ser Glu Glu Ser Met Thr Asp Glu Lys Thr<br>1110                  1115                    1120 | 3567 |
| acc aaa ata gcc tgc aaa tct cca cca cca gaa tca gtg gac act<br>Thr Lys Ile Ala Cys Lys Ser Pro Pro Pro Glu Ser Val Asp Thr<br>1125                  1130                    1135 | 3612 |
| cca aca agc aca aag caa tgg cct aag aga agt ctc agg aaa gca<br>Pro Thr Ser Thr Lys Gln Trp Pro Lys Arg Ser Leu Arg Lys Ala<br>1140                  1145                    1150 | 3657 |
| gat gta gag gaa gaa ttc tta gca ctc agg aaa cta aca cca tca<br>Asp Val Glu Glu Glu Phe Leu Ala Leu Arg Lys Leu Thr Pro Ser<br>1155                  1160                    1165 | 3702 |
| gca ggg aaa gcc atg ctt acg ccc aaa cca gca gga ggt gat gag<br>Ala Gly Lys Ala Met Leu Thr Pro Lys Pro Ala Gly Gly Asp Glu<br>1170                  1175                    1180 | 3747 |
| aaa gac att aaa gca ttt atg gga act cca gtg cag aaa ctg gac<br>Lys Asp Ile Lys Ala Phe Met Gly Thr Pro Val Gln Lys Leu Asp<br>1185                  1190                    1195 | 3792 |
| ctg gca gga act tta cct ggc agc aaa aga cag cta cag act cct<br>Leu Ala Gly Thr Leu Pro Gly Ser Lys Arg Gln Leu Gln Thr Pro<br>1200                  1205                    1210 | 3837 |

```
aag gaa aag gcc cag gct cta gaa gac ctg gct ggc ttt aaa gag      3882
Lys Glu Lys Ala Gln Ala Leu Glu Asp Leu Ala Gly Phe Lys Glu
1215                1220                1225 ctc ttc cag act cct ggt cac acc gag gaa tta gtg gct gct ggt      3927
Leu Phe Gln Thr Pro Gly His Thr Glu Glu Leu Val Ala Ala Gly
1230                1235                1240 aaa acc act aaa ata ccc tgc gac tct cca cag tca gac cca gtg      3972
Lys Thr Thr Lys Ile Pro Cys Asp Ser Pro Gln Ser Asp Pro Val
1245                1250                1255 gac acc cca aca agc aca aag caa cga ccc aag aga agt atc agg      4017
Asp Thr Pro Thr Ser Thr Lys Gln Arg Pro Lys Arg Ser Ile Arg
1260                1265                1270 aaa gca gat gta gag gga gaa ctc tta gcg tgc agg aat cta atg      4062
Lys Ala Asp Val Glu Gly Glu Leu Leu Ala Cys Arg Asn Leu Met
1275                1280                1285 cca tca gca ggc aaa gcc atg cac acg cct aaa cca tca gta ggt      4107
Pro Ser Ala Gly Lys Ala Met His Thr Pro Lys Pro Ser Val Gly
1290                1295                1300 gaa gag aaa gac atc atc ata ttt gtg gga act cca gtg cag aaa      4152
Glu Glu Lys Asp Ile Ile Ile Phe Val Gly Thr Pro Val Gln Lys
1305                1310                1315 ctg gac ctg aca gag aac tta acc ggc agc aag aga cgg cca caa      4197
Leu Asp Leu Thr Glu Asn Leu Thr Gly Ser Lys Arg Arg Pro Gln
1320                1325                1330 act cct aag gaa gag gcc cag gct ctg gaa gac ctg act ggc ttt      4242
Thr Pro Lys Glu Glu Ala Gln Ala Leu Glu Asp Leu Thr Gly Phe
1335                1340                1345 aaa gag ctc ttc cag acc cct ggt cat act gaa gaa gca gtg gct      4287
Lys Glu Leu Phe Gln Thr Pro Gly His Thr Glu Glu Ala Val Ala
1350                1355                1360 gct ggc aaa act act aaa atg ccc tgc gaa tct tct cca cca gaa      4332
Ala Gly Lys Thr Thr Lys Met Pro Cys Glu Ser Ser Pro Pro Glu
1365                1370                1375 tca gca gac acc cca aca agc aca aga agg cag ccc aag aca cct      4377
Ser Ala Asp Thr Pro Thr Ser Thr Arg Arg Gln Pro Lys Thr Pro
1380                1385                1390 ttg gag aaa agg gac gta cag aag gag ctc tca gcc ctg aag aag      4422
Leu Glu Lys Arg Asp Val Gln Lys Glu Leu Ser Ala Leu Lys Lys
1395                1400                1405 ctc aca cag aca tca ggg gaa acc aca cac aca gat aaa gta cca      4467
Leu Thr Gln Thr Ser Gly Glu Thr Thr His Thr Asp Lys Val Pro
1410                1415                1420 gga ggt gag gat aaa agc atc aac gcg ttt agg gaa act gca aaa      4512
Gly Gly Glu Asp Lys Ser Ile Asn Ala Phe Arg Glu Thr Ala Lys
1425                1430                1435 cag aaa ctg gac cca gca gca agt gta act ggt agc aag agg cac      4557
Gln Lys Leu Asp Pro Ala Ala Ser Val Thr Gly Ser Lys Arg His
1440                1445                1450 cca aaa act aag gaa aag gcc caa ccc cta gaa gac ctg gct ggc      4602
Pro Lys Thr Lys Glu Lys Ala Gln Pro Leu Glu Asp Leu Ala Gly
1455                1460                1465 ttg aaa gag ctc ttc cag aca cca gta tgc act gac aag ccc acg      4647
Leu Lys Glu Leu Phe Gln Thr Pro Val Cys Thr Asp Lys Pro Thr
1470                1475                1480 act cac gag aaa act acc aaa ata gcc tgc aga tca caa cca gac      4692
Thr His Glu Lys Thr Thr Lys Ile Ala Cys Arg Ser Gln Pro Asp
1485                1490                1495 cca gtg gac aca cca aca agc tcc aag cca cag tcc aag aga agt      4737
Pro Val Asp Thr Pro Thr Ser Ser Lys Pro Gln Ser Lys Arg Ser
```

-continued

| | | | |
|---|---|---|---|
| ctc agg aaa gtg gac gta gaa gaa gaa ttc ttc gca ctc agg aaa<br>Leu Arg Lys Val Asp Val Glu Glu Glu Phe Phe Ala Leu Arg Lys<br>1515                                  1520                        1525 | 4782 |
| cga aca cca tca gca ggc aaa gcc atg cac aca ccc aaa cca gca<br>Arg Thr Pro Ser Ala Gly Lys Ala Met His Thr Pro Lys Pro Ala<br>1530                                  1535                        1540 | 4827 |
| gta agt ggt gag aaa aac atc tac gca ttt atg gga act cca gtg<br>Val Ser Gly Glu Lys Asn Ile Tyr Ala Phe Met Gly Thr Pro Val<br>1545                                  1550                        1555 | 4872 |
| cag aaa ctg gac ctg aca gag aac tta act ggc agc aag aga cgg<br>Gln Lys Leu Asp Leu Thr Glu Asn Leu Thr Gly Ser Lys Arg Arg<br>1560                                  1565                        1570 | 4917 |
| cta caa act cct aag gaa aag gcc cag gct cta gaa gac ctg gct<br>Leu Gln Thr Pro Lys Glu Lys Ala Gln Ala Leu Glu Asp Leu Ala<br>1575                                  1580                        1585 | 4962 |
| ggc ttt aaa gag ctc ttc cag aca cga ggt cac act gag gaa tca<br>Gly Phe Lys Glu Leu Phe Gln Thr Arg Gly His Thr Glu Glu Ser<br>1590                                  1595                        1600 | 5007 |
| atg act aac gat aaa act gcc aaa gta gcc tgc aaa tct tca caa<br>Met Thr Asn Asp Lys Thr Ala Lys Val Ala Cys Lys Ser Ser Gln<br>1605                                  1610                        1615 | 5052 |
| cca gac cca gac aaa aac cca gca agc tcc aag cga cgg ctc aag<br>Pro Asp Pro Asp Lys Asn Pro Ala Ser Ser Lys Arg Arg Leu Lys<br>1620                                  1625                        1630 | 5097 |
| aca tcc ctg ggg aaa gtg ggc gtg aaa gaa gag ctc cta gca gtt<br>Thr Ser Leu Gly Lys Val Gly Val Lys Glu Glu Leu Leu Ala Val<br>1635                                  1640                        1645 | 5142 |
| ggc aag ctc aca cag aca tca gga gag act aca cac aca cac aca<br>Gly Lys Leu Thr Gln Thr Ser Gly Glu Thr Thr His Thr His Thr<br>1650                                  1655                        1660 | 5187 |
| gag cca aca gga gat ggt aag agc atg aaa gca ttt atg gag tct<br>Glu Pro Thr Gly Asp Gly Lys Ser Met Lys Ala Phe Met Glu Ser<br>1665                                  1670                        1675 | 5232 |
| cca aag cag atc tta gac tca gca gca agt cta act ggc agc aag<br>Pro Lys Gln Ile Leu Asp Ser Ala Ala Ser Leu Thr Gly Ser Lys<br>1680                                  1685                        1690 | 5277 |
| agg cag ctg aga act cct aag gga aag tct gaa gtc cct gaa gac<br>Arg Gln Leu Arg Thr Pro Lys Gly Lys Ser Glu Val Pro Glu Asp<br>1695                                  1700                        1705 | 5322 |
| ctg gcc ggc ttc atc gag ctc ttc cag aca cca agt cac act aag<br>Leu Ala Gly Phe Ile Glu Leu Phe Gln Thr Pro Ser His Thr Lys<br>1710                                  1715                        1720 | 5367 |
| gaa tca atg act aac gaa aaa act acc aaa gta tcc tac aga gct<br>Glu Ser Met Thr Asn Glu Lys Thr Thr Lys Val Ser Tyr Arg Ala<br>1725                                  1730                        1735 | 5412 |
| tca cag cca gac cta gtg gac acc cca aca agc tcc aag cca cag<br>Ser Gln Pro Asp Leu Val Asp Thr Pro Thr Ser Ser Lys Pro Gln<br>1740                                  1745                        1750 | 5457 |
| ccc aag aga agt ctc agg aaa gca gac act gaa gaa gaa ttt tta<br>Pro Lys Arg Ser Leu Arg Lys Ala Asp Thr Glu Glu Glu Phe Leu<br>1755                                  1760                        1765 | 5502 |
| gca ttt agg aaa caa acg cca tca gca ggc aaa gcc atg cac aca<br>Ala Phe Arg Lys Gln Thr Pro Ser Ala Gly Lys Ala Met His Thr<br>1770                                  1775                        1780 | 5547 |
| ccc aaa cca gca gta ggt gaa gag aaa gac atc aac acg ttt ttg<br>Pro Lys Pro Ala Val Gly Glu Glu Lys Asp Ile Asn Thr Phe Leu<br>1785                                  1790                        1795 | 5592 |
| gga act cca gtg cag aaa ctg gac cag cca gga aat tta cct ggc | 5637 |

| | | | | | | | | | | | |
|---|---|---|---|---|---|---|---|---|---|---|---|
| Gly | Thr | Pro | Val | Gln | Lys | Leu | Asp | Gln | Pro | Gly | Asn Leu Pro Gly |
| 1800 | | | | 1805 | | | | 1810 | | | |

| | | | | | | | | | | | | |
|---|---|---|---|---|---|---|---|---|---|---|---|---|
| agc | aat | aga | cgg | cta | caa | act | cgt | aag | gaa | aag | gcc cag gct cta | 5682 |
| Ser | Asn | Arg | Arg | Leu | Gln | Thr | Arg | Lys | Glu | Lys | Ala Gln Ala Leu | |
| 1815 | | | | 1820 | | | | 1825 | | | | |

| | | | | | | | | | | | | |
|---|---|---|---|---|---|---|---|---|---|---|---|---|
| gaa | gaa | ctg | act | ggc | ttc | aga | gag | ctt | ttc | cag | aca cca tgc act | 5727 |
| Glu | Glu | Leu | Thr | Gly | Phe | Arg | Glu | Leu | Phe | Gln | Thr Pro Cys Thr | |
| 1830 | | | | 1835 | | | | 1840 | | | | |

| | | | | | | | | | | | | |
|---|---|---|---|---|---|---|---|---|---|---|---|---|
| gat | aac | ccc | acg | act | gat | gag | aaa | act | acc | aaa | aaa ata ctc tgc | 5772 |
| Asp | Asn | Pro | Thr | Thr | Asp | Glu | Lys | Thr | Thr | Lys | Lys Ile Leu Cys | |
| 1845 | | | | 1850 | | | | 1855 | | | | |

| | | | | | | | | | | | | |
|---|---|---|---|---|---|---|---|---|---|---|---|---|
| aaa | tct | ccg | caa | tca | gac | cca | gcg | gac | acc | cca | aca aac aca aag | 5817 |
| Lys | Ser | Pro | Gln | Ser | Asp | Pro | Ala | Asp | Thr | Pro | Thr Asn Thr Lys | |
| 1860 | | | | 1865 | | | | 1870 | | | | |

| | | | | | | | | | | | | |
|---|---|---|---|---|---|---|---|---|---|---|---|---|
| caa | cgg | ccc | aag | aga | agc | ctc | aag | aaa | gca | gac | gta gag gaa gaa | 5862 |
| Gln | Arg | Pro | Lys | Arg | Ser | Leu | Lys | Lys | Ala | Asp | Val Glu Glu Glu | |
| 1875 | | | | 1880 | | | | 1885 | | | | |

| | | | | | | | | | | | | |
|---|---|---|---|---|---|---|---|---|---|---|---|---|
| ttt | tta | gca | ttc | agg | aaa | cta | aca | cca | tca | gca | ggc aaa gcc atg | 5907 |
| Phe | Leu | Ala | Phe | Arg | Lys | Leu | Thr | Pro | Ser | Ala | Gly Lys Ala Met | |
| 1890 | | | | 1895 | | | | 1900 | | | | |

| | | | | | | | | | | | | |
|---|---|---|---|---|---|---|---|---|---|---|---|---|
| cac | acg | cct | aaa | gca | gca | gta | ggt | gaa | gag | aaa | gac atc aac aca | 5952 |
| His | Thr | Pro | Lys | Ala | Ala | Val | Gly | Glu | Glu | Lys | Asp Ile Asn Thr | |
| 1905 | | | | 1910 | | | | 1915 | | | | |

| | | | | | | | | | | | | |
|---|---|---|---|---|---|---|---|---|---|---|---|---|
| ttt | gtg | ggg | act | cca | gtg | gag | aaa | ctg | gac | ctg | cta gga aat tta | 5997 |
| Phe | Val | Gly | Thr | Pro | Val | Glu | Lys | Leu | Asp | Leu | Leu Gly Asn Leu | |
| 1920 | | | | 1925 | | | | 1930 | | | | |

| | | | | | | | | | | | | |
|---|---|---|---|---|---|---|---|---|---|---|---|---|
| cct | ggc | agc | aag | aga | cgg | cca | caa | act | cct | aaa | gaa aag gcc aag | 6042 |
| Pro | Gly | Ser | Lys | Arg | Arg | Pro | Gln | Thr | Pro | Lys | Glu Lys Ala Lys | |
| 1935 | | | | 1940 | | | | 1945 | | | | |

| | | | | | | | | | | | | |
|---|---|---|---|---|---|---|---|---|---|---|---|---|
| gct | cta | gaa | gat | ctg | gct | ggc | ttc | aaa | gag | ctc | ttc cag aca cca | 6087 |
| Ala | Leu | Glu | Asp | Leu | Ala | Gly | Phe | Lys | Glu | Leu | Phe Gln Thr Pro | |
| 1950 | | | | 1955 | | | | 1960 | | | | |

| | | | | | | | | | | | | |
|---|---|---|---|---|---|---|---|---|---|---|---|---|
| ggt | cac | act | gag | gaa | tca | atg | acc | gat | gac | aaa | atc aca gaa gta | 6132 |
| Gly | His | Thr | Glu | Glu | Ser | Met | Thr | Asp | Asp | Lys | Ile Thr Glu Val | |
| 1965 | | | | 1970 | | | | 1975 | | | | |

| | | | | | | | | | | | | |
|---|---|---|---|---|---|---|---|---|---|---|---|---|
| tcc | tgc | aaa | tct | cca | caa | cca | gac | cca | gtc | aaa | acc cca aca agc | 6177 |
| Ser | Cys | Lys | Ser | Pro | Gln | Pro | Asp | Pro | Val | Lys | Thr Pro Thr Ser | |
| 1980 | | | | 1985 | | | | 1990 | | | | |

| | | | | | | | | | | | | |
|---|---|---|---|---|---|---|---|---|---|---|---|---|
| tcc | aag | caa | cga | ctc | aag | ata | tcc | ttg | ggg | aaa | gta ggt gtg aaa | 6222 |
| Ser | Lys | Gln | Arg | Leu | Lys | Ile | Ser | Leu | Gly | Lys | Val Gly Val Lys | |
| 1995 | | | | 2000 | | | | 2005 | | | | |

| | | | | | | | | | | | | |
|---|---|---|---|---|---|---|---|---|---|---|---|---|
| gaa | gag | gtc | cta | cca | gtc | ggc | aag | ctc | aca | cag | acg tca ggg aag | 6267 |
| Glu | Glu | Val | Leu | Pro | Val | Gly | Lys | Leu | Thr | Gln | Thr Ser Gly Lys | |
| 2010 | | | | 2015 | | | | 2020 | | | | |

| | | | | | | | | | | | | |
|---|---|---|---|---|---|---|---|---|---|---|---|---|
| acc | aca | cag | aca | cac | aga | gag | aca | gca | gga | gat | gga aag agc atc | 6312 |
| Thr | Thr | Gln | Thr | His | Arg | Glu | Thr | Ala | Gly | Asp | Gly Lys Ser Ile | |
| 2025 | | | | 2030 | | | | 2035 | | | | |

| | | | | | | | | | | | | |
|---|---|---|---|---|---|---|---|---|---|---|---|---|
| aaa | gcg | ttt | aag | gaa | tct | gca | aag | cag | atg | ctg | gac cca gca aac | 6357 |
| Lys | Ala | Phe | Lys | Glu | Ser | Ala | Lys | Gln | Met | Leu | Asp Pro Ala Asn | |
| 2040 | | | | 2045 | | | | 2050 | | | | |

| | | | | | | | | | | | | |
|---|---|---|---|---|---|---|---|---|---|---|---|---|
| tat | gga | act | ggg | atg | gag | agg | tgg | cca | aga | aca | cct aag gaa gag | 6402 |
| Tyr | Gly | Thr | Gly | Met | Glu | Arg | Trp | Pro | Arg | Thr | Pro Lys Glu Glu | |
| 2055 | | | | 2060 | | | | 2065 | | | | |

| | | | | | | | | | | | | |
|---|---|---|---|---|---|---|---|---|---|---|---|---|
| gcc | caa | tca | cta | gaa | gac | ctg | gcc | ggc | ttc | aaa | gag ctc ttc cag | 6447 |
| Ala | Gln | Ser | Leu | Glu | Asp | Leu | Ala | Gly | Phe | Lys | Glu Leu Phe Gln | |
| 2070 | | | | 2075 | | | | 2080 | | | | |

| | | | | | | | | | | | | |
|---|---|---|---|---|---|---|---|---|---|---|---|---|
| aca | cca | gac | cac | act | gag | gaa | tca | aca | act | gat | gac aaa act acc | 6492 |
| Thr | Pro | Asp | His | Thr | Glu | Glu | Ser | Thr | Thr | Asp | Asp Lys Thr Thr | |
| 2085 | | | | 2090 | | | | 2095 | | | | |

```
aaa ata gcc tgc aaa tct cca cca cca gaa tca atg gac act cca      6537
Lys Ile Ala Cys Lys Ser Pro Pro Pro Glu Ser Met Asp Thr Pro
2100                2105                2110 aca agc aca agg agg cgg ccc aaa aca cct ttg ggg aaa agg gat      6582
Thr Ser Thr Arg Arg Arg Pro Lys Thr Pro Leu Gly Lys Arg Asp
2115                2120                2125 ata gtg gaa gag ctc tca gcc ctg aag cag ctc aca cag acc aca      6627
Ile Val Glu Glu Leu Ser Ala Leu Lys Gln Leu Thr Gln Thr Thr
2130                2135                2140 cac aca gac aaa gta cca gga gat gag gat aaa ggc atc aac gtg      6672
His Thr Asp Lys Val Pro Gly Asp Glu Asp Lys Gly Ile Asn Val
2145                2150                2155 ttc agg gaa act gca aaa cag aaa ctg gac cca gca gca agt gta      6717
Phe Arg Glu Thr Ala Lys Gln Lys Leu Asp Pro Ala Ala Ser Val
2160                2165                2170 act ggt agc aag agg cag cca aga act cct aag gga aaa gcc caa      6762
Thr Gly Ser Lys Arg Gln Pro Arg Thr Pro Lys Gly Lys Ala Gln
2175                2180                2185 ccc cta gaa gac ttg gct ggc ttg aaa gag ctc ttc cag aca cca      6807
Pro Leu Glu Asp Leu Ala Gly Leu Lys Glu Leu Phe Gln Thr Pro
2190                2195                2200 ata tgc act gac aag ccc acg act cat gag aaa act acc aaa ata      6852
Ile Cys Thr Asp Lys Pro Thr Thr His Glu Lys Thr Thr Lys Ile
2205                2210                2215 gcc tgc aga tct cca caa cca gac cca gtg ggt acc cca aca atc      6897
Ala Cys Arg Ser Pro Gln Pro Asp Pro Val Gly Thr Pro Thr Ile
2220                2225                2230 ttc aag cca cag tcc aag aga agt ctc agg aaa gca gac gta gag      6942
Phe Lys Pro Gln Ser Lys Arg Ser Leu Arg Lys Ala Asp Val Glu
2235                2240                2245 gaa gaa tcc tta gca ctc agg aaa cga aca cca tca gta ggg aaa      6987
Glu Glu Ser Leu Ala Leu Arg Lys Arg Thr Pro Ser Val Gly Lys
2250                2255                2260 gct atg gac aca ccc aaa cca gca gga ggt gat gag aaa gac atg      7032
Ala Met Asp Thr Pro Lys Pro Ala Gly Gly Asp Glu Lys Asp Met
2265                2270                2275 aaa gca ttt atg gga act cca gtg cag aaa ttg gac ctg cca gga      7077
Lys Ala Phe Met Gly Thr Pro Val Gln Lys Leu Asp Leu Pro Gly
2280                2285                2290 aat tta cct ggc agc aaa aga tgg cca caa act cct aag gaa aag      7122
Asn Leu Pro Gly Ser Lys Arg Trp Pro Gln Thr Pro Lys Glu Lys
2295                2300                2305 gcc cag gct cta gaa gac ctg gct ggc ttc aaa gag ctc ttc cag      7167
Ala Gln Ala Leu Glu Asp Leu Ala Gly Phe Lys Glu Leu Phe Gln
2310                2315                2320 aca cca ggc act gac aag ccc acg act gat gag aaa act acc aaa      7212
Thr Pro Gly Thr Asp Lys Pro Thr Thr Asp Glu Lys Thr Thr Lys
2325                2330                2335 ata gcc tgc aaa tct cca caa cca gac cca gtg gac acc cca gca      7257
Ile Ala Cys Lys Ser Pro Gln Pro Asp Pro Val Asp Thr Pro Ala
2340                2345                2350 agc aca aag caa cgg ccc aag aga aac ctc agg aaa gca gac gta      7302
Ser Thr Lys Gln Arg Pro Lys Arg Asn Leu Arg Lys Ala Asp Val
2355                2360                2365 gag gaa gaa ttt tta gca ctc agg aaa cga aca cca tca gca ggc      7347
Glu Glu Glu Phe Leu Ala Leu Arg Lys Arg Thr Pro Ser Ala Gly
2370                2375                2380 aaa gcc atg gac aca cca aaa cca gca gta agt gat gag aaa aat      7392
Lys Ala Met Asp Thr Pro Lys Pro Ala Val Ser Asp Glu Lys Asn
2385                2390                2395
```

| | | | | | | | | | | | | | | |
|---|---|---|---|---|---|---|---|---|---|---|---|---|---|---|
| atc | aac | aca | ttt | gtg | gaa | act | cca | gtg | cag | aaa | ctg | gac | ctg | cta | 7437 |
| Ile | Asn | Thr | Phe | Val | Glu | Thr | Pro | Val | Gln | Lys | Leu | Asp | Leu | Leu | |
| 2400 | | | | 2405 | | | | | 2410 | | | | | | |
| gga | aat | tta | cct | ggc | agc | aag | aga | cag | cca | cag | act | cct | aag | gaa | 7482 |
| Gly | Asn | Leu | Pro | Gly | Ser | Lys | Arg | Gln | Pro | Gln | Thr | Pro | Lys | Glu | |
| 2415 | | | | 2420 | | | | | 2425 | | | | | | |
| aag | gct | gag | gct | cta | gag | gac | ctg | gtt | ggc | ttc | aaa | gaa | ctc | ttc | 7527 |
| Lys | Ala | Glu | Ala | Leu | Glu | Asp | Leu | Val | Gly | Phe | Lys | Glu | Leu | Phe | |
| 2430 | | | | 2435 | | | | | 2440 | | | | | | |
| cag | aca | cca | ggt | cac | act | gag | gaa | tca | atg | act | gat | gac | aaa | atc | 7572 |
| Gln | Thr | Pro | Gly | His | Thr | Glu | Glu | Ser | Met | Thr | Asp | Asp | Lys | Ile | |
| 2445 | | | | 2450 | | | | | 2455 | | | | | | |
| aca | gaa | gta | tcc | tgt | aaa | tct | cca | cag | cca | gag | tca | ttc | aaa | acc | 7617 |
| Thr | Glu | Val | Ser | Cys | Lys | Ser | Pro | Gln | Pro | Glu | Ser | Phe | Lys | Thr | |
| 2460 | | | | 2465 | | | | | 2470 | | | | | | |
| tca | aga | agc | tcc | aag | caa | agg | ctc | aag | ata | ccc | ctg | gtg | aaa | gtg | 7662 |
| Ser | Arg | Ser | Ser | Lys | Gln | Arg | Leu | Lys | Ile | Pro | Leu | Val | Lys | Val | |
| 2475 | | | | 2480 | | | | | 2485 | | | | | | |
| gac | atg | aaa | gaa | gag | ccc | cta | gca | gtc | agc | aag | ctc | aca | cgg | aca | 7707 |
| Asp | Met | Lys | Glu | Glu | Pro | Leu | Ala | Val | Ser | Lys | Leu | Thr | Arg | Thr | |
| 2490 | | | | 2495 | | | | | 2500 | | | | | | |
| tca | ggg | gag | act | acg | caa | aca | cac | aca | gag | cca | aca | gga | gat | agt | 7752 |
| Ser | Gly | Glu | Thr | Thr | Gln | Thr | His | Thr | Glu | Pro | Thr | Gly | Asp | Ser | |
| 2505 | | | | 2510 | | | | | 2515 | | | | | | |
| aag | agc | atc | aaa | gcg | ttt | aag | gag | tct | cca | aag | cag | atc | ctg | gac | 7797 |
| Lys | Ser | Ile | Lys | Ala | Phe | Lys | Glu | Ser | Pro | Lys | Gln | Ile | Leu | Asp | |
| 2520 | | | | 2525 | | | | | 2530 | | | | | | |
| cca | gca | gca | agt | gta | act | ggt | agc | agg | agg | cag | ctg | aga | act | cgt | 7842 |
| Pro | Ala | Ala | Ser | Val | Thr | Gly | Ser | Arg | Arg | Gln | Leu | Arg | Thr | Arg | |
| 2535 | | | | 2540 | | | | | 2545 | | | | | | |
| aag | gaa | aag | gcc | cgt | gct | cta | gaa | gac | ctg | gtt | gac | ttc | aaa | gag | 7887 |
| Lys | Glu | Lys | Ala | Arg | Ala | Leu | Glu | Asp | Leu | Val | Asp | Phe | Lys | Glu | |
| 2550 | | | | 2555 | | | | | 2560 | | | | | | |
| ctc | ttc | tca | gca | cca | ggt | cac | act | gaa | gag | tca | atg | act | att | gac | 7932 |
| Leu | Phe | Ser | Ala | Pro | Gly | His | Thr | Glu | Glu | Ser | Met | Thr | Ile | Asp | |
| 2565 | | | | 2570 | | | | | 2575 | | | | | | |
| aaa | aac | aca | aaa | att | ccc | tgc | aaa | tct | ccc | cca | gaa | cta | aca | 7977 |
| Lys | Asn | Thr | Lys | Ile | Pro | Cys | Lys | Ser | Pro | Pro | Glu | Leu | Thr | |
| 2580 | | | | 2585 | | | | | 2590 | | | | | | |
| gac | act | gcc | acg | agc | aca | aag | aga | tgc | ccc | aag | aca | cgt | ccc | agg | 8022 |
| Asp | Thr | Ala | Thr | Ser | Thr | Lys | Arg | Cys | Pro | Lys | Thr | Arg | Pro | Arg | |
| 2595 | | | | 2600 | | | | | 2605 | | | | | | |
| aaa | gaa | gta | aaa | gag | gag | ctc | tca | gca | gtt | gag | agg | ctc | acg | caa | 8067 |
| Lys | Glu | Val | Lys | Glu | Glu | Leu | Ser | Ala | Val | Glu | Arg | Leu | Thr | Gln | |
| 2610 | | | | 2615 | | | | | 2620 | | | | | | |
| aca | tca | ggg | caa | agc | aca | cac | aca | cac | aaa | gaa | cca | gca | agc | ggt | 8112 |
| Thr | Ser | Gly | Gln | Ser | Thr | His | Thr | His | Lys | Glu | Pro | Ala | Ser | Gly | |
| 2625 | | | | 2630 | | | | | 2635 | | | | | | |
| gat | gag | ggc | atc | aaa | gta | ttg | aag | caa | cgt | gca | aag | aag | aaa | cca | 8157 |
| Asp | Glu | Gly | Ile | Lys | Val | Leu | Lys | Gln | Arg | Ala | Lys | Lys | Lys | Pro | |
| 2640 | | | | 2645 | | | | | 2650 | | | | | | |
| aac | cca | gta | gaa | gag | gaa | ccc | agc | agg | aga | agg | cca | aga | gca | cct | 8202 |
| Asn | Pro | Val | Glu | Glu | Glu | Pro | Ser | Arg | Arg | Arg | Pro | Arg | Ala | Pro | |
| 2655 | | | | 2660 | | | | | 2665 | | | | | | |
| aag | gaa | aag | gcc | caa | ccc | ctg | gaa | gac | ctg | gcc | ggc | ttc | aca | gag | 8247 |
| Lys | Glu | Lys | Ala | Gln | Pro | Leu | Glu | Asp | Leu | Ala | Gly | Phe | Thr | Glu | |
| 2670 | | | | 2675 | | | | | 2680 | | | | | | |
| ctc | tct | gaa | aca | tca | ggt | cac | act | cag | gaa | tca | ctg | act | gct | ggc | 8292 |
| Leu | Ser | Glu | Thr | Ser | Gly | His | Thr | Gln | Glu | Ser | Leu | Thr | Ala | Gly | |

-continued

| | | | | |
|---|---|---|---|---|
| 2685 | | 2690 | | 2695 |
| aaa gcc act aaa ata ccc tgc gaa tct ccc cca cta gaa gtg gta<br>Lys Ala Thr Lys Ile Pro Cys Glu Ser Pro Pro Leu Glu Val Val<br>2700                          2705                          2710 | | | | 8337 |
| gac acc aca gca agc aca aag agg cat ctc agg aca cgt gtg cag<br>Asp Thr Thr Ala Ser Thr Lys Arg His Leu Arg Thr Arg Val Gln<br>2715                          2720                          2725 | | | | 8382 |
| aag gta caa gta aaa gaa gag cct tca gca gtc aag ttc aca caa<br>Lys Val Gln Val Lys Glu Glu Pro Ser Ala Val Lys Phe Thr Gln<br>2730                          2735                          2740 | | | | 8427 |
| aca tca ggg gaa acc acg gat gca gac aaa gaa cca gca ggt gaa<br>Thr Ser Gly Glu Thr Thr Asp Ala Asp Lys Glu Pro Ala Gly Glu<br>2745                          2750                          2755 | | | | 8472 |
| gat aaa ggc atc aaa gca ttg aag gaa tct gca aaa cag aca ccg<br>Asp Lys Gly Ile Lys Ala Leu Lys Glu Ser Ala Lys Gln Thr Pro<br>2760                          2765                          2770 | | | | 8517 |
| gct cca gca gca agt gta act ggc agc agg aga cgg cca aga gca<br>Ala Pro Ala Ala Ser Val Thr Gly Ser Arg Arg Arg Pro Arg Ala<br>2775                          2780                          2785 | | | | 8562 |
| ccc agg gaa agt gcc caa gcc ata gaa gac cta gct ggc ttc aaa<br>Pro Arg Glu Ser Ala Gln Ala Ile Glu Asp Leu Ala Gly Phe Lys<br>2790                          2795                          2800 | | | | 8607 |
| gac cca gca gca ggt cac act gaa gaa tca atg act gat gac aaa<br>Asp Pro Ala Ala Gly His Thr Glu Glu Ser Met Thr Asp Asp Lys<br>2805                          2810                          2815 | | | | 8652 |
| acc act aaa ata ccc tgc aaa tca tca cca gaa cta gaa gac acc<br>Thr Thr Lys Ile Pro Cys Lys Ser Ser Pro Glu Leu Glu Asp Thr<br>2820                          2825                          2830 | | | | 8697 |
| gca aca agc tca aag aga cgg ccc agg aca cgt gcc cag aaa gta<br>Ala Thr Ser Ser Lys Arg Arg Pro Arg Thr Arg Ala Gln Lys Val<br>2835                          2840                          2845 | | | | 8742 |
| gaa gtg aag gag gag ctg tta gca gtt ggc aag ctc aca caa acc<br>Glu Val Lys Glu Glu Leu Leu Ala Val Gly Lys Leu Thr Gln Thr<br>2850                          2855                          2860 | | | | 8787 |
| tca ggg gag acc acg cac acc gac aaa gag ccg gta ggt gag ggc<br>Ser Gly Glu Thr Thr His Thr Asp Lys Glu Pro Val Gly Glu Gly<br>2865                          2870                          2875 | | | | 8832 |
| aaa ggc acg aaa gca ttt aag caa cct gca aag cgg aag ctg gac<br>Lys Gly Thr Lys Ala Phe Lys Gln Pro Ala Lys Arg Lys Leu Asp<br>2880                          2885                          2890 | | | | 8877 |
| gca gaa gat gta att ggc agc agg aga cag cca aga gca cct aag<br>Ala Glu Asp Val Ile Gly Ser Arg Arg Gln Pro Arg Ala Pro Lys<br>2895                          2900                          2905 | | | | 8922 |
| gaa aag gcc caa ccc ctg gaa gat ctg gcc agc ttc caa gag ctc<br>Glu Lys Ala Gln Pro Leu Glu Asp Leu Ala Ser Phe Gln Glu Leu<br>2910                          2915                          2920 | | | | 8967 |
| tct caa aca cca ggc cac act gag gaa ctg gca aat ggt gct gct<br>Ser Gln Thr Pro Gly His Thr Glu Glu Leu Ala Asn Gly Ala Ala<br>2925                          2930                          2935 | | | | 9012 |
| gat agc ttt aca agc gct cca aag caa aca cct gac agt gga aaa<br>Asp Ser Phe Thr Ser Ala Pro Lys Gln Thr Pro Asp Ser Gly Lys<br>2940                          2945                          2950 | | | | 9057 |
| cct cta aaa ata tcc aga aga gtt ctt cgg gcc cct aaa gta gaa<br>Pro Leu Lys Ile Ser Arg Arg Val Leu Arg Ala Pro Lys Val Glu<br>2955                          2960                          2965 | | | | 9102 |
| ccc gtg gga gac gtg gta agc acc aga gac cct gta aaa tca caa<br>Pro Val Gly Asp Val Val Ser Thr Arg Asp Pro Val Lys Ser Gln<br>2970                          2975                          2980 | | | | 9147 |
| agc aaa agc aac act tcc ctg ccc cca ctg ccc ttc aag agg gga | | | | 9192 |

```
Ser Lys Ser Asn Thr Ser Leu Pro Pro Leu Pro Phe Lys Arg Gly
2985                2990                2995 ggt ggc aaa gat gga agc gtc acg gga acc aag agg ctg cgc tgc    9237
Gly Gly Lys Asp Gly Ser Val Thr Gly Thr Lys Arg Leu Arg Cys
3000                3005                3010 atg cca gca cca gag gaa att gtg gag gag ctg cca gcc agc aag    9282
Met Pro Ala Pro Glu Glu Ile Val Glu Glu Leu Pro Ala Ser Lys
3015                3020                3025 aag cag agg gtt gct ccc agg gca aga ggc aaa tca tcc gaa ccc    9327
Lys Gln Arg Val Ala Pro Arg Ala Arg Gly Lys Ser Ser Glu Pro
3030                3035                3040 gtg gtc atc atg aag aga agt ttg agg act tct gca aaa aga att    9372
Val Val Ile Met Lys Arg Ser Leu Arg Thr Ser Ala Lys Arg Ile
3045                3050                3055 gaa cct gcg gaa gag ctg aac agc aac gac atg aaa acc aac aaa    9417
Glu Pro Ala Glu Glu Leu Asn Ser Asn Asp Met Lys Thr Asn Lys
3060                3065                3070 gag gaa cac aaa tta caa gac tcg gtc cct gaa aat aag gga ata    9462
Glu Glu His Lys Leu Gln Asp Ser Val Pro Glu Asn Lys Gly Ile
3075                3080                3085 tcc ctg cgc tcc aga cgc caa aat aag act gag gca gaa cag caa    9507
Ser Leu Arg Ser Arg Arg Gln Asn Lys Thr Glu Ala Glu Gln Gln
3090                3095                3100 ata act gag gtc ttt gta tta gca gaa aga ata gaa ata aac aga    9552
Ile Thr Glu Val Phe Val Leu Ala Glu Arg Ile Glu Ile Asn Arg
3105                3110                3115 aat gaa aag aag ccc atg aag acc tcc cca gag atg gac att cag    9597
Asn Glu Lys Lys Pro Met Lys Thr Ser Pro Glu Met Asp Ile Gln
3120                3125                3130 aat cca gat gat gga gcc cgg aaa ccc ata cct aga gac aaa gtc    9642
Asn Pro Asp Asp Gly Ala Arg Lys Pro Ile Pro Arg Asp Lys Val
3135                3140                3145 act gag aac aaa agg tgc ttg agg tct gct aga cag aat gag agc    9687
Thr Glu Asn Lys Arg Cys Leu Arg Ser Ala Arg Gln Asn Glu Ser
3150                3155                3160 tcc cag cct aag gtg gca gag gag agc gga ggg cag aag agt gcg    9732
Ser Gln Pro Lys Val Ala Glu Glu Ser Gly Gly Gln Lys Ser Ala
3165                3170                3175 aag gtt ctc atg cag aat cag aaa ggg aaa gga gaa gca gga aat    9777
Lys Val Leu Met Gln Asn Gln Lys Gly Lys Gly Glu Ala Gly Asn
3180                3185                3190 tca gac tcc atg tgc ctg aga tca aga aag aca aaa agc cag cct    9822
Ser Asp Ser Met Cys Leu Arg Ser Arg Lys Thr Lys Ser Gln Pro
3195                3200                3205 gca gca agc act ttg gag agc aaa tct gtg cag aga gta acg cgg    9867
Ala Ala Ser Thr Leu Glu Ser Lys Ser Val Gln Arg Val Thr Arg
3210                3215                3220 agt gtc aag agg tgt gca gaa aat cca aag aag gct gag gac aat    9912
Ser Val Lys Arg Cys Ala Glu Asn Pro Lys Lys Ala Glu Asp Asn
3225                3230                3235 gtg tgt gtc aag aaa ata aga acc aga agt cat agg gac agt gaa    9957
Val Cys Val Lys Lys Ile Arg Thr Arg Ser His Arg Asp Ser Glu
3240                3245                3250 gat att tga cagaaaaatc gaactgggaa aaatataata aagttagttt       10006
Asp Ile
3255 tgtgataagt tctagtgcag tttttgtcat aaattacaag tgaattctgt aagtaaggct 10066 gtcagtctgc ttaagggaag aaaactttgg atttgctggg tctgaatcgg cttcataaac 10126
```

```
tccactggga gcactgctgg gctcctggac tgagaatagt tgaacaccgg gggctttgtg    10186
aaggagtctg ggccaaggtt tgccctcagc tttgcagaat gaagccttga ggtctgtcac    10246
cacccacagc caccctacag cagccttaac tgtgacactt gccacactgt gtcgtcgttt    10306
gtttgcctat gtcctccagg gcacggtggc aggaacaact atcctcgtct gtcccaacac    10366
tgagcaggca ctcggtaaac acgaatgaat ggatgagcgc acggatgaat ggagcttaca    10426
agatctgtct ttccaatggc cgggggcatt tggtccccaa attaaggcta ttggacatct    10486
gcacaggaca gtcctatttt tgatgtcctt tcctttctga aaataaagtt ttgtgctttg    10546
gagaatgact cgtgagcaca tctttaggga ccaagagtga ctttctgtaa ggagtgactc    10606
gtggcttgcc ttggtctctt gggaatactt ttctaactag ggttgctctc acctgagaca    10666
ttctccaccc gcggaatctc agggtcccag gctgtgggcc atcacgacct caaactggct    10726
cctaatctcc agctttcctg tcattgaaag cttcggaagt ttactggctc tgctcccgcc    10786
tgttttcttt ctgactctat ctggcagccc gatgccaccc agtacaggaa gtgacaccag    10846
tactctgtaa agcatcatca tccttggaga gactgagcac tcagcacctt cagccacgat    10906
ttcaggatcg cttccttgtg agccgctgcc tccgaaatct cctttgaagc ccagacatct    10966
ttctccagct tcagacttgt agatataact cgttcatctt catttacttt ccactttgcc    11026
ccctgtcctc tctgtgttcc ccaaatcaga aatagcccg ccatccccca ggtcacctgt    11086
ctggattcct ccccattcac ccaccttgcc aggtgcaggt gaggatggtg caccagacag    11146
ggtagctgtc ccccaaaatg tgccctgtgc gggcagtgcc ctgtctccac gtttgtttcc    11206
ccagtgtctg gcggggagcc aggtgacatc ataaatactt gctgaatgaa tgcagaaatc    11266
agcggtactg acttgtacta tattggctgc catgataggg ttctcacagc gtcatccatg    11326
atcgtaaggg agaatgacat tctgcttgag ggagggaata gaaagggca gggaggggac    11386
atctgagggc ttcacagggc tgcaaagggt acagggattg caccagggca gaacagggga    11446
gggtgttcaa ggaagagtgg ctcttagcag aggcactttg gaaggtgtga ggcataaatg    11506
cttccttcta cgtaggccaa cctcaaaact ttcagtagga atgttgctat gatcaagttg    11566
ttctaacact ttagacttag tagtaattat gaacctcaca tagaaaaatt tcatccagcc    11626
atatgcctgt ggagtggaat attctgttta gtagaaaaat cctttagagt tcagctctaa    11686
ccagaaatct tgctgaagta tgtcagcacc ttttctcacc ctggtaagta cagtatttca    11746
agagcacgct aagggtggtt ttcattttac agggctgttg atgatgggtt aaaaatgttc    11806
atttaagggc taccccgtg tttaatagat gaacaccact tctacacaac cctccttggt    11866
actgggggag ggagagatct gacaaatact gcccattccc ctaggctgac tggatttgag    11926
aacaaatacc cacccattc caccatggta tggtaacttc tctgagcttc agtttccaag    11986
tgaatttcca tgtaatagga cattcccatt aaatacaagc tgttttact ttttcgcctc    12046
ccagggcctg tgggatctgg tcccccagcc tctcttgggc tttcttacac taactctgta    12106
cctaccatct cctgcctccc ttaggcaggc acctccaacc accacacact ccctgctgtt    12166
ttccctgcct ggaactttcc ctcctgcccc accaagatca tttcatccag tcctgagctc    12226
agcttaaggg aggcttcttg cctgtgggtt ccctcacccc catgcctgtc ctccaggctg    12286
gggcaggttc ttagtttgcc tggaattgtt ctgtacctct ttgtagcacg tagtgttgtg    12346
gaaactaagc cactaattga gtttctggct ccccctcctgg ggttgtaagt tttgttcatt    12406
catgagggcc gactgcattt cctggttact ctatcccagt gaccagccac aggagatgtc    12466
caataaagta tgtgatgaaa tggtcttaaa aaaaaaaaa a    12507
```

<210> SEQ ID NO 66
<211> LENGTH: 3256
<212> TYPE: PRT
<213> ORGANISM: Homo sapiens

<400> SEQUENCE: 66

```
Met Trp Pro Thr Arg Arg Leu Val Thr Ile Lys Arg Ser Gly Val Asp
1               5                   10                  15

Gly Pro His Phe Pro Leu Ser Leu Ser Thr Cys Leu Phe Gly Arg Gly
                20                  25                  30

Ile Glu Cys Asp Ile Arg Ile Gln Leu Pro Val Val Ser Lys Gln His
            35                  40                  45

Cys Lys Ile Glu Ile His Glu Gln Glu Ala Ile Leu His Asn Phe Ser
    50                  55                  60

Ser Thr Asn Pro Thr Gln Val Asn Gly Ser Val Ile Asp Glu Pro Val
65                  70                  75                  80

Arg Leu Lys His Gly Asp Val Ile Thr Ile Ile Asp Arg Ser Phe Arg
                85                  90                  95

Tyr Glu Asn Glu Ser Leu Gln Asn Gly Arg Lys Ser Thr Glu Phe Pro
            100                 105                 110

Arg Lys Ile Arg Glu Gln Glu Pro Ala Arg Arg Val Ser Arg Ser Ser
        115                 120                 125

Phe Ser Ser Asp Pro Asp Glu Lys Ala Gln Asp Ser Lys Ala Tyr Ser
130                 135                 140

Lys Ile Thr Glu Gly Lys Val Ser Gly Asn Pro Gln Val His Ile Lys
145                 150                 155                 160

Asn Val Lys Glu Asp Ser Thr Ala Asp Asp Ser Lys Asp Ser Val Ala
                165                 170                 175

Gln Gly Thr Thr Asn Val His Ser Ser Glu His Ala Gly Arg Asn Gly
            180                 185                 190

Arg Asn Ala Ala Asp Pro Ile Ser Gly Asp Phe Lys Glu Ile Ser Ser
        195                 200                 205

Val Lys Leu Val Ser Arg Tyr Gly Glu Leu Lys Ser Val Pro Thr Thr
    210                 215                 220

Gln Cys Leu Asp Asn Ser Lys Lys Asn Glu Ser Pro Phe Trp Lys Leu
225                 230                 235                 240

Tyr Glu Ser Val Lys Lys Glu Leu Asp Val Lys Ser Gln Lys Glu Asn
                245                 250                 255

Val Leu Gln Tyr Cys Arg Lys Ser Gly Leu Gln Thr Asp Tyr Ala Thr
            260                 265                 270

Glu Lys Glu Ser Ala Asp Gly Leu Gln Gly Glu Thr Gln Leu Leu Val
        275                 280                 285

Ser Arg Lys Ser Arg Pro Lys Ser Gly Gly Ser Gly His Ala Val Ala
    290                 295                 300

Glu Pro Ala Ser Pro Glu Gln Glu Leu Asp Gln Asn Lys Gly Lys Gly
305                 310                 315                 320

Arg Asp Val Glu Ser Val Gln Thr Pro Ser Lys Ala Val Gly Ala Ser
                325                 330                 335

Phe Pro Leu Tyr Glu Pro Ala Lys Met Lys Thr Pro Val Gln Tyr Ser
            340                 345                 350

Gln Gln Gln Asn Ser Pro Gln Lys His Lys Asn Lys Asp Leu Tyr Thr
        355                 360                 365

Thr Gly Arg Arg Glu Ser Val Asn Leu Gly Lys Ser Glu Gly Phe Lys
```

-continued

```
                370                 375                 380
Ala Gly Asp Lys Thr Leu Thr Pro Arg Lys Leu Ser Thr Arg Asn Arg
385                 390                 395                 400

Thr Pro Ala Lys Val Glu Asp Ala Ala Asp Ser Ala Thr Lys Pro Glu
                405                 410                 415

Asn Leu Ser Ser Lys Thr Arg Gly Ser Ile Pro Thr Asp Val Glu Val
                420                 425                 430

Leu Pro Thr Glu Thr Glu Ile His Asn Glu Pro Phe Leu Thr Leu Trp
                435                 440                 445

Leu Thr Gln Val Glu Arg Lys Ile Gln Lys Asp Ser Leu Ser Lys Pro
450                 455                 460

Glu Lys Leu Gly Thr Thr Ala Gly Gln Met Cys Ser Gly Leu Pro Gly
465                 470                 475                 480

Leu Ser Ser Val Asp Ile Asn Asn Phe Gly Asp Ser Ile Asn Glu Ser
                485                 490                 495

Glu Gly Ile Pro Leu Lys Arg Arg Val Ser Phe Gly Gly His Leu
                500                 505                 510

Arg Pro Glu Leu Phe Asp Glu Asn Leu Pro Pro Asn Thr Pro Leu Lys
                515                 520                 525

Arg Gly Glu Ala Pro Thr Lys Arg Lys Ser Leu Val Met His Thr Pro
530                 535                 540

Pro Val Leu Lys Lys Ile Ile Lys Glu Gln Pro Gln Pro Ser Gly Lys
545                 550                 555                 560

Gln Glu Ser Gly Ser Glu Ile His Val Glu Val Lys Ala Gln Ser Leu
                565                 570                 575

Val Ile Ser Pro Pro Ala Pro Ser Pro Arg Lys Thr Pro Val Ala Ser
                580                 585                 590

Asp Gln Arg Arg Arg Ser Cys Lys Thr Ala Pro Ala Ser Ser Ser Lys
                595                 600                 605

Ser Gln Thr Glu Val Pro Lys Arg Gly Gly Arg Lys Ser Gly Asn Leu
                610                 615                 620

Pro Ser Lys Arg Val Ser Ile Ser Arg Ser Gln His Asp Ile Leu Gln
625                 630                 635                 640

Met Ile Cys Ser Lys Arg Arg Ser Gly Ala Ser Glu Ala Asn Leu Ile
                645                 650                 655

Val Ala Lys Ser Trp Ala Asp Val Val Lys Leu Gly Ala Lys Gln Thr
                660                 665                 670

Gln Thr Lys Val Ile Lys His Gly Pro Gln Arg Ser Met Asn Lys Arg
                675                 680                 685

Gln Arg Arg Pro Ala Thr Pro Lys Lys Pro Val Gly Glu Val His Ser
690                 695                 700

Gln Phe Ser Thr Gly His Ala Asn Ser Pro Cys Thr Ile Ile Gly
705                 710                 715                 720

Lys Ala His Thr Glu Lys Val His Val Pro Ala Arg Pro Tyr Arg Val
                725                 730                 735

Leu Asn Asn Phe Ile Ser Asn Gln Lys Met Asp Phe Lys Glu Asp Leu
                740                 745                 750

Ser Gly Ile Ala Glu Met Phe Lys Thr Pro Val Lys Glu Gln Pro Gln
                755                 760                 765

Leu Thr Ser Thr Cys His Ile Ala Ile Ser Asn Ser Glu Asn Leu Leu
                770                 775                 780

Gly Lys Gln Phe Gln Gly Thr Asp Ser Gly Glu Glu Pro Leu Leu Pro
785                 790                 795                 800
```

-continued

```
Thr Ser Glu Ser Phe Gly Gly Asn Val Phe Ser Ala Gln Asn Ala
            805                 810                 815

Ala Lys Gln Pro Ser Asp Lys Cys Ser Ala Ser Pro Pro Leu Arg Arg
            820                 825                 830

Gln Cys Ile Arg Glu Asn Gly Asn Val Ala Lys Thr Pro Arg Asn Thr
            835                 840                 845

Tyr Lys Met Thr Ser Leu Glu Thr Lys Thr Ser Asp Thr Glu Thr Glu
            850                 855                 860

Pro Ser Lys Thr Val Ser Thr Ala Asn Arg Ser Gly Arg Ser Thr Glu
865                 870                 875                 880

Phe Arg Asn Ile Gln Lys Leu Pro Val Glu Ser Lys Ser Glu Glu Thr
            885                 890                 895

Asn Thr Glu Ile Val Glu Cys Ile Leu Lys Arg Gly Gln Lys Ala Thr
            900                 905                 910

Leu Leu Gln Gln Arg Arg Glu Gly Glu Met Lys Glu Ile Glu Arg Pro
            915                 920                 925

Phe Glu Thr Tyr Lys Glu Asn Ile Glu Leu Lys Glu Asn Asp Glu Lys
            930                 935                 940

Met Lys Ala Met Lys Arg Ser Arg Thr Trp Gly Gln Lys Cys Ala Pro
945                 950                 955                 960

Met Ser Asp Leu Thr Asp Leu Lys Ser Leu Pro Asp Thr Glu Leu Met
            965                 970                 975

Lys Asp Thr Ala Arg Gly Gln Asn Leu Leu Gln Thr Gln Asp His Ala
            980                 985                 990

Lys Ala Pro Lys Ser Glu Lys Gly Lys Ile Thr Lys Met Pro Cys Gln
            995                1000                1005

Ser Leu Gln Pro Glu Pro Ile Asn Thr Pro Thr His Thr Lys Gln
       1010                1015                1020

Gln Leu Lys Ala Ser Leu Gly Lys Val Gly Val Lys Glu Glu Leu
       1025                1030                1035

Leu Ala Val Gly Lys Phe Thr Arg Thr Ser Gly Glu Thr Thr His
       1040                1045                1050

Thr His Arg Glu Pro Ala Gly Asp Gly Lys Ser Ile Arg Thr Phe
       1055                1060                1065

Lys Glu Ser Pro Lys Gln Ile Leu Asp Pro Ala Ala Arg Val Thr
       1070                1075                1080

Gly Met Lys Lys Trp Pro Arg Thr Pro Lys Glu Glu Ala Gln Ser
       1085                1090                1095

Leu Glu Asp Leu Ala Gly Phe Lys Glu Leu Phe Gln Thr Pro Gly
       1100                1105                1110

Pro Ser Glu Glu Ser Met Thr Asp Glu Lys Thr Thr Lys Ile Ala
       1115                1120                1125

Cys Lys Ser Pro Pro Glu Ser Val Asp Thr Pro Thr Ser Thr
       1130                1135                1140

Lys Gln Trp Pro Lys Arg Ser Leu Arg Lys Ala Asp Val Glu Glu
       1145                1150                1155

Glu Phe Leu Ala Leu Arg Lys Leu Thr Pro Ser Ala Gly Lys Ala
       1160                1165                1170

Met Leu Thr Pro Lys Pro Ala Gly Gly Asp Glu Lys Asp Ile Lys
       1175                1180                1185

Ala Phe Met Gly Thr Pro Val Gln Lys Leu Asp Leu Ala Gly Thr
       1190                1195                1200
```

```
Leu Pro Gly Ser Lys Arg Gln Leu Gln Thr Pro Lys Glu Lys Ala
    1205                1210                1215

Gln Ala Leu Glu Asp Leu Ala Gly Phe Lys Glu Leu Phe Gln Thr
    1220                1225                1230

Pro Gly His Thr Glu Glu Leu Val Ala Ala Gly Lys Thr Thr Lys
    1235                1240                1245

Ile Pro Cys Asp Ser Pro Gln Ser Asp Pro Val Asp Thr Pro Thr
    1250                1255                1260

Ser Thr Lys Gln Arg Pro Lys Arg Ser Ile Arg Lys Ala Asp Val
    1265                1270                1275

Glu Gly Glu Leu Leu Ala Cys Arg Asn Leu Met Pro Ser Ala Gly
    1280                1285                1290

Lys Ala Met His Thr Pro Lys Pro Ser Val Gly Glu Glu Lys Asp
    1295                1300                1305

Ile Ile Ile Phe Val Gly Thr Pro Val Gln Lys Leu Asp Leu Thr
    1310                1315                1320

Glu Asn Leu Thr Gly Ser Lys Arg Arg Pro Gln Thr Pro Lys Glu
    1325                1330                1335

Glu Ala Gln Ala Leu Glu Asp Leu Thr Gly Phe Lys Glu Leu Phe
    1340                1345                1350

Gln Thr Pro Gly His Thr Glu Glu Ala Val Ala Ala Gly Lys Thr
    1355                1360                1365

Thr Lys Met Pro Cys Glu Ser Ser Pro Pro Glu Ser Ala Asp Thr
    1370                1375                1380

Pro Thr Ser Thr Arg Arg Gln Pro Lys Thr Pro Leu Glu Lys Arg
    1385                1390                1395

Asp Val Gln Lys Glu Leu Ser Ala Leu Lys Lys Leu Thr Gln Thr
    1400                1405                1410

Ser Gly Glu Thr Thr His Thr Asp Lys Val Pro Gly Gly Glu Asp
    1415                1420                1425

Lys Ser Ile Asn Ala Phe Arg Glu Thr Ala Lys Gln Lys Leu Asp
    1430                1435                1440

Pro Ala Ala Ser Val Thr Gly Ser Lys Arg His Pro Lys Thr Lys
    1445                1450                1455

Glu Lys Ala Gln Pro Leu Glu Asp Leu Ala Gly Leu Lys Glu Leu
    1460                1465                1470

Phe Gln Thr Pro Val Cys Thr Asp Lys Pro Thr Thr His Glu Lys
    1475                1480                1485

Thr Thr Lys Ile Ala Cys Arg Ser Gln Pro Asp Pro Val Asp Thr
    1490                1495                1500

Pro Thr Ser Ser Lys Pro Gln Ser Lys Arg Ser Leu Arg Lys Val
    1505                1510                1515

Asp Val Glu Glu Glu Phe Phe Ala Leu Arg Lys Arg Thr Pro Ser
    1520                1525                1530

Ala Gly Lys Ala Met His Thr Pro Lys Pro Ala Val Ser Gly Glu
    1535                1540                1545

Lys Asn Ile Tyr Ala Phe Met Gly Thr Pro Val Gln Lys Leu Asp
    1550                1555                1560

Leu Thr Glu Asn Leu Thr Gly Ser Lys Arg Arg Leu Gln Thr Pro
    1565                1570                1575

Lys Glu Lys Ala Gln Ala Leu Glu Asp Leu Ala Gly Phe Lys Glu
    1580                1585                1590

Leu Phe Gln Thr Arg Gly His Thr Glu Glu Ser Met Thr Asn Asp
```

-continued

```
            1595                1600                1605
Lys Thr Ala Lys Val Ala Cys Lys Ser Ser Gln Pro Asp Pro Asp
            1610                1615                1620
Lys Asn Pro Ala Ser Ser Lys Arg Arg Leu Lys Thr Ser Leu Gly
            1625                1630                1635
Lys Val Gly Val Lys Glu Glu Leu Leu Ala Val Gly Lys Leu Thr
            1640                1645                1650
Gln Thr Ser Gly Glu Thr Thr His Thr His Thr Glu Pro Thr Gly
            1655                1660                1665
Asp Gly Lys Ser Met Lys Ala Phe Met Glu Ser Pro Lys Gln Ile
            1670                1675                1680
Leu Asp Ser Ala Ala Ser Leu Thr Gly Ser Lys Arg Gln Leu Arg
            1685                1690                1695
Thr Pro Lys Gly Lys Ser Glu Val Pro Glu Asp Leu Ala Gly Phe
            1700                1705                1710
Ile Glu Leu Phe Gln Thr Pro Ser His Thr Lys Glu Ser Met Thr
            1715                1720                1725
Asn Glu Lys Thr Thr Lys Val Ser Tyr Arg Ala Ser Gln Pro Asp
            1730                1735                1740
Leu Val Asp Thr Pro Thr Ser Ser Lys Pro Gln Pro Lys Arg Ser
            1745                1750                1755
Leu Arg Lys Ala Asp Thr Glu Glu Glu Phe Leu Ala Phe Arg Lys
            1760                1765                1770
Gln Thr Pro Ser Ala Gly Lys Ala Met His Thr Pro Lys Pro Ala
            1775                1780                1785
Val Gly Glu Glu Lys Asp Ile Asn Thr Phe Leu Gly Thr Pro Val
            1790                1795                1800
Gln Lys Leu Asp Gln Pro Gly Asn Leu Pro Gly Ser Asn Arg Arg
            1805                1810                1815
Leu Gln Thr Arg Lys Glu Lys Ala Gln Ala Leu Glu Glu Leu Thr
            1820                1825                1830
Gly Phe Arg Glu Leu Phe Gln Thr Pro Cys Thr Asp Asn Pro Thr
            1835                1840                1845
Thr Asp Glu Lys Thr Thr Lys Lys Ile Leu Cys Lys Ser Pro Gln
            1850                1855                1860
Ser Asp Pro Ala Asp Thr Pro Thr Asn Thr Lys Gln Arg Pro Lys
            1865                1870                1875
Arg Ser Leu Lys Lys Ala Asp Val Glu Glu Phe Leu Ala Phe
            1880                1885                1890
Arg Lys Leu Thr Pro Ser Ala Gly Lys Ala Met His Thr Pro Lys
            1895                1900                1905
Ala Ala Val Gly Glu Glu Lys Asp Ile Asn Thr Phe Val Gly Thr
            1910                1915                1920
Pro Val Glu Lys Leu Asp Leu Leu Gly Asn Leu Pro Gly Ser Lys
            1925                1930                1935
Arg Arg Pro Gln Thr Pro Lys Glu Lys Ala Lys Ala Leu Glu Asp
            1940                1945                1950
Leu Ala Gly Phe Lys Glu Leu Phe Gln Thr Pro Gly His Thr Glu
            1955                1960                1965
Glu Ser Met Thr Asp Asp Lys Ile Thr Glu Val Ser Cys Lys Ser
            1970                1975                1980
Pro Gln Pro Asp Pro Val Lys Thr Pro Thr Ser Ser Lys Gln Arg
            1985                1990                1995
```

```
Leu Lys Ile Ser Leu Gly Lys Val Gly Val Lys Glu Glu Val Leu
2000                2005                2010

Pro Val Gly Lys Leu Thr Gln Thr Ser Gly Lys Thr Thr Gln Thr
2015                2020                2025

His Arg Glu Thr Ala Gly Asp Gly Lys Ser Ile Lys Ala Phe Lys
2030                2035                2040

Glu Ser Ala Lys Gln Met Leu Asp Pro Ala Asn Tyr Gly Thr Gly
2045                2050                2055

Met Glu Arg Trp Pro Arg Thr Pro Lys Glu Glu Ala Gln Ser Leu
2060                2065                2070

Glu Asp Leu Ala Gly Phe Lys Glu Leu Phe Gln Thr Pro Asp His
2075                2080                2085

Thr Glu Glu Ser Thr Thr Asp Asp Lys Thr Thr Lys Ile Ala Cys
2090                2095                2100

Lys Ser Pro Pro Pro Glu Ser Met Asp Thr Pro Thr Ser Thr Arg
2105                2110                2115

Arg Arg Pro Lys Thr Pro Leu Gly Lys Arg Asp Ile Val Glu Glu
2120                2125                2130

Leu Ser Ala Leu Lys Gln Leu Thr Gln Thr Thr His Thr Asp Lys
2135                2140                2145

Val Pro Gly Asp Glu Asp Lys Gly Ile Asn Val Phe Arg Glu Thr
2150                2155                2160

Ala Lys Gln Lys Leu Asp Pro Ala Ala Ser Val Thr Gly Ser Lys
2165                2170                2175

Arg Gln Pro Arg Thr Pro Lys Gly Lys Ala Gln Pro Leu Glu Asp
2180                2185                2190

Leu Ala Gly Leu Lys Glu Leu Phe Gln Thr Pro Ile Cys Thr Asp
2195                2200                2205

Lys Pro Thr Thr His Glu Lys Thr Thr Lys Ile Ala Cys Arg Ser
2210                2215                2220

Pro Gln Pro Asp Pro Val Gly Thr Pro Thr Ile Phe Lys Pro Gln
2225                2230                2235

Ser Lys Arg Ser Leu Arg Lys Ala Asp Val Glu Glu Ser Leu
2240                2245                2250

Ala Leu Arg Lys Arg Thr Pro Ser Val Gly Lys Ala Met Asp Thr
2255                2260                2265

Pro Lys Pro Ala Gly Gly Asp Glu Lys Asp Met Lys Ala Phe Met
2270                2275                2280

Gly Thr Pro Val Gln Lys Leu Asp Leu Pro Gly Asn Leu Pro Gly
2285                2290                2295

Ser Lys Arg Trp Pro Gln Thr Pro Lys Glu Lys Ala Gln Ala Leu
2300                2305                2310

Glu Asp Leu Ala Gly Phe Lys Glu Leu Phe Gln Thr Pro Gly Thr
2315                2320                2325

Asp Lys Pro Thr Thr Asp Glu Lys Thr Thr Lys Ile Ala Cys Lys
2330                2335                2340

Ser Pro Gln Pro Asp Pro Val Asp Thr Pro Ala Ser Thr Lys Gln
2345                2350                2355

Arg Pro Lys Arg Asn Leu Arg Lys Ala Asp Val Glu Glu Glu Phe
2360                2365                2370

Leu Ala Leu Arg Lys Arg Thr Pro Ser Ala Gly Lys Ala Met Asp
2375                2380                2385
```

```
Thr Pro Lys Pro Ala Val Ser Asp Glu Lys Asn Ile Asn Thr Phe
    2390            2395            2400

Val Glu Thr Pro Val Gln Lys Leu Asp Leu Leu Gly Asn Leu Pro
2405            2410            2415

Gly Ser Lys Arg Gln Pro Gln Thr Pro Lys Glu Lys Ala Glu Ala
2420            2425            2430

Leu Glu Asp Leu Val Gly Phe Lys Glu Leu Phe Gln Thr Pro Gly
2435            2440            2445

His Thr Glu Glu Ser Met Thr Asp Asp Lys Ile Thr Glu Val Ser
    2450            2455            2460

Cys Lys Ser Pro Gln Pro Glu Ser Phe Lys Thr Ser Arg Ser Ser
2465            2470            2475

Lys Gln Arg Leu Lys Ile Pro Leu Val Lys Val Asp Met Lys Glu
    2480            2485            2490

Glu Pro Leu Ala Val Ser Lys Leu Thr Arg Thr Ser Gly Glu Thr
2495            2500            2505

Thr Gln Thr His Thr Glu Pro Thr Gly Asp Ser Lys Ser Ile Lys
    2510            2515            2520

Ala Phe Lys Glu Ser Pro Lys Gln Ile Leu Asp Pro Ala Ala Ser
2525            2530            2535

Val Thr Gly Ser Arg Arg Gln Leu Arg Thr Arg Lys Glu Lys Ala
2540            2545            2550

Arg Ala Leu Glu Asp Leu Val Asp Phe Lys Glu Leu Phe Ser Ala
    2555            2560            2565

Pro Gly His Thr Glu Glu Ser Met Thr Ile Asp Lys Asn Thr Lys
2570            2575            2580

Ile Pro Cys Lys Ser Pro Pro Glu Leu Thr Asp Thr Ala Thr
    2585            2590            2595

Ser Thr Lys Arg Cys Pro Lys Thr Arg Pro Arg Lys Glu Val Lys
2600            2605            2610

Glu Glu Leu Ser Ala Val Glu Arg Leu Thr Gln Thr Ser Gly Gln
    2615            2620            2625

Ser Thr His Thr His Lys Glu Pro Ala Ser Gly Asp Glu Gly Ile
2630            2635            2640

Lys Val Leu Lys Gln Arg Ala Lys Lys Lys Pro Asn Pro Val Glu
2645            2650            2655

Glu Glu Pro Ser Arg Arg Arg Pro Arg Ala Pro Lys Glu Lys Ala
2660            2665            2670

Gln Pro Leu Glu Asp Leu Ala Gly Phe Thr Glu Leu Ser Glu Thr
2675            2680            2685

Ser Gly His Thr Gln Glu Ser Leu Thr Ala Gly Lys Ala Thr Lys
2690            2695            2700

Ile Pro Cys Glu Ser Pro Pro Leu Glu Val Val Asp Thr Thr Ala
2705            2710            2715

Ser Thr Lys Arg His Leu Arg Thr Arg Val Gln Lys Val Gln Val
2720            2725            2730

Lys Glu Glu Pro Ser Ala Val Lys Phe Thr Gln Thr Ser Gly Glu
2735            2740            2745

Thr Thr Asp Ala Asp Lys Glu Pro Ala Gly Glu Asp Lys Gly Ile
2750            2755            2760

Lys Ala Leu Lys Glu Ser Ala Lys Gln Thr Pro Ala Pro Ala Ala
2765            2770            2775

Ser Val Thr Gly Ser Arg Arg Arg Pro Arg Ala Pro Arg Glu Ser
```

```
            2780                2785                2790
Ala Gln Ala Ile Glu Asp Leu Ala Gly Phe Lys Asp Pro Ala Ala
    2795                2800                2805
Gly His Thr Glu Glu Ser Met Thr Asp Asp Lys Thr Thr Lys Ile
    2810                2815                2820
Pro Cys Lys Ser Ser Pro Glu Leu Glu Asp Thr Ala Thr Ser Ser
    2825                2830                2835
Lys Arg Arg Pro Arg Thr Arg Ala Gln Lys Val Glu Val Lys Glu
    2840                2845                2850
Glu Leu Leu Ala Val Gly Lys Leu Thr Gln Thr Ser Gly Glu Thr
    2855                2860                2865
Thr His Thr Asp Lys Glu Pro Val Gly Glu Gly Lys Gly Thr Lys
    2870                2875                2880
Ala Phe Lys Gln Pro Ala Lys Arg Lys Leu Asp Ala Glu Asp Val
    2885                2890                2895
Ile Gly Ser Arg Arg Gln Pro Arg Ala Pro Lys Glu Lys Ala Gln
    2900                2905                2910
Pro Leu Glu Asp Leu Ala Ser Phe Gln Glu Leu Ser Gln Thr Pro
    2915                2920                2925
Gly His Thr Glu Glu Leu Ala Asn Gly Ala Ala Asp Ser Phe Thr
    2930                2935                2940
Ser Ala Pro Lys Gln Thr Pro Asp Ser Gly Lys Pro Leu Lys Ile
    2945                2950                2955
Ser Arg Arg Val Leu Arg Ala Pro Lys Val Glu Pro Val Gly Asp
    2960                2965                2970
Val Val Ser Thr Arg Asp Pro Val Lys Ser Gln Ser Lys Ser Asn
    2975                2980                2985
Thr Ser Leu Pro Pro Leu Pro Phe Lys Arg Gly Gly Gly Lys Asp
    2990                2995                3000
Gly Ser Val Thr Gly Thr Lys Arg Leu Arg Cys Met Pro Ala Pro
    3005                3010                3015
Glu Glu Ile Val Glu Glu Leu Pro Ala Ser Lys Lys Gln Arg Val
    3020                3025                3030
Ala Pro Arg Ala Arg Gly Lys Ser Ser Glu Pro Val Val Ile Met
    3035                3040                3045
Lys Arg Ser Leu Arg Thr Ser Ala Lys Arg Ile Glu Pro Ala Glu
    3050                3055                3060
Glu Leu Asn Ser Asn Asp Met Lys Thr Asn Lys Glu Glu His Lys
    3065                3070                3075
Leu Gln Asp Ser Val Pro Glu Asn Lys Gly Ile Ser Leu Arg Ser
    3080                3085                3090
Arg Arg Gln Asn Lys Thr Glu Ala Glu Gln Ile Thr Glu Val
    3095                3100                3105
Phe Val Leu Ala Glu Arg Ile Glu Ile Asn Arg Asn Glu Lys Lys
    3110                3115                3120
Pro Met Lys Thr Ser Pro Glu Met Asp Ile Gln Asn Pro Asp Asp
    3125                3130                3135
Gly Ala Arg Lys Pro Ile Pro Arg Asp Lys Val Thr Glu Asn Lys
    3140                3145                3150
Arg Cys Leu Arg Ser Ala Arg Gln Asn Glu Ser Ser Gln Pro Lys
    3155                3160                3165
Val Ala Glu Glu Ser Gly Gly Gln Lys Ser Ala Lys Val Leu Met
    3170                3175                3180
```

| | | | | | | | | | | |
|---|---|---|---|---|---|---|---|---|---|---|
| Gln | Asn | Gln | Lys | Gly | Lys | Gly | Glu | Ala | Gly | Asn | Ser | Asp | Ser | Met |
| 3185 | | | | 3190 | | | | | 3195 | | | | | |
| Cys | Leu | Arg | Ser | Arg | Lys | Thr | Lys | Ser | Gln | Pro | Ala | Ala | Ser | Thr |
| 3200 | | | | | 3205 | | | | | 3210 | | | | |
| Leu | Glu | Ser | Lys | Ser | Val | Gln | Arg | Val | Thr | Arg | Ser | Val | Lys | Arg |
| 3215 | | | | | 3220 | | | | | 3225 | | | | |
| Cys | Ala | Glu | Asn | Pro | Lys | Lys | Ala | Glu | Asp | Asn | Val | Cys | Val | Lys |
| 3230 | | | | | 3235 | | | | | 3240 | | | | |
| Lys | Ile | Arg | Thr | Arg | Ser | His | Arg | Asp | Ser | Glu | Asp | Ile | | |
| 3245 | | | | | 3250 | | | | | 3255 | | | | |

```
<210> SEQ ID NO 67
<211> LENGTH: 11427
<212> TYPE: DNA
<213> ORGANISM: Homo sapiens
<220> FEATURE:
<221> NAME/KEY: CDS
<222> LOCATION: (196)..(8886)

<400> SEQUENCE: 67
taccgggcgg aggtgagcgc ggcgccggct cctcctgcgg cggactttgg gtgcgacttg      60
acgagcggtg gttcgacaag tggccttgcg ggccggatcg tcccagtgga agagttgtaa     120
atttgcttct ggccttcccc tacggattat acctggcctt ccctacgga ttatactcaa      180 cttactgttt agaaa atg tgg ccc acg aga cgc ctg gtt act atc aaa agg      231
                 Met Trp Pro Thr Arg Arg Leu Val Thr Ile Lys Arg
                  1               5                  10 agc ggg gtc gac ggt ccc cac ttt ccc ctg agc ctc agc acc tgc ttg       279
Ser Gly Val Asp Gly Pro His Phe Pro Leu Ser Leu Ser Thr Cys Leu
             15                  20                  25 ttt gga agg ggt att gaa tgt gac atc cgt atc cag ctt cct gtt gtg       327
Phe Gly Arg Gly Ile Glu Cys Asp Ile Arg Ile Gln Leu Pro Val Val
         30                  35                  40 tca aaa caa cat tgc aaa att gaa atc cat gag cag gag gca ata tta       375
Ser Lys Gln His Cys Lys Ile Glu Ile His Glu Gln Glu Ala Ile Leu
 45                  50                  55                  60 cat aat ttc agt tcc aca aat cca aca caa gta aat ggg tct gtt att       423
His Asn Phe Ser Ser Thr Asn Pro Thr Gln Val Asn Gly Ser Val Ile
                 65                  70                  75 gat gag cct gta cgg cta aaa cat gga gat gta ata act att att gat       471
Asp Glu Pro Val Arg Leu Lys His Gly Asp Val Ile Thr Ile Ile Asp
             80                  85                  90 cgt tcc ttc agg tat gaa aat gaa agt ctt cag aat gga agg aag tca       519
Arg Ser Phe Arg Tyr Glu Asn Glu Ser Leu Gln Asn Gly Arg Lys Ser
         95                 100                 105 act gaa ttt cca aga aaa ata cgt gaa cag gag cca gca cgt cgt gtc       567
Thr Glu Phe Pro Arg Lys Ile Arg Glu Gln Glu Pro Ala Arg Arg Val
    110                 115                 120 tca aga tct agc ttc tct tct gac cct gat gag agt gag gga ata cct       615
Ser Arg Ser Ser Phe Ser Ser Asp Pro Asp Glu Ser Glu Gly Ile Pro
125                 130                 135                 140 ttg aaa aga agg cgt gtg tcc ttt ggt ggg cac cta aga cct gaa cta       663
Leu Lys Arg Arg Arg Val Ser Phe Gly Gly His Leu Arg Pro Glu Leu
                145                 150                 155 ttt gat gaa aac ttg cct cct aat acg cct ctc aaa agg gga gaa gcc       711
Phe Asp Glu Asn Leu Pro Pro Asn Thr Pro Leu Lys Arg Gly Glu Ala
            160                 165                 170 cca acc aaa aga aag tct ctg gta atg cac act cca cct gtc ctg aag       759
Pro Thr Lys Arg Lys Ser Leu Val Met His Thr Pro Pro Val Leu Lys
```

```
                    175                 180                 185
aaa atc atc aag gaa cag cct caa cca tca gga aaa caa gag tca ggt          807
Lys Ile Ile Lys Glu Gln Pro Gln Pro Ser Gly Lys Gln Glu Ser Gly
190                 195                 200 tca gaa atc cat gtg gaa gtg aag gca caa agc ttg gtt ata agc cct          855
Ser Glu Ile His Val Glu Val Lys Ala Gln Ser Leu Val Ile Ser Pro
205                 210                 215                 220 cca gct cct agt cct agg aaa act cca gtt gcc agt gat caa cgc cgt          903
Pro Ala Pro Ser Pro Arg Lys Thr Pro Val Ala Ser Asp Gln Arg Arg
                225                 230                 235 agg tcc tgc aaa aca gcc cct gct tcc agc agc aaa tct cag aca gag          951
Arg Ser Cys Lys Thr Ala Pro Ala Ser Ser Ser Lys Ser Gln Thr Glu
            240                 245                 250 gtt cct aag aga gga ggg aga aag agt ggc aac ctg cct tca aag aga          999
Val Pro Lys Arg Gly Gly Arg Lys Ser Gly Asn Leu Pro Ser Lys Arg
        255                 260                 265 gtg tct atc agc cga agt caa cat gat att tta cag atg ata tgt tcc         1047
Val Ser Ile Ser Arg Ser Gln His Asp Ile Leu Gln Met Ile Cys Ser
    270                 275                 280 aaa aga aga agt ggt gct tcg gaa gca aat ctg att gtt gca aaa tca         1095
Lys Arg Arg Ser Gly Ala Ser Glu Ala Asn Leu Ile Val Ala Lys Ser
285                 290                 295                 300 tgg gca gat gta gta aaa ctt ggt gca aaa caa aca caa act aaa gtc         1143
Trp Ala Asp Val Val Lys Leu Gly Ala Lys Gln Thr Gln Thr Lys Val
                305                 310                 315 ata aaa cat ggt cct caa agg tca atg aac aaa agg caa aga aga cct         1191
Ile Lys His Gly Pro Gln Arg Ser Met Asn Lys Arg Gln Arg Arg Pro
            320                 325                 330 gct act cca aag aag cct gtg ggc gaa gtt cac agt caa ttt agt aca         1239
Ala Thr Pro Lys Lys Pro Val Gly Glu Val His Ser Gln Phe Ser Thr
        335                 340                 345 ggc cac gca aac tct cct tgt acc ata ata ata ggg aaa gct cat act         1287
Gly His Ala Asn Ser Pro Cys Thr Ile Ile Ile Gly Lys Ala His Thr
    350                 355                 360 gaa aaa gta cat gtg cct gct cga ccc tac aga gtg ctc aac aac ttc         1335
Glu Lys Val His Val Pro Ala Arg Pro Tyr Arg Val Leu Asn Asn Phe
365                 370                 375                 380 att tcc aac caa aaa atg gac ttt aag gaa gat ctt tca gga ata gct         1383
Ile Ser Asn Gln Lys Met Asp Phe Lys Glu Asp Leu Ser Gly Ile Ala
                385                 390                 395 gaa atg ttc aag acc cca gtg aag gag caa ccg cag ttg aca agc aca         1431
Glu Met Phe Lys Thr Pro Val Lys Glu Gln Pro Gln Leu Thr Ser Thr
            400                 405                 410 tgt cac atc gct att tca aat tca gag aat ttg ctt gga aaa cag ttt         1479
Cys His Ile Ala Ile Ser Asn Ser Glu Asn Leu Leu Gly Lys Gln Phe
        415                 420                 425 caa gga act gat tca gga gaa gaa cct ctg ctc ccc acc tca gag agt         1527
Gln Gly Thr Asp Ser Gly Glu Glu Pro Leu Leu Pro Thr Ser Glu Ser
    430                 435                 440 ttt gga gga aat gtg ttc ttc agt gca cag aat gca gca aaa cag cca         1575
Phe Gly Gly Asn Val Phe Phe Ser Ala Gln Asn Ala Ala Lys Gln Pro
445                 450                 455                 460 tct gat aaa tgc tct gca agc cct ccc tta aga cgg cag tgt att aga         1623
Ser Asp Lys Cys Ser Ala Ser Pro Pro Leu Arg Arg Gln Cys Ile Arg
                465                 470                 475 gaa aat gga aac gta gca aaa acg ccc agg aac acc tac aaa atg act         1671
Glu Asn Gly Asn Val Ala Lys Thr Pro Arg Asn Thr Tyr Lys Met Thr
            480                 485                 490 tct ctg gag aca aaa act tca gat act gag aca gag cct tca aaa aca         1719
```

-continued

| | | | | | | | | | | | | | | |
|---|---|---|---|---|---|---|---|---|---|---|---|---|---|---|
|Ser|Leu|Glu|Thr|Lys|Thr|Ser|Asp|Thr|Glu|Thr|Glu|Pro|Ser|Lys|Thr|
| | |495| | | | |500| | | |505| | | |

```
gta tcc act gca aac agg tca gga agg tct aca gag ttc agg aat ata      1767
Val Ser Thr Ala Asn Arg Ser Gly Arg Ser Thr Glu Phe Arg Asn Ile
510                 515                 520 cag aag cta cct gtg gaa agt aag agt gaa gaa aca aat aca gaa att      1815
Gln Lys Leu Pro Val Glu Ser Lys Ser Glu Glu Thr Asn Thr Glu Ile
525                 530                 535                 540 gtt gag tgc atc cta aaa aga ggt cag aag gca aca cta cta caa caa      1863
Val Glu Cys Ile Leu Lys Arg Gly Gln Lys Ala Thr Leu Leu Gln Gln
                545                 550                 555 agg aga gaa gga gag atg aag gaa ata gaa aga cct ttt gag aca tat      1911
Arg Arg Glu Gly Glu Met Lys Glu Ile Glu Arg Pro Phe Glu Thr Tyr
            560                 565                 570 aag gaa aat att gaa tta aaa gaa aac gat gaa aag atg aaa gca atg      1959
Lys Glu Asn Ile Glu Leu Lys Glu Asn Asp Glu Lys Met Lys Ala Met
575                 580                 585 aag aga tca aga act tgg ggg cag aaa tgt gca cca atg tct gac ctg      2007
Lys Arg Ser Arg Thr Trp Gly Gln Lys Cys Ala Pro Met Ser Asp Leu
590                 595                 600 aca gac ctc aag agc ttg cct gat aca gaa ctc atg aaa gac acg gca      2055
Thr Asp Leu Lys Ser Leu Pro Asp Thr Glu Leu Met Lys Asp Thr Ala
605                 610                 615                 620 cgt ggc cag aat ctc ctc caa acc caa gat cat gcc aag gca cca aag      2103
Arg Gly Gln Asn Leu Leu Gln Thr Gln Asp His Ala Lys Ala Pro Lys
                625                 630                 635 agt gag aaa ggc aaa atc act aaa atg ccc tgc cag tca tta caa cca      2151
Ser Glu Lys Gly Lys Ile Thr Lys Met Pro Cys Gln Ser Leu Gln Pro
            640                 645                 650 gaa cca ata aac acc cca aca cac aca aaa caa cag ttg aag gca tcc      2199
Glu Pro Ile Asn Thr Pro Thr His Thr Lys Gln Gln Leu Lys Ala Ser
655                 660                 665 ctg ggg aaa gta ggt gtg aaa gaa gag ctc cta gca gtc ggc aag ttc      2247
Leu Gly Lys Val Gly Val Lys Glu Glu Leu Leu Ala Val Gly Lys Phe
670                 675                 680 aca cgg acg tca ggg gag acc acg cac acg cac aga gag cca gca gga      2295
Thr Arg Thr Ser Gly Glu Thr Thr His Thr His Arg Glu Pro Ala Gly
685                 690                 695                 700 gat ggc aag agc atc aga acg ttt aag gag tct cca aag cag atc ctg      2343
Asp Gly Lys Ser Ile Arg Thr Phe Lys Glu Ser Pro Lys Gln Ile Leu
                705                 710                 715 gac cca gca gcc cgt gta act gga atg aag aag tgg cca aga acg cct      2391
Asp Pro Ala Ala Arg Val Thr Gly Met Lys Lys Trp Pro Arg Thr Pro
            720                 725                 730 aag gaa gag gcc cag tca cta gaa gac ctg gct ggc ttc aaa gag ctc      2439
Lys Glu Glu Ala Gln Ser Leu Glu Asp Leu Ala Gly Phe Lys Glu Leu
735                 740                 745 ttc cag aca cca ggt ccc tct gag gaa tca atg act gat gag aaa act      2487
Phe Gln Thr Pro Gly Pro Ser Glu Glu Ser Met Thr Asp Glu Lys Thr
750                 755                 760 acc aaa ata gcc tgc aaa tct cca cca cca gaa tca gtg gac act cca      2535
Thr Lys Ile Ala Cys Lys Ser Pro Pro Pro Glu Ser Val Asp Thr Pro
765                 770                 775                 780 aca agc aca aag caa tgg cct aag aga agt ctc agg aaa gca gat gta      2583
Thr Ser Thr Lys Gln Trp Pro Lys Arg Ser Leu Arg Lys Ala Asp Val
                785                 790                 795 gag gaa gaa ttc tta gca ctc agg aaa cta aca cca tca gca ggg aaa      2631
Glu Glu Glu Phe Leu Ala Leu Arg Lys Leu Thr Pro Ser Ala Gly Lys
            800                 805                 810
```

-continued

```
gcc atg ctt acg ccc aaa cca gca gga ggt gat gag aaa gac att aaa    2679
Ala Met Leu Thr Pro Lys Pro Ala Gly Gly Asp Glu Lys Asp Ile Lys
    815                 820                 825 gca ttt atg gga act cca gtg cag aaa ctg gac ctg gca gga act tta    2727
Ala Phe Met Gly Thr Pro Val Gln Lys Leu Asp Leu Ala Gly Thr Leu
830                 835                 840 cct ggc agc aaa aga cag cta cag act cct aag gaa aag gcc cag gct    2775
Pro Gly Ser Lys Arg Gln Leu Gln Thr Pro Lys Glu Lys Ala Gln Ala
845                 850                 855                 860 cta gaa gac ctg gct ggc ttt aaa gag ctc ttc cag act cct ggt cac    2823
Leu Glu Asp Leu Ala Gly Phe Lys Glu Leu Phe Gln Thr Pro Gly His
                865                 870                 875 acc gag gaa tta gtg gct gct ggt aaa acc act aaa ata ccc tgc gac    2871
Thr Glu Glu Leu Val Ala Ala Gly Lys Thr Thr Lys Ile Pro Cys Asp
            880                 885                 890 tct cca cag tca gac cca gtg gac acc cca aca agc aca aag caa cga    2919
Ser Pro Gln Ser Asp Pro Val Asp Thr Pro Thr Ser Thr Lys Gln Arg
        895                 900                 905 ccc aag aga agt atc agg aaa gca gat gta gag gga gaa ctc tta gcg    2967
Pro Lys Arg Ser Ile Arg Lys Ala Asp Val Glu Gly Glu Leu Leu Ala
910                 915                 920 tgc agg aat cta atg cca tca gca ggc aaa gcc atg cac acg cct aaa    3015
Cys Arg Asn Leu Met Pro Ser Ala Gly Lys Ala Met His Thr Pro Lys
925                 930                 935                 940 cca tca gta ggt gaa gag aaa gac atc atc ata ttt gtg gga act cca    3063
Pro Ser Val Gly Glu Glu Lys Asp Ile Ile Ile Phe Val Gly Thr Pro
                945                 950                 955 gtg cag aaa ctg gac ctg aca gag aac tta acc ggc agc aag aga cgg    3111
Val Gln Lys Leu Asp Leu Thr Glu Asn Leu Thr Gly Ser Lys Arg Arg
            960                 965                 970 cca caa act cct aag gaa gag gcc cag gct ctg gaa gac ctg act ggc    3159
Pro Gln Thr Pro Lys Glu Glu Ala Gln Ala Leu Glu Asp Leu Thr Gly
        975                 980                 985 ttt aaa gag ctc ttc cag acc cct ggt cat act gaa gaa gca gtg gct    3207
Phe Lys Glu Leu Phe Gln Thr Pro Gly His Thr Glu Glu Ala Val Ala
    990                 995                 1000 gct ggc aaa act act aaa atg ccc tgc gaa tct tct cca cca gaa       3252
Ala Gly Lys Thr Thr Lys Met Pro Cys Glu Ser Ser Pro Pro Glu
1005                1010                1015 tca gca gac acc cca aca agc aca aga agg cag ccc aag aca cct       3297
Ser Ala Asp Thr Pro Thr Ser Thr Arg Arg Gln Pro Lys Thr Pro
1020                1025                1030 ttg gag aaa agg gac gta cag aag gag ctc tca gcc ctg aag aag       3342
Leu Glu Lys Arg Asp Val Gln Lys Glu Leu Ser Ala Leu Lys Lys
1035                1040                1045 ctc aca cag aca tca ggg gaa acc aca cac aca gat aaa gta cca       3387
Leu Thr Gln Thr Ser Gly Glu Thr Thr His Thr Asp Lys Val Pro
1050                1055                1060 gga ggt gag gat aaa agc atc aac gcg ttt agg gaa act gca aaa       3432
Gly Gly Glu Asp Lys Ser Ile Asn Ala Phe Arg Glu Thr Ala Lys
1065                1070                1075 cag aaa ctg gac cca gca gca agt gta act ggt agc aag agg cac       3477
Gln Lys Leu Asp Pro Ala Ala Ser Val Thr Gly Ser Lys Arg His
1080                1085                1090 cca aaa act aag gaa aag gcc caa ccc cta gaa gac ctg gct ggc       3522
Pro Lys Thr Lys Glu Lys Ala Gln Pro Leu Glu Asp Leu Ala Gly
1095                1100                1105 ttg aaa gag ctc ttc cag aca cca gta tgc act gac aag ccc acg       3567
Leu Lys Glu Leu Phe Gln Thr Pro Val Cys Thr Asp Lys Pro Thr
1110                1115                1120
```

| | | | | | | | | | | | | | |
|---|---|---|---|---|---|---|---|---|---|---|---|---|---|
| act | cac | gag | aaa | act | acc | aaa | ata | gcc | tgc | aga | tca | caa | cca gac | 3612 |
| Thr | His | Glu | Lys | Thr | Thr | Lys | Ile | Ala | Cys | Arg | Ser | Gln | Pro Asp |
| 1125 | | | | 1130 | | | | | 1135 | | | | |
| cca | gtg | gac | aca | cca | aca | agc | tcc | aag | cca | cag | tcc | aag | aga agt | 3657 |
| Pro | Val | Asp | Thr | Pro | Thr | Ser | Ser | Lys | Pro | Gln | Ser | Lys | Arg Ser |
| 1140 | | | | 1145 | | | | | 1150 | | | | |
| ctc | agg | aaa | gtg | gac | gta | gaa | gaa | gaa | ttc | ttc | gca | ctc | agg aaa | 3702 |
| Leu | Arg | Lys | Val | Asp | Val | Glu | Glu | Glu | Phe | Phe | Ala | Leu | Arg Lys |
| 1155 | | | | 1160 | | | | | 1165 | | | | |
| cga | aca | cca | tca | gca | ggc | aaa | gcc | atg | cac | aca | ccc | aaa | cca gca | 3747 |
| Arg | Thr | Pro | Ser | Ala | Gly | Lys | Ala | Met | His | Thr | Pro | Lys | Pro Ala |
| 1170 | | | | 1175 | | | | | 1180 | | | | |
| gta | agt | ggt | gag | aaa | aac | atc | tac | gca | ttt | atg | gga | act | cca gtg | 3792 |
| Val | Ser | Gly | Glu | Lys | Asn | Ile | Tyr | Ala | Phe | Met | Gly | Thr | Pro Val |
| 1185 | | | | 1190 | | | | | 1195 | | | | |
| cag | aaa | ctg | gac | ctg | aca | gag | aac | tta | act | ggc | agc | aag | aga cgg | 3837 |
| Gln | Lys | Leu | Asp | Leu | Thr | Glu | Asn | Leu | Thr | Gly | Ser | Lys | Arg Arg |
| 1200 | | | | 1205 | | | | | 1210 | | | | |
| cta | caa | act | cct | aag | gaa | aag | gcc | cag | gct | cta | gaa | gac | ctg gct | 3882 |
| Leu | Gln | Thr | Pro | Lys | Glu | Lys | Ala | Gln | Ala | Leu | Glu | Asp | Leu Ala |
| 1215 | | | | 1220 | | | | | 1225 | | | | |
| ggc | ttt | aaa | gag | ctc | ttc | cag | aca | cga | ggt | cac | act | gag | gaa tca | 3927 |
| Gly | Phe | Lys | Glu | Leu | Phe | Gln | Thr | Arg | Gly | His | Thr | Glu | Glu Ser |
| 1230 | | | | 1235 | | | | | 1240 | | | | |
| atg | act | aac | gat | aaa | act | gcc | aaa | gta | gcc | tgc | aaa | tct | tca caa | 3972 |
| Met | Thr | Asn | Asp | Lys | Thr | Ala | Lys | Val | Ala | Cys | Lys | Ser | Ser Gln |
| 1245 | | | | 1250 | | | | | 1255 | | | | |
| cca | gac | cca | gac | aaa | aac | cca | gca | agc | tcc | aag | cga | cgg | ctc aag | 4017 |
| Pro | Asp | Pro | Asp | Lys | Asn | Pro | Ala | Ser | Ser | Lys | Arg | Arg | Leu Lys |
| 1260 | | | | 1265 | | | | | 1270 | | | | |
| aca | tcc | ctg | ggg | aaa | gtg | ggc | gtg | aaa | gaa | gag | ctc | cta | gca gtt | 4062 |
| Thr | Ser | Leu | Gly | Lys | Val | Gly | Val | Lys | Glu | Glu | Leu | Leu | Ala Val |
| 1275 | | | | 1280 | | | | | 1285 | | | | |
| ggc | aag | ctc | aca | cag | aca | tca | gga | gag | act | aca | cac | aca | cac aca | 4107 |
| Gly | Lys | Leu | Thr | Gln | Thr | Ser | Gly | Glu | Thr | Thr | His | Thr | His Thr |
| 1290 | | | | 1295 | | | | | 1300 | | | | |
| gag | cca | aca | gga | gat | ggt | aag | agc | atg | aaa | gca | ttt | atg | gag tct | 4152 |
| Glu | Pro | Thr | Gly | Asp | Gly | Lys | Ser | Met | Lys | Ala | Phe | Met | Glu Ser |
| 1305 | | | | 1310 | | | | | 1315 | | | | |
| cca | aag | cag | atc | tta | gac | tca | gca | gca | agt | cta | act | ggc | agc aag | 4197 |
| Pro | Lys | Gln | Ile | Leu | Asp | Ser | Ala | Ala | Ser | Leu | Thr | Gly | Ser Lys |
| 1320 | | | | 1325 | | | | | 1330 | | | | |
| agg | cag | ctg | aga | act | cct | aag | gga | aag | tct | gaa | gtc | cct | gaa gac | 4242 |
| Arg | Gln | Leu | Arg | Thr | Pro | Lys | Gly | Lys | Ser | Glu | Val | Pro | Glu Asp |
| 1335 | | | | 1340 | | | | | 1345 | | | | |
| ctg | gcc | ggc | ttc | atc | gag | ctc | ttc | cag | aca | cca | agt | cac | act aag | 4287 |
| Leu | Ala | Gly | Phe | Ile | Glu | Leu | Phe | Gln | Thr | Pro | Ser | His | Thr Lys |
| 1350 | | | | 1355 | | | | | 1360 | | | | |
| gaa | tca | atg | act | aac | gaa | aaa | act | acc | aaa | gta | tcc | tac | aga gct | 4332 |
| Glu | Ser | Met | Thr | Asn | Glu | Lys | Thr | Thr | Lys | Val | Ser | Tyr | Arg Ala |
| 1365 | | | | 1370 | | | | | 1375 | | | | |
| tca | cag | cca | gac | cta | gtg | gac | acc | cca | aca | agc | tcc | aag | cca cag | 4377 |
| Ser | Gln | Pro | Asp | Leu | Val | Asp | Thr | Pro | Thr | Ser | Ser | Lys | Pro Gln |
| 1380 | | | | 1385 | | | | | 1390 | | | | |
| ccc | aag | aga | agt | ctc | agg | aaa | gca | gac | act | gaa | gaa | gaa | ttt tta | 4422 |
| Pro | Lys | Arg | Ser | Leu | Arg | Lys | Ala | Asp | Thr | Glu | Glu | Glu | Phe Leu |
| 1395 | | | | 1400 | | | | | 1405 | | | | |
| gca | ttt | agg | aaa | caa | acg | cca | tca | gca | ggc | aaa | gcc | atg | cac aca | 4467 |
| Ala | Phe | Arg | Lys | Gln | Thr | Pro | Ser | Ala | Gly | Lys | Ala | Met | His Thr |

```
                      -continued
1410              1415              1420 ccc aaa cca gca gta ggt gaa gag aaa gac atc aac acg ttt ttg   4512
Pro Lys Pro Ala Val Gly Glu Glu Lys Asp Ile Asn Thr Phe Leu
1425              1430              1435 gga act cca gtg cag aaa ctg gac cag cca gga aat tta cct ggc   4557
Gly Thr Pro Val Gln Lys Leu Asp Gln Pro Gly Asn Leu Pro Gly
1440              1445              1450 agc aat aga cgg cta caa act cgt aag gaa aag gcc cag gct cta   4602
Ser Asn Arg Arg Leu Gln Thr Arg Lys Glu Lys Ala Gln Ala Leu
1455              1460              1465 gaa gaa ctg act ggc ttc aga gag ctt ttc cag aca cca tgc act   4647
Glu Glu Leu Thr Gly Phe Arg Glu Leu Phe Gln Thr Pro Cys Thr
1470              1475              1480 gat aac ccc acg act gat gag aaa act acc aaa aaa ata ctc tgc   4692
Asp Asn Pro Thr Thr Asp Glu Lys Thr Thr Lys Lys Ile Leu Cys
1485              1490              1495 aaa tct ccg caa tca gac cca gcg gac acc cca aca aac aca aag   4737
Lys Ser Pro Gln Ser Asp Pro Ala Asp Thr Pro Thr Asn Thr Lys
1500              1505              1510 caa cgg ccc aag aga agc ctc aag aaa gca gac gta gag gaa gaa   4782
Gln Arg Pro Lys Arg Ser Leu Lys Lys Ala Asp Val Glu Glu Glu
1515              1520              1525 ttt tta gca ttc agg aaa cta aca cca tca gca ggc aaa gcc atg   4827
Phe Leu Ala Phe Arg Lys Leu Thr Pro Ser Ala Gly Lys Ala Met
1530              1535              1540 cac acg cct aaa gca gca gta ggt gaa gag aaa gac atc aac aca   4872
His Thr Pro Lys Ala Ala Val Gly Glu Glu Lys Asp Ile Asn Thr
1545              1550              1555 ttt gtg ggg act cca gtg gag aaa ctg gac ctg cta gga aat tta   4917
Phe Val Gly Thr Pro Val Glu Lys Leu Asp Leu Leu Gly Asn Leu
1560              1565              1570 cct ggc agc aag aga cgg cca caa act cct aaa gaa aag gcc aag   4962
Pro Gly Ser Lys Arg Arg Pro Gln Thr Pro Lys Glu Lys Ala Lys
1575              1580              1585 gct cta gaa gat ctg gct ggc ttc aaa gag ctc ttc cag aca cca   5007
Ala Leu Glu Asp Leu Ala Gly Phe Lys Glu Leu Phe Gln Thr Pro
1590              1595              1600 ggt cac act gag gaa tca atg acc gat gac aaa atc aca gaa gta   5052
Gly His Thr Glu Glu Ser Met Thr Asp Asp Lys Ile Thr Glu Val
1605              1610              1615 tcc tgc aaa tct cca caa cca gac cca gtc aaa acc cca aca agc   5097
Ser Cys Lys Ser Pro Gln Pro Asp Pro Val Lys Thr Pro Thr Ser
1620              1625              1630 tcc aag caa cga ctc aag ata tcc ttg ggg aaa gta ggt gtg aaa   5142
Ser Lys Gln Arg Leu Lys Ile Ser Leu Gly Lys Val Gly Val Lys
1635              1640              1645 gaa gag gtc cta cca gtc ggc aag ctc aca cag acg tca ggg aag   5187
Glu Glu Val Leu Pro Val Gly Lys Leu Thr Gln Thr Ser Gly Lys
1650              1655              1660 acc aca cag aca cac aga gag aca gca gga gat gga aag agc atc   5232
Thr Thr Gln Thr His Arg Glu Thr Ala Gly Asp Gly Lys Ser Ile
1665              1670              1675 aaa gcg ttt aag gaa tct gca aag cag atg ctg gac cca gca aac   5277
Lys Ala Phe Lys Glu Ser Ala Lys Gln Met Leu Asp Pro Ala Asn
1680              1685              1690 tat gga act ggg atg gag agg tgg cca aga aca cct aag gaa gag   5322
Tyr Gly Thr Gly Met Glu Arg Trp Pro Arg Thr Pro Lys Glu Glu
1695              1700              1705 gcc caa tca cta gaa gac ctg gcc ggc ttc aaa gag ctc ttc cag   5367
```

-continued

| | | | | | | | | | | | | | | |
|---|---|---|---|---|---|---|---|---|---|---|---|---|---|---|
| Ala | Gln | Ser | Leu | Glu | Asp | Leu | Ala | Gly | Phe | Lys | Glu | Leu | Phe | Gln |
| 1710 | | | | 1715 | | | | | 1720 | | | | | |

```
aca  cca  gac  cac  act  gag  gaa  tca  aca  act  gat  gac  aaa  act  acc        5412
Thr  Pro  Asp  His  Thr  Glu  Glu  Ser  Thr  Thr  Asp  Asp  Lys  Thr  Thr
1725           1730                     1735 aaa  ata  gcc  tgc  aaa  tct  cca  cca  cca  gaa  tca  atg  gac  act  cca        5457
Lys  Ile  Ala  Cys  Lys  Ser  Pro  Pro  Pro  Glu  Ser  Met  Asp  Thr  Pro
1740           1745                     1750 aca  agc  aca  agg  agg  cgg  ccc  aaa  aca  cct  ttg  ggg  aaa  agg  gat        5502
Thr  Ser  Thr  Arg  Arg  Arg  Pro  Lys  Thr  Pro  Leu  Gly  Lys  Arg  Asp
1755           1760                     1765 ata  gtg  gaa  gag  ctc  tca  gcc  ctg  aag  cag  ctc  aca  cag  acc  aca        5547
Ile  Val  Glu  Glu  Leu  Ser  Ala  Leu  Lys  Gln  Leu  Thr  Gln  Thr  Thr
1770           1775                     1780 cac  aca  gac  aaa  gta  cca  gga  gat  gag  gat  aaa  ggc  atc  aac  gtg        5592
His  Thr  Asp  Lys  Val  Pro  Gly  Asp  Glu  Asp  Lys  Gly  Ile  Asn  Val
1785           1790                     1795 ttc  agg  gaa  act  gca  aaa  cag  aaa  ctg  gac  cca  gca  gca  agt  gta        5637
Phe  Arg  Glu  Thr  Ala  Lys  Gln  Lys  Leu  Asp  Pro  Ala  Ala  Ser  Val
1800           1805                     1810 act  ggt  agc  aag  agg  cag  cca  aga  act  cct  aag  gga  aaa  gcc  caa        5682
Thr  Gly  Ser  Lys  Arg  Gln  Pro  Arg  Thr  Pro  Lys  Gly  Lys  Ala  Gln
1815           1820                     1825 ccc  cta  gaa  gac  ttg  gct  ggc  ttg  aaa  gag  ctc  ttc  cag  aca  cca        5727
Pro  Leu  Glu  Asp  Leu  Ala  Gly  Leu  Lys  Glu  Leu  Phe  Gln  Thr  Pro
1830           1835                     1840 ata  tgc  act  gac  aag  ccc  acg  act  cat  gag  aaa  act  acc  aaa  ata        5772
Ile  Cys  Thr  Asp  Lys  Pro  Thr  Thr  His  Glu  Lys  Thr  Thr  Lys  Ile
1845           1850                     1855 gcc  tgc  aga  tct  cca  caa  cca  gac  cca  gtg  ggt  acc  cca  aca  atc        5817
Ala  Cys  Arg  Ser  Pro  Gln  Pro  Asp  Pro  Val  Gly  Thr  Pro  Thr  Ile
1860           1865                     1870 ttc  aag  cca  cag  tcc  aag  aga  agt  ctc  agg  aaa  gca  gac  gta  gag        5862
Phe  Lys  Pro  Gln  Ser  Lys  Arg  Ser  Leu  Arg  Lys  Ala  Asp  Val  Glu
1875           1880                     1885 gaa  gaa  tcc  tta  gca  ctc  agg  aaa  cga  aca  cca  tca  gta  ggg  aaa        5907
Glu  Glu  Ser  Leu  Ala  Leu  Arg  Lys  Arg  Thr  Pro  Ser  Val  Gly  Lys
1890           1895                     1900 gct  atg  gac  aca  ccc  aaa  cca  gca  gga  ggt  gat  gag  aaa  gac  atg        5952
Ala  Met  Asp  Thr  Pro  Lys  Pro  Ala  Gly  Gly  Asp  Glu  Lys  Asp  Met
1905           1910                     1915 aaa  gca  ttt  atg  gga  act  cca  gtg  cag  aaa  ttg  gac  ctg  cca  gga        5997
Lys  Ala  Phe  Met  Gly  Thr  Pro  Val  Gln  Lys  Leu  Asp  Leu  Pro  Gly
1920           1925                     1930 aat  tta  cct  ggc  agc  aaa  aga  tgg  cca  caa  act  cct  aag  gaa  aag        6042
Asn  Leu  Pro  Gly  Ser  Lys  Arg  Trp  Pro  Gln  Thr  Pro  Lys  Glu  Lys
1935           1940                     1945 gcc  cag  gct  cta  gaa  gac  ctg  gct  ggc  ttc  aaa  gag  ctc  ttc  cag        6087
Ala  Gln  Ala  Leu  Glu  Asp  Leu  Ala  Gly  Phe  Lys  Glu  Leu  Phe  Gln
1950           1955                     1960 aca  cca  ggc  act  gac  aag  ccc  acg  act  gat  gag  aaa  act  acc  aaa        6132
Thr  Pro  Gly  Thr  Asp  Lys  Pro  Thr  Thr  Asp  Glu  Lys  Thr  Thr  Lys
1965           1970                     1975 ata  gcc  tgc  aaa  tct  cca  caa  cca  gac  cca  gtg  gac  acc  cca  gca        6177
Ile  Ala  Cys  Lys  Ser  Pro  Gln  Pro  Asp  Pro  Val  Asp  Thr  Pro  Ala
1980           1985                     1990 agc  aca  aag  caa  cgg  ccc  aag  aga  aac  ctc  agg  aaa  gca  gac  gta        6222
Ser  Thr  Lys  Gln  Arg  Pro  Lys  Arg  Asn  Leu  Arg  Lys  Ala  Asp  Val
1995           2000                     2005
```

-continued

| | | | | | | | | | | | | | | |
|---|---|---|---|---|---|---|---|---|---|---|---|---|---|---|
| gag | gaa | gaa | ttt | tta | gca | ctc | agg | aaa | cga | aca | cca | tca | gca | ggc | 6267 |
| Glu | Glu | Glu | Phe | Leu | Ala | Leu | Arg | Lys | Arg | Thr | Pro | Ser | Ala | Gly | |
| 2010 | | | | 2015 | | | | | 2020 | | | | | | |

| aaa | gcc | atg | gac | aca | cca | aaa | cca | gca | gta | agt | gat | gag | aaa | aat | 6312 |
|---|---|---|---|---|---|---|---|---|---|---|---|---|---|---|---|
| Lys | Ala | Met | Asp | Thr | Pro | Lys | Pro | Ala | Val | Ser | Asp | Glu | Lys | Asn | |
| 2025 | | | | 2030 | | | | | 2035 | | | | | | |

| atc | aac | aca | ttt | gtg | gaa | act | cca | gtg | cag | aaa | ctg | gac | ctg | cta | 6357 |
|---|---|---|---|---|---|---|---|---|---|---|---|---|---|---|---|
| Ile | Asn | Thr | Phe | Val | Glu | Thr | Pro | Val | Gln | Lys | Leu | Asp | Leu | Leu | |
| 2040 | | | | 2045 | | | | | 2050 | | | | | | |

| gga | aat | tta | cct | ggc | agc | aag | aga | cag | cca | cag | act | cct | aag | gaa | 6402 |
|---|---|---|---|---|---|---|---|---|---|---|---|---|---|---|---|
| Gly | Asn | Leu | Pro | Gly | Ser | Lys | Arg | Gln | Pro | Gln | Thr | Pro | Lys | Glu | |
| 2055 | | | | 2060 | | | | | 2065 | | | | | | |

| aag | gct | gag | gct | cta | gag | gac | ctg | gtt | ggc | ttc | aaa | gaa | ctc | ttc | 6447 |
|---|---|---|---|---|---|---|---|---|---|---|---|---|---|---|---|
| Lys | Ala | Glu | Ala | Leu | Glu | Asp | Leu | Val | Gly | Phe | Lys | Glu | Leu | Phe | |
| 2070 | | | | 2075 | | | | | 2080 | | | | | | |

| cag | aca | cca | ggt | cac | act | gag | gaa | tca | atg | act | gat | gac | aaa | atc | 6492 |
|---|---|---|---|---|---|---|---|---|---|---|---|---|---|---|---|
| Gln | Thr | Pro | Gly | His | Thr | Glu | Glu | Ser | Met | Thr | Asp | Asp | Lys | Ile | |
| 2085 | | | | 2090 | | | | | 2095 | | | | | | |

| aca | gaa | gta | tcc | tgt | aaa | tct | cca | cag | cca | gag | tca | ttc | aaa | acc | 6537 |
|---|---|---|---|---|---|---|---|---|---|---|---|---|---|---|---|
| Thr | Glu | Val | Ser | Cys | Lys | Ser | Pro | Gln | Pro | Glu | Ser | Phe | Lys | Thr | |
| 2100 | | | | 2105 | | | | | 2110 | | | | | | |

| tca | aga | agc | tcc | aag | caa | agg | ctc | aag | ata | ccc | ctg | gtg | aaa | gtg | 6582 |
|---|---|---|---|---|---|---|---|---|---|---|---|---|---|---|---|
| Ser | Arg | Ser | Ser | Lys | Gln | Arg | Leu | Lys | Ile | Pro | Leu | Val | Lys | Val | |
| 2115 | | | | 2120 | | | | | 2125 | | | | | | |

| gac | atg | aaa | gaa | gag | ccc | cta | gca | gtc | agc | aag | ctc | aca | cgg | aca | 6627 |
|---|---|---|---|---|---|---|---|---|---|---|---|---|---|---|---|
| Asp | Met | Lys | Glu | Glu | Pro | Leu | Ala | Val | Ser | Lys | Leu | Thr | Arg | Thr | |
| 2130 | | | | 2135 | | | | | 2140 | | | | | | |

| tca | ggg | gag | act | acg | caa | aca | cac | aca | gag | cca | aca | gga | gat | agt | 6672 |
|---|---|---|---|---|---|---|---|---|---|---|---|---|---|---|---|
| Ser | Gly | Glu | Thr | Thr | Gln | Thr | His | Thr | Glu | Pro | Thr | Gly | Asp | Ser | |
| 2145 | | | | 2150 | | | | | 2155 | | | | | | |

| aag | agc | atc | aaa | gcg | ttt | aag | gag | tct | cca | aag | cag | atc | ctg | gac | 6717 |
|---|---|---|---|---|---|---|---|---|---|---|---|---|---|---|---|
| Lys | Ser | Ile | Lys | Ala | Phe | Lys | Glu | Ser | Pro | Lys | Gln | Ile | Leu | Asp | |
| 2160 | | | | 2165 | | | | | 2170 | | | | | | |

| cca | gca | gca | agt | gta | act | ggt | agc | agg | agg | cag | ctg | aga | act | cgt | 6762 |
|---|---|---|---|---|---|---|---|---|---|---|---|---|---|---|---|
| Pro | Ala | Ala | Ser | Val | Thr | Gly | Ser | Arg | Arg | Gln | Leu | Arg | Thr | Arg | |
| 2175 | | | | 2180 | | | | | 2185 | | | | | | |

| aag | gaa | aag | gcc | cgt | gct | cta | gaa | gac | ctg | gtt | gac | ttc | aaa | gag | 6807 |
|---|---|---|---|---|---|---|---|---|---|---|---|---|---|---|---|
| Lys | Glu | Lys | Ala | Arg | Ala | Leu | Glu | Asp | Leu | Val | Asp | Phe | Lys | Glu | |
| 2190 | | | | 2195 | | | | | 2200 | | | | | | |

| ctc | ttc | tca | gca | cca | ggt | cac | act | gaa | gag | tca | atg | act | att | gac | 6852 |
|---|---|---|---|---|---|---|---|---|---|---|---|---|---|---|---|
| Leu | Phe | Ser | Ala | Pro | Gly | His | Thr | Glu | Glu | Ser | Met | Thr | Ile | Asp | |
| 2205 | | | | 2210 | | | | | 2215 | | | | | | |

| aaa | aac | aca | aaa | att | ccc | tgc | aaa | tct | ccc | cca | gaa | cta | aca | 6897 | |
|---|---|---|---|---|---|---|---|---|---|---|---|---|---|---|---|
| Lys | Asn | Thr | Lys | Ile | Pro | Cys | Lys | Ser | Pro | Pro | Glu | Leu | Thr | | |
| 2220 | | | | 2225 | | | | | 2230 | | | | | | |

| gac | act | gcc | acg | agc | aca | aag | aga | tgc | ccc | aag | aca | cgt | ccc | agg | 6942 |
|---|---|---|---|---|---|---|---|---|---|---|---|---|---|---|---|
| Asp | Thr | Ala | Thr | Ser | Thr | Lys | Arg | Cys | Pro | Lys | Thr | Arg | Pro | Arg | |
| 2235 | | | | 2240 | | | | | 2245 | | | | | | |

| aaa | gaa | gta | aaa | gag | gag | ctc | tca | gca | gtt | gag | agg | ctc | acg | caa | 6987 |
|---|---|---|---|---|---|---|---|---|---|---|---|---|---|---|---|
| Lys | Glu | Val | Lys | Glu | Glu | Leu | Ser | Ala | Val | Glu | Arg | Leu | Thr | Gln | |
| 2250 | | | | 2255 | | | | | 2260 | | | | | | |

| aca | tca | ggg | caa | agc | aca | cac | aca | cac | aaa | gaa | cca | gca | agc | ggt | 7032 |
|---|---|---|---|---|---|---|---|---|---|---|---|---|---|---|---|
| Thr | Ser | Gly | Gln | Ser | Thr | His | Thr | His | Lys | Glu | Pro | Ala | Ser | Gly | |
| 2265 | | | | 2270 | | | | | 2275 | | | | | | |

| gat | gag | ggc | atc | aaa | gta | ttg | aag | caa | cgt | gca | aag | aag | aaa | cca | 7077 |
|---|---|---|---|---|---|---|---|---|---|---|---|---|---|---|---|
| Asp | Glu | Gly | Ile | Lys | Val | Leu | Lys | Gln | Arg | Ala | Lys | Lys | Lys | Pro | |
| 2280 | | | | 2285 | | | | | 2290 | | | | | | |

| aac | cca | gta | gaa | gag | gaa | ccc | agc | agg | aga | agg | cca | aga | gca | cct | 7122 |
|---|---|---|---|---|---|---|---|---|---|---|---|---|---|---|---|
| Asn | Pro | Val | Glu | Glu | Glu | Pro | Ser | Arg | Arg | Arg | Pro | Arg | Ala | Pro | |
| 2295 | | | | 2300 | | | | | 2305 | | | | | | |

```
aag gaa aag gcc caa ccc ctg gaa gac ctg gcc ggc ttc aca gag   7167
Lys Glu Lys Ala Gln Pro Leu Glu Asp Leu Ala Gly Phe Thr Glu
2310            2315                2320 ctc tct gaa aca tca ggt cac act cag gaa tcg ctg act gct ggc   7212
Leu Ser Glu Thr Ser Gly His Thr Gln Glu Ser Leu Thr Ala Gly
2325            2330                2335 aaa gcc act aaa ata ccc tgc gaa tct cca cta gaa gtg gta       7257
Lys Ala Thr Lys Ile Pro Cys Glu Ser Pro Leu Glu Val Val
2340            2345                2350 gac acc aca gca agc aca aag agg cat ctc agg aca cgt gtg cag   7302
Asp Thr Thr Ala Ser Thr Lys Arg His Leu Arg Thr Arg Val Gln
2355            2360                2365 aag gta caa gta aaa gaa gag cct tca gca gtc aag ttc aca caa   7347
Lys Val Gln Val Lys Glu Glu Pro Ser Ala Val Lys Phe Thr Gln
2370            2375                2380 aca tca ggg gaa acc acg gat gca gac aaa gaa cca gca ggt gaa   7392
Thr Ser Gly Glu Thr Thr Asp Ala Asp Lys Glu Pro Ala Gly Glu
2385            2390                2395 gat aaa ggc atc aaa gca ttg aag gaa tct gca aaa cag aca ccg   7437
Asp Lys Gly Ile Lys Ala Leu Lys Glu Ser Ala Lys Gln Thr Pro
2400            2405                2410 gct cca gca gca agt gta act ggc agc agg aga cgg cca aga gca   7482
Ala Pro Ala Ala Ser Val Thr Gly Ser Arg Arg Arg Pro Arg Ala
2415            2420                2425 ccc agg gaa agt gcc caa gcc ata gaa gac cta gct ggc ttc aaa   7527
Pro Arg Glu Ser Ala Gln Ala Ile Glu Asp Leu Ala Gly Phe Lys
2430            2435                2440 gac cca gca gca ggt cac act gaa gaa tca atg act gat gac aaa   7572
Asp Pro Ala Ala Gly His Thr Glu Glu Ser Met Thr Asp Asp Lys
2445            2450                2455 acc act aaa ata ccc tgc aaa tca tca cca gaa cta gaa gac acc   7617
Thr Thr Lys Ile Pro Cys Lys Ser Ser Pro Glu Leu Glu Asp Thr
2460            2465                2470 gca aca agc tca aag aga cgg ccc agg aca cgt gcc cag aaa gta   7662
Ala Thr Ser Ser Lys Arg Arg Pro Arg Thr Arg Ala Gln Lys Val
2475            2480                2485 gaa gtg aag gag gag ctg tta gca gtt ggc aag ctc aca caa acc   7707
Glu Val Lys Glu Glu Leu Leu Ala Val Gly Lys Leu Thr Gln Thr
2490            2495                2500 tca ggg gag acc acg cac acc gac aaa gag ccg gta ggt gag ggc   7752
Ser Gly Glu Thr Thr His Thr Asp Lys Glu Pro Val Gly Glu Gly
2505            2510                2515 aaa ggc acg aaa gca ttt aag caa cct gca aag cgg aag ctg gac   7797
Lys Gly Thr Lys Ala Phe Lys Gln Pro Ala Lys Arg Lys Leu Asp
2520            2525                2530 gca gaa gat gta att ggc agc agg aga cag cca aga gca cct aag   7842
Ala Glu Asp Val Ile Gly Ser Arg Arg Gln Pro Arg Ala Pro Lys
2535            2540                2545 gaa aag gcc caa ccc ctg gaa gat ctg gcc agc ttc caa gag ctc   7887
Glu Lys Ala Gln Pro Leu Glu Asp Leu Ala Ser Phe Gln Glu Leu
2550            2555                2560 tct caa aca cca ggc cac act gag gaa ctg gca aat ggt gct gct   7932
Ser Gln Thr Pro Gly His Thr Glu Glu Leu Ala Asn Gly Ala Ala
2565            2570                2575 gat agc ttt aca agc gct cca aag caa aca cct gac agt gga aaa   7977
Asp Ser Phe Thr Ser Ala Pro Lys Gln Thr Pro Asp Ser Gly Lys
2580            2585                2590 cct cta aaa ata tcc aga aga gtt ctt cgg gcc cct aaa gta gaa   8022
Pro Leu Lys Ile Ser Arg Arg Val Leu Arg Ala Pro Lys Val Glu
```

```
                        2595                 2600                  2605
ccc  gtg  gga  gac  gtg  gta  agc  acc  aga  gac  cct  gta  aaa  tca  caa        8067
Pro  Val  Gly  Asp  Val  Val  Ser  Thr  Arg  Asp  Pro  Val  Lys  Ser  Gln
2610                     2615                      2620 agc  aaa  agc  aac  act  tcc  ctg  ccc  cca  ctg  ccc  ttc  aag  agg  gga        8112
Ser  Lys  Ser  Asn  Thr  Ser  Leu  Pro  Pro  Leu  Pro  Phe  Lys  Arg  Gly
2625                     2630                      2635 ggt  ggc  aaa  gat  gga  agc  gtc  acg  gga  acc  aag  agg  ctg  cgc  tgc        8157
Gly  Gly  Lys  Asp  Gly  Ser  Val  Thr  Gly  Thr  Lys  Arg  Leu  Arg  Cys
2640                     2645                      2650 atg  cca  gca  cca  gag  gaa  att  gtg  gag  gag  ctg  cca  gcc  agc  aag        8202
Met  Pro  Ala  Pro  Glu  Glu  Ile  Val  Glu  Glu  Leu  Pro  Ala  Ser  Lys
2655                     2660                      2665 aag  cag  agg  gtt  gct  ccc  agg  gca  aga  ggc  aaa  tca  tcc  gaa  ccc        8247
Lys  Gln  Arg  Val  Ala  Pro  Arg  Ala  Arg  Gly  Lys  Ser  Ser  Glu  Pro
2670                     2675                      2680 gtg  gtc  atc  atg  aag  aga  agt  ttg  agg  act  tct  gca  aaa  aga  att        8292
Val  Val  Ile  Met  Lys  Arg  Ser  Leu  Arg  Thr  Ser  Ala  Lys  Arg  Ile
2685                     2690                      2695 gaa  cct  gcg  gaa  gag  ctg  aac  agc  aac  gac  atg  aaa  acc  aac  aaa        8337
Glu  Pro  Ala  Glu  Glu  Leu  Asn  Ser  Asn  Asp  Met  Lys  Thr  Asn  Lys
2700                     2705                      2710 gag  gaa  cac  aaa  tta  caa  gac  tcg  gtc  cct  gaa  aat  aag  gga  ata        8382
Glu  Glu  His  Lys  Leu  Gln  Asp  Ser  Val  Pro  Glu  Asn  Lys  Gly  Ile
2715                     2720                      2725 tcc  ctg  cgc  tcc  aga  cgc  caa  aat  aag  act  gag  gca  gaa  cag  caa        8427
Ser  Leu  Arg  Ser  Arg  Arg  Gln  Asn  Lys  Thr  Glu  Ala  Glu  Gln  Gln
2730                     2735                      2740 ata  act  gag  gtc  ttt  gta  tta  gca  gaa  aga  ata  gaa  ata  aac  aga        8472
Ile  Thr  Glu  Val  Phe  Val  Leu  Ala  Glu  Arg  Ile  Glu  Ile  Asn  Arg
2745                     2750                      2755 aat  gaa  aag  aag  ccc  atg  aag  acc  tcc  cca  gag  atg  gac  att  cag        8517
Asn  Glu  Lys  Lys  Pro  Met  Lys  Thr  Ser  Pro  Glu  Met  Asp  Ile  Gln
2760                     2765                      2770 aat  cca  gat  gat  gga  gcc  cgg  aaa  ccc  ata  cct  aga  gac  aaa  gtc        8562
Asn  Pro  Asp  Asp  Gly  Ala  Arg  Lys  Pro  Ile  Pro  Arg  Asp  Lys  Val
2775                     2780                      2785 act  gag  aac  aaa  agg  tgc  ttg  agg  tct  gct  aga  cag  aat  gag  agc        8607
Thr  Glu  Asn  Lys  Arg  Cys  Leu  Arg  Ser  Ala  Arg  Gln  Asn  Glu  Ser
2790                     2795                      2800 tcc  cag  cct  aag  gtg  gca  gag  gag  agc  gga  ggg  cag  aag  agt  gcg        8652
Ser  Gln  Pro  Lys  Val  Ala  Glu  Glu  Ser  Gly  Gly  Gln  Lys  Ser  Ala
2805                     2810                      2815 aag  gtt  ctc  atg  cag  aat  cag  aaa  ggg  aaa  gga  gaa  gca  gga  aat        8697
Lys  Val  Leu  Met  Gln  Asn  Gln  Lys  Gly  Lys  Gly  Glu  Ala  Gly  Asn
2820                     2825                      2830 tca  gac  tcc  atg  tgc  ctg  aga  tca  aga  aag  aca  aaa  agc  cag  cct        8742
Ser  Asp  Ser  Met  Cys  Leu  Arg  Ser  Arg  Lys  Thr  Lys  Ser  Gln  Pro
2835                     2840                      2845 gca  gca  agc  act  ttg  gag  agc  aaa  tct  gtg  cag  aga  gta  acg  cgg        8787
Ala  Ala  Ser  Thr  Leu  Glu  Ser  Lys  Ser  Val  Gln  Arg  Val  Thr  Arg
2850                     2855                      2860 agt  gtc  aag  agg  tgt  gca  gaa  aat  cca  aag  aag  gct  gag  gac  aat        8832
Ser  Val  Lys  Arg  Cys  Ala  Glu  Asn  Pro  Lys  Lys  Ala  Glu  Asp  Asn
2865                     2870                      2875 gtg  tgt  gtc  aag  aaa  ata  aga  acc  aga  agt  cat  agg  gac  agt  gaa        8877
Val  Cys  Val  Lys  Lys  Ile  Arg  Thr  Arg  Ser  His  Arg  Asp  Ser  Glu
2880                     2885                      2890 gat  att  tga  cagaaaaatc  gaactgggaa  aaatataata  aagttagttt                   8926
```

Asp Ile
2895

| | | | | | |
|---|---|---|---|---|---|
| tgtgataagt | tctagtgcag | tttttgtcat | aaattacaag | tgaattctgt | aagtaaggct | 8986 |
| gtcagtctgc | ttaagggaag | aaaactttgg | atttgctggg | tctgaatcgg | cttcataaac | 9046 |
| tccactggga | gcactgctgg | gctcctggac | tgagaatagt | tgaacaccgg | gggctttgtg | 9106 |
| aaggagtctg | ggccaaggtt | tgccctcagc | tttgcagaat | gaagccttga | ggtctgtcac | 9166 |
| cacccacagc | caccctacag | cagccttaac | tgtgacactt | gccacactgt | gtcgtcgttt | 9226 |
| gtttgcctat | gtcctccagg | gcacggtggc | aggaacaact | atcctcgtct | gtcccaacac | 9286 |
| tgagcaggca | ctcggtaaac | acgaatgaat | ggatgagcgc | acggatgaat | ggagcttaca | 9346 |
| agatctgtct | ttccaatggc | cgggggcatt | tggtccccaa | attaaggcta | ttggacatct | 9406 |
| gcacaggaca | gtcctatttt | tgatgtcctt | tcctttctga | aaataaagtt | ttgtgctttg | 9466 |
| gagaatgact | cgtgagcaca | tctttaggga | ccaagagtga | ctttctgtaa | ggagtgactc | 9526 |
| gtggcttgcc | ttggtctctt | gggaatactt | ttctaactag | ggttgctctc | acctgagaca | 9586 |
| ttctccaccc | gcggaatctc | agggtcccag | gctgtgggcc | atcacgacct | caaactggct | 9646 |
| cctaatctcc | agctttcctg | tcattgaaag | cttcggaagt | ttactggctc | tgctcccgcc | 9706 |
| tgttttcttt | ctgactctat | ctggcagccc | gatgccaccc | agtacaggaa | gtgacaccag | 9766 |
| tactctgtaa | agcatcatca | tccttggaga | gactgagcac | tcagcacctt | cagccacgat | 9826 |
| ttcaggatcg | cttccttgtg | agccgctgcc | tccgaaatct | cctttgaagc | ccagacatct | 9886 |
| ttctccagct | tcagacttgt | agatataact | cgttcatctt | catttacttt | ccactttgcc | 9946 |
| ccctgtcctc | tctgtgttcc | ccaaatcaga | gaatagcccg | ccatccccca | ggtcacctgt | 10006 |
| ctggattcct | ccccattcac | ccaccttgcc | aggtgcaggt | gaggatggtg | caccagacag | 10066 |
| ggtagctgtc | ccccaaaatg | tgccctgtgc | gggcagtgcc | ctgtctccac | gtttgtttcc | 10126 |
| ccagtgtctg | gcggggagcc | aggtgacatc | ataaatactt | gctgaatgaa | tgcagaaatc | 10186 |
| agcggtactg | acttgtacta | tattggctgc | catgataggg | ttctcacagc | gtcatccatg | 10246 |
| atcgtaaggg | agaatgacat | tctgcttgag | ggagggaata | gaaaggggca | gggaggggac | 10306 |
| atctgagggc | ttcacagggc | tgcaaagggt | acaggattg | caccagggca | gaacagggga | 10366 |
| gggtgttcaa | ggaagagtgg | ctcttagcag | aggcactttg | gaaggtgtga | ggcataaatg | 10426 |
| cttccttcta | cgtaggccaa | cctcaaaact | ttcagtagga | atgttgctat | gatcaagttg | 10486 |
| ttctaacact | ttagacttag | tagtaattat | gaacctcaca | tagaaaaatt | tcatccagcc | 10546 |
| atatgcctgt | ggagtggaat | attctgttta | gtagaaaaat | cctttagagt | tcagctctaa | 10606 |
| ccagaaatct | tgctgaagta | tgtcagcacc | ttttctcacc | ctggtaagta | cagtatttca | 10666 |
| agagcacgct | aagggtggtt | ttcattttac | agggctgttg | atgatgggtt | aaaaatgttc | 10726 |
| atttaagggc | taccccgtg | tttaatagat | gaacaccact | tctacacaac | cctccttggt | 10786 |
| actgggggag | ggagagatct | gacaaatact | gcccattccc | ctaggctgac | tggatttgag | 10846 |
| aacaaatacc | cacccatttc | caccatggta | tggtaacttc | tctgagcttc | agtttccaag | 10906 |
| tgaatttcca | tgtaatagga | cattcccatt | aaatacaagc | tgttttact | ttttcgcctc | 10966 |
| ccagggcctg | tgggatctgg | tccccagcc | tctcttgggc | tttcttacac | taactctgta | 11026 |
| cctaccatct | cctgcctccc | ttaggcaggc | acctccaacc | accacacact | ccctgctgtt | 11086 |
| ttccctgcct | ggaactttcc | ctcctgcccc | accaagatca | tttcatccag | tcctgagctc | 11146 |
| agcttaaggg | aggcttcttg | cctgtgggtt | ccctcacccc | catgcctgtc | ctccaggctg | 11206 |

```
gggcaggttc ttagtttgcc tggaattgtt ctgtacctct ttgtagcacg tagtgttgtg    11266
gaaactaagc cactaattga gtttctggct cccctcctgg ggttgtaagt tttgttcatt    11326
catgagggcc gactgcattt cctggttact ctatcccagt gaccagccac aggagatgtc    11386
caataaagta tgtgatgaaa tggtcttaaa aaaaaaaaa a                         11427
```

```
<210> SEQ ID NO 68
<211> LENGTH: 2896
<212> TYPE: PRT
<213> ORGANISM: Homo sapiens

<400> SEQUENCE: 68

Met Trp Pro Thr Arg Arg Leu Val Thr Ile Lys Arg Ser Gly Val Asp
1               5                   10                  15

Gly Pro His Phe Pro Leu Ser Leu Ser Thr Cys Leu Phe Gly Arg Gly
            20                  25                  30

Ile Glu Cys Asp Ile Arg Ile Gln Leu Pro Val Val Ser Lys Gln His
        35                  40                  45

Cys Lys Ile Glu Ile His Glu Gln Glu Ala Ile Leu His Asn Phe Ser
    50                  55                  60

Ser Thr Asn Pro Thr Gln Val Asn Gly Ser Val Ile Asp Glu Pro Val
65                  70                  75                  80

Arg Leu Lys His Gly Asp Val Ile Thr Ile Asp Arg Ser Phe Arg
                85                  90                  95

Tyr Glu Asn Glu Ser Leu Gln Asn Gly Arg Lys Ser Thr Glu Phe Pro
                100                 105                 110

Arg Lys Ile Arg Glu Gln Glu Pro Ala Arg Arg Val Ser Arg Ser Ser
            115                 120                 125

Phe Ser Ser Asp Pro Asp Glu Ser Glu Gly Ile Pro Leu Lys Arg Arg
    130                 135                 140

Arg Val Ser Phe Gly Gly His Leu Arg Pro Glu Leu Phe Asp Glu Asn
145                 150                 155                 160

Leu Pro Pro Asn Thr Pro Leu Lys Arg Gly Glu Ala Pro Thr Lys Arg
                165                 170                 175

Lys Ser Leu Val Met His Thr Pro Pro Val Leu Lys Lys Ile Ile Lys
            180                 185                 190

Glu Gln Pro Gln Pro Ser Gly Lys Gln Glu Ser Gly Ser Glu Ile His
        195                 200                 205

Val Glu Val Lys Ala Gln Ser Leu Val Ile Ser Pro Pro Ala Pro Ser
    210                 215                 220

Pro Arg Lys Thr Pro Val Ala Ser Asp Gln Arg Arg Ser Cys Lys
225                 230                 235                 240

Thr Ala Pro Ala Ser Ser Ser Lys Ser Gln Thr Glu Val Pro Lys Arg
                245                 250                 255

Gly Gly Arg Lys Ser Gly Asn Leu Pro Ser Lys Arg Val Ser Ile Ser
            260                 265                 270

Arg Ser Gln His Asp Ile Leu Gln Met Ile Cys Ser Lys Arg Arg Ser
        275                 280                 285

Gly Ala Ser Glu Ala Asn Leu Ile Val Ala Lys Ser Trp Ala Asp Val
    290                 295                 300

Val Lys Leu Gly Ala Lys Gln Thr Gln Thr Lys Val Ile Lys His Gly
305                 310                 315                 320

Pro Gln Arg Ser Met Asn Lys Arg Gln Arg Arg Pro Ala Thr Pro Lys
                325                 330                 335
```

-continued

```
Lys Pro Val Gly Glu Val His Ser Gln Phe Ser Thr Gly His Ala Asn
            340                 345                 350

Ser Pro Cys Thr Ile Ile Ile Gly Lys Ala His Thr Glu Lys Val His
        355                 360                 365

Val Pro Ala Arg Pro Tyr Arg Val Leu Asn Asn Phe Ile Ser Asn Gln
    370                 375                 380

Lys Met Asp Phe Lys Glu Asp Leu Ser Gly Ile Ala Glu Met Phe Lys
385                 390                 395                 400

Thr Pro Val Lys Glu Gln Pro Gln Leu Thr Ser Cys His Ile Ala
            405                 410                 415

Ile Ser Asn Ser Glu Asn Leu Leu Gly Lys Gln Phe Gln Gly Thr Asp
            420                 425                 430

Ser Gly Glu Glu Pro Leu Leu Pro Thr Ser Glu Ser Phe Gly Gly Asn
        435                 440                 445

Val Phe Phe Ser Ala Gln Asn Ala Ala Lys Gln Pro Ser Asp Lys Cys
    450                 455                 460

Ser Ala Ser Pro Pro Leu Arg Arg Gln Cys Ile Arg Glu Asn Gly Asn
465                 470                 475                 480

Val Ala Lys Thr Pro Arg Asn Thr Tyr Lys Met Thr Ser Leu Glu Thr
            485                 490                 495

Lys Thr Ser Asp Thr Glu Thr Glu Pro Ser Lys Thr Val Ser Thr Ala
            500                 505                 510

Asn Arg Ser Gly Arg Ser Thr Glu Phe Arg Asn Ile Gln Lys Leu Pro
        515                 520                 525

Val Glu Ser Lys Ser Glu Thr Asn Thr Glu Ile Val Glu Cys Ile
    530                 535                 540

Leu Lys Arg Gly Gln Lys Ala Thr Leu Leu Gln Gln Arg Arg Glu Gly
545                 550                 555                 560

Glu Met Lys Glu Ile Glu Arg Pro Phe Glu Thr Tyr Lys Glu Asn Ile
            565                 570                 575

Glu Leu Lys Glu Asn Asp Glu Lys Met Lys Ala Met Lys Arg Ser Arg
        580                 585                 590

Thr Trp Gly Gln Lys Cys Ala Pro Met Ser Asp Leu Thr Asp Leu Lys
    595                 600                 605

Ser Leu Pro Asp Thr Glu Leu Met Lys Asp Thr Ala Arg Gly Gln Asn
610                 615                 620

Leu Leu Gln Thr Gln Asp His Ala Lys Ala Pro Lys Ser Glu Lys Gly
625                 630                 635                 640

Lys Ile Thr Lys Met Pro Cys Gln Ser Leu Gln Pro Glu Pro Ile Asn
            645                 650                 655

Thr Pro Thr His Thr Lys Gln Gln Leu Lys Ala Ser Leu Gly Lys Val
        660                 665                 670

Gly Val Lys Glu Glu Leu Leu Ala Val Gly Lys Phe Thr Arg Thr Ser
    675                 680                 685

Gly Glu Thr Thr His Thr His Arg Glu Pro Ala Gly Asp Gly Lys Ser
690                 695                 700

Ile Arg Thr Phe Lys Glu Ser Pro Lys Gln Ile Leu Asp Pro Ala Ala
705                 710                 715                 720

Arg Val Thr Gly Met Lys Lys Trp Pro Arg Thr Pro Lys Glu Glu Ala
            725                 730                 735

Gln Ser Leu Glu Asp Leu Ala Gly Phe Lys Glu Leu Phe Gln Thr Pro
        740                 745                 750

Gly Pro Ser Glu Glu Ser Met Thr Asp Glu Lys Thr Thr Lys Ile Ala
```

```
              755                 760                 765
Cys Lys Ser Pro Pro Glu Ser Val Asp Thr Pro Thr Ser Thr Lys
770                 775                 780
Gln Trp Pro Lys Arg Ser Leu Arg Lys Ala Asp Val Glu Glu Phe
785                 790                 795                 800
Leu Ala Leu Arg Lys Leu Thr Pro Ser Ala Gly Lys Ala Met Leu Thr
                805                 810                 815
Pro Lys Pro Ala Gly Asp Glu Lys Asp Ile Lys Ala Phe Met Gly
820                 825                 830
Thr Pro Val Gln Lys Leu Asp Leu Ala Gly Thr Leu Pro Gly Ser Lys
                835                 840                 845
Arg Gln Leu Gln Thr Pro Lys Glu Lys Ala Gln Ala Leu Glu Asp Leu
850                 855                 860
Ala Gly Phe Lys Glu Leu Phe Gln Thr Pro Gly His Thr Glu Glu Leu
865                 870                 875                 880
Val Ala Ala Gly Lys Thr Thr Lys Ile Pro Cys Asp Ser Pro Gln Ser
                885                 890                 895
Asp Pro Val Asp Thr Pro Thr Ser Thr Lys Gln Arg Pro Lys Arg Ser
                900                 905                 910
Ile Arg Lys Ala Asp Val Glu Gly Glu Leu Leu Ala Cys Arg Asn Leu
                915                 920                 925
Met Pro Ser Ala Gly Lys Ala Met His Thr Pro Lys Pro Ser Val Gly
930                 935                 940
Glu Glu Lys Asp Ile Ile Ile Phe Val Gly Thr Pro Val Gln Lys Leu
945                 950                 955                 960
Asp Leu Thr Glu Asn Leu Thr Gly Ser Lys Arg Arg Pro Gln Thr Pro
                965                 970                 975
Lys Glu Glu Ala Gln Ala Leu Glu Asp Leu Thr Gly Phe Lys Glu Leu
                980                 985                 990
Phe Gln Thr Pro Gly His Thr Glu Glu Ala Val Ala Ala Gly Lys Thr
                995                 1000                1005
Thr Lys Met Pro Cys Glu Ser Pro Pro Glu Ser Ala Asp Thr
1010                1015                1020
Pro Thr Ser Thr Arg Arg Gln Pro Lys Thr Pro Leu Glu Lys Arg
1025                1030                1035
Asp Val Gln Lys Glu Leu Ser Ala Leu Lys Lys Leu Thr Gln Thr
1040                1045                1050
Ser Gly Glu Thr Thr His Thr Asp Lys Val Pro Gly Gly Glu Asp
1055                1060                1065
Lys Ser Ile Asn Ala Phe Arg Glu Thr Ala Lys Gln Lys Leu Asp
1070                1075                1080
Pro Ala Ala Ser Val Thr Gly Ser Lys Arg His Pro Lys Thr Lys
1085                1090                1095
Glu Lys Ala Gln Pro Leu Glu Asp Leu Ala Gly Leu Lys Glu Leu
1100                1105                1110
Phe Gln Thr Pro Val Cys Thr Asp Lys Pro Thr Thr His Glu Lys
1115                1120                1125
Thr Thr Lys Ile Ala Cys Arg Ser Gln Pro Asp Pro Val Asp Thr
1130                1135                1140
Pro Thr Ser Ser Lys Pro Gln Ser Lys Arg Ser Leu Arg Lys Val
1145                1150                1155
Asp Val Glu Glu Glu Phe Phe Ala Leu Arg Lys Arg Thr Pro Ser
1160                1165                1170
```

```
Ala Gly Lys Ala Met His Thr Pro Lys Pro Ala Val Ser Gly Glu
    1175            1180            1185

Lys Asn Ile Tyr Ala Phe Met Gly Thr Pro Val Gln Lys Leu Asp
    1190            1195            1200

Leu Thr Glu Asn Leu Thr Gly Ser Lys Arg Arg Leu Gln Thr Pro
    1205            1210            1215

Lys Glu Lys Ala Gln Ala Leu Glu Asp Leu Ala Gly Phe Lys Glu
    1220            1225            1230

Leu Phe Gln Thr Arg Gly His Thr Glu Glu Ser Met Thr Asn Asp
    1235            1240            1245

Lys Thr Ala Lys Val Ala Cys Lys Ser Ser Gln Pro Asp Pro Asp
    1250            1255            1260

Lys Asn Pro Ala Ser Ser Lys Arg Arg Leu Lys Thr Ser Leu Gly
    1265            1270            1275

Lys Val Gly Val Lys Glu Glu Leu Leu Ala Val Gly Lys Leu Thr
    1280            1285            1290

Gln Thr Ser Gly Glu Thr Thr His Thr His Thr Glu Pro Thr Gly
    1295            1300            1305

Asp Gly Lys Ser Met Lys Ala Phe Met Glu Ser Pro Lys Gln Ile
    1310            1315            1320

Leu Asp Ser Ala Ala Ser Leu Thr Gly Ser Lys Arg Gln Leu Arg
    1325            1330            1335

Thr Pro Lys Gly Lys Ser Glu Val Pro Glu Asp Leu Ala Gly Phe
    1340            1345            1350

Ile Glu Leu Phe Gln Thr Pro Ser His Thr Lys Glu Ser Met Thr
    1355            1360            1365

Asn Glu Lys Thr Thr Lys Val Ser Tyr Arg Ala Ser Gln Pro Asp
    1370            1375            1380

Leu Val Asp Thr Pro Thr Ser Ser Lys Pro Gln Pro Lys Arg Ser
    1385            1390            1395

Leu Arg Lys Ala Asp Thr Glu Glu Glu Phe Leu Ala Phe Arg Lys
    1400            1405            1410

Gln Thr Pro Ser Ala Gly Lys Ala Met His Thr Pro Lys Pro Ala
    1415            1420            1425

Val Gly Glu Glu Lys Asp Ile Asn Thr Phe Leu Gly Thr Pro Val
    1430            1435            1440

Gln Lys Leu Asp Gln Pro Gly Asn Leu Pro Gly Ser Asn Arg Arg
    1445            1450            1455

Leu Gln Thr Arg Lys Glu Lys Ala Gln Ala Leu Glu Glu Leu Thr
    1460            1465            1470

Gly Phe Arg Glu Leu Phe Gln Thr Pro Cys Thr Asp Asn Pro Thr
    1475            1480            1485

Thr Asp Glu Lys Thr Thr Lys Lys Ile Leu Cys Lys Ser Pro Gln
    1490            1495            1500

Ser Asp Pro Ala Asp Thr Pro Thr Asn Thr Lys Gln Arg Pro Lys
    1505            1510            1515

Arg Ser Leu Lys Lys Ala Asp Val Glu Glu Glu Phe Leu Ala Phe
    1520            1525            1530

Arg Lys Leu Thr Pro Ser Ala Gly Lys Ala Met His Thr Pro Lys
    1535            1540            1545

Ala Ala Val Gly Glu Glu Lys Asp Ile Asn Thr Phe Val Gly Thr
    1550            1555            1560
```

```
Pro Val Glu Lys Leu Asp Leu Leu Gly Asn Leu Pro Gly Ser Lys
    1565            1570            1575

Arg Arg Pro Gln Thr Pro Lys Glu Lys Ala Lys Ala Leu Glu Asp
    1580            1585            1590

Leu Ala Gly Phe Lys Glu Leu Phe Gln Thr Pro Gly His Thr Glu
    1595            1600            1605

Glu Ser Met Thr Asp Asp Lys Ile Thr Glu Val Ser Cys Lys Ser
    1610            1615            1620

Pro Gln Pro Asp Pro Val Lys Thr Pro Thr Ser Ser Lys Gln Arg
    1625            1630            1635

Leu Lys Ile Ser Leu Gly Lys Val Gly Val Lys Glu Glu Val Leu
    1640            1645            1650

Pro Val Gly Lys Leu Thr Gln Thr Ser Gly Lys Thr Thr Gln Thr
    1655            1660            1665

His Arg Glu Thr Ala Gly Asp Gly Lys Ser Ile Lys Ala Phe Lys
    1670            1675            1680

Glu Ser Ala Lys Gln Met Leu Asp Pro Ala Asn Tyr Gly Thr Gly
    1685            1690            1695

Met Glu Arg Trp Pro Arg Thr Pro Lys Glu Glu Ala Gln Ser Leu
    1700            1705            1710

Glu Asp Leu Ala Gly Phe Lys Glu Leu Phe Gln Thr Pro Asp His
    1715            1720            1725

Thr Glu Glu Ser Thr Thr Asp Asp Lys Thr Thr Lys Ile Ala Cys
    1730            1735            1740

Lys Ser Pro Pro Pro Glu Ser Met Asp Thr Pro Thr Ser Thr Arg
    1745            1750            1755

Arg Arg Pro Lys Thr Pro Leu Gly Lys Arg Asp Ile Val Glu Glu
    1760            1765            1770

Leu Ser Ala Leu Lys Gln Leu Thr Gln Thr Thr His Thr Asp Lys
    1775            1780            1785

Val Pro Gly Asp Glu Asp Lys Gly Ile Asn Val Phe Arg Glu Thr
    1790            1795            1800

Ala Lys Gln Lys Leu Asp Pro Ala Ala Ser Val Thr Gly Ser Lys
    1805            1810            1815

Arg Gln Pro Arg Thr Pro Lys Gly Lys Ala Gln Pro Leu Glu Asp
    1820            1825            1830

Leu Ala Gly Leu Lys Glu Leu Phe Gln Thr Pro Ile Cys Thr Asp
    1835            1840            1845

Lys Pro Thr Thr His Glu Lys Thr Thr Lys Ile Ala Cys Arg Ser
    1850            1855            1860

Pro Gln Pro Asp Pro Val Gly Thr Pro Thr Ile Phe Lys Pro Gln
    1865            1870            1875

Ser Lys Arg Ser Leu Arg Lys Ala Asp Val Glu Glu Glu Ser Leu
    1880            1885            1890

Ala Leu Arg Lys Arg Thr Pro Ser Val Gly Lys Ala Met Asp Thr
    1895            1900            1905

Pro Lys Pro Ala Gly Gly Asp Glu Lys Asp Met Lys Ala Phe Met
    1910            1915            1920

Gly Thr Pro Val Gln Lys Leu Asp Leu Pro Gly Asn Leu Pro Gly
    1925            1930            1935

Ser Lys Arg Trp Pro Gln Thr Pro Lys Glu Lys Ala Gln Ala Leu
    1940            1945            1950

Glu Asp Leu Ala Gly Phe Lys Glu Leu Phe Gln Thr Pro Gly Thr
```

-continued

```
          1955                1960                1965

Asp Lys Pro Thr Thr Asp Glu Lys Thr Thr Lys Ile Ala Cys Lys
        1970                1975                1980

Ser Pro Gln Pro Asp Pro Val Asp Thr Pro Ala Ser Thr Lys Gln
        1985                1990                1995

Arg Pro Lys Arg Asn Leu Arg Lys Ala Asp Val Glu Glu Glu Phe
        2000                2005                2010

Leu Ala Leu Arg Lys Arg Thr Pro Ser Ala Gly Lys Ala Met Asp
        2015                2020                2025

Thr Pro Lys Pro Ala Val Ser Asp Glu Lys Asn Ile Asn Thr Phe
        2030                2035                2040

Val Glu Thr Pro Val Gln Lys Leu Asp Leu Leu Gly Asn Leu Pro
        2045                2050                2055

Gly Ser Lys Arg Gln Pro Gln Thr Pro Lys Glu Lys Ala Glu Ala
        2060                2065                2070

Leu Glu Asp Leu Val Gly Phe Lys Glu Leu Phe Gln Thr Pro Gly
        2075                2080                2085

His Thr Glu Glu Ser Met Thr Asp Asp Lys Ile Thr Glu Val Ser
        2090                2095                2100

Cys Lys Ser Pro Gln Pro Glu Ser Phe Lys Thr Ser Arg Ser Ser
        2105                2110                2115

Lys Gln Arg Leu Lys Ile Pro Leu Val Lys Val Asp Met Lys Glu
        2120                2125                2130

Glu Pro Leu Ala Val Ser Lys Leu Thr Arg Thr Ser Gly Glu Thr
        2135                2140                2145

Thr Gln Thr His Thr Glu Pro Thr Gly Asp Ser Lys Ser Ile Lys
        2150                2155                2160

Ala Phe Lys Glu Ser Pro Lys Gln Ile Leu Asp Pro Ala Ala Ser
        2165                2170                2175

Val Thr Gly Ser Arg Arg Gln Leu Arg Thr Arg Lys Glu Lys Ala
        2180                2185                2190

Arg Ala Leu Glu Asp Leu Val Asp Phe Lys Glu Leu Phe Ser Ala
        2195                2200                2205

Pro Gly His Thr Glu Glu Ser Met Thr Ile Asp Lys Asn Thr Lys
        2210                2215                2220

Ile Pro Cys Lys Ser Pro Pro Glu Leu Thr Asp Thr Ala Thr
        2225                2230                2235

Ser Thr Lys Arg Cys Pro Lys Thr Arg Pro Arg Lys Glu Val Lys
        2240                2245                2250

Glu Glu Leu Ser Ala Val Glu Arg Leu Thr Gln Thr Ser Gly Gln
        2255                2260                2265

Ser Thr His Thr His Lys Glu Pro Ala Ser Gly Asp Glu Gly Ile
        2270                2275                2280

Lys Val Leu Lys Gln Arg Ala Lys Lys Lys Pro Asn Pro Val Glu
        2285                2290                2295

Glu Glu Pro Ser Arg Arg Arg Pro Arg Ala Pro Lys Glu Lys Ala
        2300                2305                2310

Gln Pro Leu Glu Asp Leu Ala Gly Phe Thr Glu Leu Ser Glu Thr
        2315                2320                2325

Ser Gly His Thr Gln Glu Ser Leu Thr Ala Gly Lys Ala Thr Lys
        2330                2335                2340

Ile Pro Cys Glu Ser Pro Pro Leu Glu Val Val Asp Thr Thr Ala
        2345                2350                2355
```

-continued

```
Ser Thr Lys Arg His Leu Arg Thr Arg Val Gln Lys Val Gln Val
    2360                2365                2370
Lys Glu Glu Pro Ser Ala Val Lys Phe Thr Gln Thr Ser Gly Glu
    2375                2380                2385
Thr Thr Asp Ala Asp Lys Glu Pro Ala Gly Glu Asp Lys Gly Ile
    2390                2395                2400
Lys Ala Leu Lys Glu Ser Ala Lys Gln Thr Pro Ala Pro Ala Ala
    2405                2410                2415
Ser Val Thr Gly Ser Arg Arg Arg Pro Arg Ala Pro Arg Glu Ser
    2420                2425                2430
Ala Gln Ala Ile Glu Asp Leu Ala Gly Phe Lys Asp Pro Ala Ala
    2435                2440                2445
Gly His Thr Glu Glu Ser Met Thr Asp Asp Lys Thr Thr Lys Ile
    2450                2455                2460
Pro Cys Lys Ser Ser Pro Glu Leu Glu Asp Thr Ala Thr Ser Ser
    2465                2470                2475
Lys Arg Arg Pro Arg Thr Arg Ala Gln Lys Val Glu Val Lys Glu
    2480                2485                2490
Glu Leu Leu Ala Val Gly Lys Leu Thr Gln Thr Ser Gly Glu Thr
    2495                2500                2505
Thr His Thr Asp Lys Glu Pro Val Gly Glu Gly Lys Gly Thr Lys
    2510                2515                2520
Ala Phe Lys Gln Pro Ala Lys Arg Lys Leu Asp Ala Glu Asp Val
    2525                2530                2535
Ile Gly Ser Arg Arg Gln Pro Arg Ala Pro Lys Glu Lys Ala Gln
    2540                2545                2550
Pro Leu Glu Asp Leu Ala Ser Phe Gln Glu Leu Ser Gln Thr Pro
    2555                2560                2565
Gly His Thr Glu Glu Leu Ala Asn Gly Ala Ala Asp Ser Phe Thr
    2570                2575                2580
Ser Ala Pro Lys Gln Thr Pro Asp Ser Gly Lys Pro Leu Lys Ile
    2585                2590                2595
Ser Arg Arg Val Leu Arg Ala Pro Lys Val Glu Pro Val Gly Asp
    2600                2605                2610
Val Val Ser Thr Arg Asp Pro Val Lys Ser Gln Ser Lys Ser Asn
    2615                2620                2625
Thr Ser Leu Pro Pro Leu Pro Phe Lys Arg Gly Gly Gly Lys Asp
    2630                2635                2640
Gly Ser Val Thr Gly Thr Lys Arg Leu Arg Cys Met Pro Ala Pro
    2645                2650                2655
Glu Glu Ile Val Glu Glu Leu Pro Ala Ser Lys Lys Gln Arg Val
    2660                2665                2670
Ala Pro Arg Ala Arg Gly Lys Ser Ser Glu Pro Val Val Ile Met
    2675                2680                2685
Lys Arg Ser Leu Arg Thr Ser Ala Lys Arg Ile Glu Pro Ala Glu
    2690                2695                2700
Glu Leu Asn Ser Asn Asp Met Lys Thr Asn Lys Glu Glu His Lys
    2705                2710                2715
Leu Gln Asp Ser Val Pro Glu Asn Lys Gly Ile Ser Leu Arg Ser
    2720                2725                2730
Arg Arg Gln Asn Lys Thr Glu Ala Glu Gln Gln Ile Thr Glu Val
    2735                2740                2745
```

```
Phe Val Leu Ala Glu Arg Ile Glu Ile Asn Arg Asn Glu Lys Lys
        2750            2755            2760

Pro Met Lys Thr Ser Pro Glu Met Asp Ile Gln Asn Pro Asp Asp
        2765            2770            2775

Gly Ala Arg Lys Pro Ile Pro Arg Asp Lys Val Thr Glu Asn Lys
        2780            2785            2790

Arg Cys Leu Arg Ser Ala Arg Gln Asn Glu Ser Ser Gln Pro Lys
        2795            2800            2805

Val Ala Glu Glu Ser Gly Gly Gln Lys Ser Ala Lys Val Leu Met
        2810            2815            2820

Gln Asn Gln Lys Gly Lys Gly Glu Ala Gly Asn Ser Asp Ser Met
        2825            2830            2835

Cys Leu Arg Ser Arg Lys Thr Lys Ser Gln Pro Ala Ala Ser Thr
        2840            2845            2850

Leu Glu Ser Lys Ser Val Gln Arg Val Thr Arg Ser Val Lys Arg
        2855            2860            2865

Cys Ala Glu Asn Pro Lys Lys Ala Glu Asp Asn Val Cys Val Lys
        2870            2875            2880

Lys Ile Arg Thr Arg Ser His Arg Asp Ser Glu Asp Ile
        2885            2890            2895

<210> SEQ ID NO 69
<211> LENGTH: 4022
<212> TYPE: DNA
<213> ORGANISM: Homo sapiens
<220> FEATURE:
<221> NAME/KEY: CDS
<222> LOCATION: (508)..(2316)

<400> SEQUENCE: 69 ataatctcc gctcccagac tactccgttc ctccggattt cgatccccct tttctatct     60 gtcaatcagc gccgcctttg aactgaaaag ctctcagtct aacttcaact cactcaaatc   120
cgagcggcac gagcacctcc tgtatcttcg gcttcccccc cccctttgctc tttatatctg  180 acttcttgtt gttgttggtg ttttttttt ttttaccccc cttttttatt tattattttt    240
ttgcacattg atcggatcct tgggaacgag agaaaaaaga aacccaaact cacgcgtgca   300
gaagatctcc cccccttcc cctcccctcc tccctctttt ccctccccca ggagaaaaag    360
acccccaagc agaaaaaagt tcaccttgga ctcgtctttt tcttgcaata ttttttgggg   420
gggcaaaact ttttgggggt gattttttt ggcttttctt cctccttcat ttttcttcca    480
aaattgctgc tggtgggtga aaaaaaa atg ccg cag ctg aac ggc ggt gga ggg  534
                                Met Pro Gln Leu Asn Gly Gly Gly Gly
                                 1               5 gat gac cta ggc gcc aac gac gaa ctg att tcc ttc aaa gac gag ggc    582
Asp Asp Leu Gly Ala Asn Asp Glu Leu Ile Ser Phe Lys Asp Glu Gly
 10              15                  20                  25 gaa cag gag gag aag agc tcc gaa aac tcc tcg gca gag agg gat tta   630
Glu Gln Glu Glu Lys Ser Ser Glu Asn Ser Ser Ala Glu Arg Asp Leu
         30                  35                  40 gct gat gtc aaa tcg tct cta gtc aat gaa tca gaa acg aat caa aac   678
Ala Asp Val Lys Ser Ser Leu Val Asn Glu Ser Glu Thr Asn Gln Asn
             45                  50                  55 agc tcc tcc gat tcc gag gcg gaa aga cgg cct ccg cct cgc tcc gaa   726
Ser Ser Ser Asp Ser Glu Ala Glu Arg Arg Pro Pro Pro Arg Ser Glu
         60                  65                  70 agt ttc cga gac aaa tcc cgg gaa agt ttg gaa gaa gcg gcc aag agg   774
Ser Phe Arg Asp Lys Ser Arg Glu Ser Leu Glu Glu Ala Ala Lys Arg
```

```
            75                  80                  85
caa gat gga ggg ctc ttt aag ggg cca ccg tat ccc ggc tac ccc ttc     822
Gln Asp Gly Gly Leu Phe Lys Gly Pro Pro Tyr Pro Gly Tyr Pro Phe
 90                  95                 100                 105 atc atg atc ccc gac ctg acg agc ccc tac ctc ccc aac gga tcg ctc     870
Ile Met Ile Pro Asp Leu Thr Ser Pro Tyr Leu Pro Asn Gly Ser Leu
                    110                 115                 120 tcg ccc acc gcc cga acc ctc cat ttt cag tcc ggc agc aca cat tac     918
Ser Pro Thr Ala Arg Thr Leu His Phe Gln Ser Gly Ser Thr His Tyr
                125                 130                 135 tct gcg tac aaa acg att gaa cac cag att gca gtt cag tat ctc cag     966
Ser Ala Tyr Lys Thr Ile Glu His Gln Ile Ala Val Gln Tyr Leu Gln
            140                 145                 150 atg aaa tgg cca ctg ctt gat gtc cag gca ggg agc ctc cag agt aga    1014
Met Lys Trp Pro Leu Leu Asp Val Gln Ala Gly Ser Leu Gln Ser Arg
            155                 160                 165 caa gcc ctc aag gat gcc cgg tcc cca tca ccg gca cac att gtc tct    1062
Gln Ala Leu Lys Asp Ala Arg Ser Pro Ser Pro Ala His Ile Val Ser
170                 175                 180                 185 aac aaa gtg cca gtg gtg cag cac cct cac cat gtc cac ccc ctc acg    1110
Asn Lys Val Pro Val Val Gln His Pro His His Val His Pro Leu Thr
                190                 195                 200 cct ctt atc acg tac agc aat gaa cac ttc acg ccg gga aac cca cct    1158
Pro Leu Ile Thr Tyr Ser Asn Glu His Phe Thr Pro Gly Asn Pro Pro
                205                 210                 215 cca cac tta cca gcc gac gta gac ccc aaa aca gga atc cca cgg cct    1206
Pro His Leu Pro Ala Asp Val Asp Pro Lys Thr Gly Ile Pro Arg Pro
                220                 225                 230 ccg cac cct cca gat ata tcc ccg tat tac cca cta tcg cct ggc acc    1254
Pro His Pro Pro Asp Ile Ser Pro Tyr Tyr Pro Leu Ser Pro Gly Thr
            235                 240                 245 gta gga caa atc ccc cat ccg cta gga tgg tta gta cca cag caa ggt    1302
Val Gly Gln Ile Pro His Pro Leu Gly Trp Leu Val Pro Gln Gln Gly
250                 255                 260                 265 caa cca gtg tac cca atc acg aca gga gga ttc aga cac ccc tac ccc    1350
Gln Pro Val Tyr Pro Ile Thr Thr Gly Gly Phe Arg His Pro Tyr Pro
                270                 275                 280 aca gct ctg acc gtc aat gct tcc atg tcc agg ttc cct ccc cat atg    1398
Thr Ala Leu Thr Val Asn Ala Ser Met Ser Arg Phe Pro Pro His Met
            285                 290                 295 gtc cca cca cat cat acg cta cac acg acg ggc att ccg cat ccg gcc    1446
Val Pro Pro His His Thr Leu His Thr Thr Gly Ile Pro His Pro Ala
            300                 305                 310 ata gtc aca cca aca gtc aaa cag gaa tcg tcc cag agt gat gtc ggc    1494
Ile Val Thr Pro Thr Val Lys Gln Glu Ser Ser Gln Ser Asp Val Gly
            315                 320                 325 tca ctc cat agt tca aag cat cag gac tcc aaa aag gaa gaa gaa aag    1542
Ser Leu His Ser Ser Lys His Gln Asp Ser Lys Lys Glu Glu Glu Lys
330                 335                 340                 345 aag aag ccc cac ata aag aaa cct ctt aat gca ttc atg ttg tat atg    1590
Lys Lys Pro His Ile Lys Lys Pro Leu Asn Ala Phe Met Leu Tyr Met
                350                 355                 360 aag gaa atg aga gca aag gtc gta gct gag tgc acg ttg aaa gaa agc    1638
Lys Glu Met Arg Ala Lys Val Val Ala Glu Cys Thr Leu Lys Glu Ser
            365                 370                 375 gcg gcc atc aac cag atc ctt ggg cgg agg tgg cat gca ctg tcc aga    1686
Ala Ala Ile Asn Gln Ile Leu Gly Arg Arg Trp His Ala Leu Ser Arg
            380                 385                 390 gaa gag caa gcg aaa tac tac gag ctg gcc cgg aag gag cga cag ctt    1734
```

```
              Glu Glu Gln Ala Lys Tyr Tyr Glu Leu Ala Arg Lys Glu Arg Gln Leu
                  395                 400                 405 cat atg caa ctg tac ccc ggc tgg tcc gcg cgg gat aac tat gga aag          1782
His Met Gln Leu Tyr Pro Gly Trp Ser Ala Arg Asp Asn Tyr Gly Lys
410                 415                 420                 425 aag aag aag agg aaa agg gac aag cag ccg gga gag acc aat gat gca          1830
Lys Lys Lys Arg Lys Arg Asp Lys Gln Pro Gly Glu Thr Asn Asp Ala
                430                 435                 440 aat act cca aag aag tgt cgg gca ctg ttc ggg ctt gac cga cag act          1878
Asn Thr Pro Lys Lys Cys Arg Ala Leu Phe Gly Leu Asp Arg Gln Thr
            445                 450                 455 tta tgg tgc aaa ccg tgc agg aga aaa aaa aag tgc gtt cgc tac ata          1926
Leu Trp Cys Lys Pro Cys Arg Arg Lys Lys Lys Cys Val Arg Tyr Ile
        460                 465                 470 caa ggt gaa ggc agc tgc ctc agc cca ccc tct tca gat gga agc tta          1974
Gln Gly Glu Gly Ser Cys Leu Ser Pro Pro Ser Ser Asp Gly Ser Leu
    475                 480                 485 cta gat tcg cct ccc ccc tcc ccg aac ctg cta ggc tcc cct ccc cga          2022
Leu Asp Ser Pro Pro Pro Ser Pro Asn Leu Leu Gly Ser Pro Pro Arg
490                 495                 500                 505 gac gcc aag tca cag act gag cag acc cag cct ctg tcg ctg tcc ctg          2070
Asp Ala Lys Ser Gln Thr Glu Gln Thr Gln Pro Leu Ser Leu Ser Leu
                510                 515                 520 aag ccc gac ccc ctg gcc cac ctg tcc atg atg cct ccg cca ccc gcc          2118
Lys Pro Asp Pro Leu Ala His Leu Ser Met Met Pro Pro Pro Pro Ala
            525                 530                 535 ctc ctg ctc gct gag gcc acc cac aag gcc tcc gcc ctc tgt ccc aac          2166
Leu Leu Leu Ala Glu Ala Thr His Lys Ala Ser Ala Leu Cys Pro Asn
        540                 545                 550 ggg gcc ctg gac ctg ccc cca gcc gct ttg cag cct gcc gcc ccc tcc          2214
Gly Ala Leu Asp Leu Pro Pro Ala Ala Leu Gln Pro Ala Ala Pro Ser
    555                 560                 565 tca tca att gca cag ccg tcg act tct tcc tta cat tcc cac agc tcc          2262
Ser Ser Ile Ala Gln Pro Ser Thr Ser Ser Leu His Ser His Ser Ser
570                 575                 580                 585 ctg gcc ggg acc cag ccc cag ccg ctg tcg ctc gtc acc aag tct tta          2310
Leu Ala Gly Thr Gln Pro Gln Pro Leu Ser Leu Val Thr Lys Ser Leu
                590                 595                 600 gaa tag ctttagcgtc gtgaacccg ctgctttgtt tatggttttg tttcactttt           2366
Glu cttaatttgc cccccacccc caccttgaaa ggttttgttt tgtactctct taattttgtg       2426
ccatgtggct acattagttg atgtttatcg agttcattgg tcaatatttg acccattctt       2486
atttcaattt ctccttttaa atatgtagat gagagaagaa cctcatgatt ctaccaaaat       2546
ttttatcaac agctgtttaa agtctttgta gcgtttaaaa aatatatata tatacataac       2606
tgttatgtag ttcggatagc ttagttttaa aagactgatt aaaaaacaaa aagaaaaaaa       2666
aagcaatttt gaagcagccc tccagaagga gttggttctg tattatttgt attaaatacg       2726
agcttgcgaa ccaatcattt tacatctggt ttttaaaccg taagggcacc atgaatgcag       2786
tgccgttact ttttttttt ttttctgtgt gaaacaactc ttattgtgat gttacttgtt        2846
attgtttaaa tgtacagaaa caaagggtaa aaatgtgtta ataccttg ttccatggtg         2906 ttgttctttt ggggggaggg gacgctactc aacacttaat agaatcacaa cgctgttggg      2966
ccagtagtat ttattgcttt agagattgct tgtcgtacct gtatgtcgtc ccttttaaa       3026 tatgttttcc ttttcttga aactgtataa agttttttc cccctagca taagcatctt         3086 atatataaca actcatttgt acaaggtttt taagtttata tataaaatgt gtatatatat      3146
```

```
ttttgtttcc ccttttttgac ttttttttttt ctgtatgaaa cccagatgtc accaaatgga   3206
cattaatagt tgcattaagg atcagtagca ttaacaaaag ttgctttaaa agccattatg   3266
taaaacaaga cttgaaaatg agtgagggaa ttttagcgac actgtctgag cagcagtggg   3326
aaccatcttc gtttcccctt tgaactccca gtgggatgcc ctaccctgcg cccttaggac   3386
ccggactgac cgtgtacaaa actttacgtg ccaaaattct cagtgaattt agctttctcc   3446 ctcttttga tgctgtaatt tttgttcatc atgttttgct gtgatgttac ataggtagat   3506
ttgtatgtag ttttaatgtc acctataaca aaatgtgttt ggtagcagat tgtccagaaa   3566
gcattttaaa tgaagaggta taaacccta agggccaaaa ttctgtatat tagattactc   3626
ttaaacgaaa aaccagctgc cgcttttatg tacacatatt acatacgagt aggcagcaga   3686
cttaaaaaat aaaaaaaacc taggcatgtt gatgttgcaa aatgctgtat aaagctgaaa   3746
cctgttcatt cagtgccatt gtagttgaca tgaagcgatt gtaaaactgt ctccgatttt   3806
tctctggttt attaaaatgc taactataac attttttgtg aatactttga atgtttccta   3866
acagttgtga tgttactgtt ccgttttatg ctcttattcc aagttcattt ttaatggttt   3926
ggaagccatt tttgtaatga ataaatgttc atgctgtaca gtatctgtag catgccgttc   3986
tggattaata aaagcaactt agtatgtgca gataaa                              4022
```

<210> SEQ ID NO 70
<211> LENGTH: 602
<212> TYPE: PRT
<213> ORGANISM: Homo sapiens

<400> SEQUENCE: 70

```
Met Pro Gln Leu Asn Gly Gly Gly Asp Asp Leu Gly Ala Asn Asp
1               5                   10                  15

Glu Leu Ile Ser Phe Lys Asp Glu Gly Glu Gln Glu Lys Ser Ser
            20                  25                  30

Glu Asn Ser Ser Ala Glu Arg Asp Leu Ala Asp Val Lys Ser Ser Leu
            35                  40                  45

Val Asn Glu Ser Glu Thr Asn Gln Asn Ser Ser Ser Asp Ser Glu Ala
50                  55                  60

Glu Arg Arg Pro Pro Arg Ser Glu Ser Phe Arg Asp Lys Ser Arg
65                  70                  75                  80

Glu Ser Leu Glu Glu Ala Ala Lys Arg Gln Asp Gly Gly Leu Phe Lys
                85                  90                  95

Gly Pro Pro Tyr Pro Gly Tyr Pro Phe Ile Met Ile Pro Asp Leu Thr
                100                 105                 110

Ser Pro Tyr Leu Pro Asn Gly Ser Leu Ser Pro Thr Ala Arg Thr Leu
                115                 120                 125

His Phe Gln Ser Gly Ser Thr His Tyr Ser Ala Tyr Lys Thr Ile Glu
            130                 135                 140

His Gln Ile Ala Val Gln Tyr Leu Gln Met Lys Trp Pro Leu Leu Asp
145                 150                 155                 160

Val Gln Ala Gly Ser Leu Gln Ser Arg Gln Ala Leu Lys Asp Ala Arg
                165                 170                 175

Ser Pro Ser Pro Ala His Ile Val Ser Asn Lys Val Pro Val Val Gln
                180                 185                 190

His Pro His His Val His Pro Leu Thr Pro Leu Ile Thr Tyr Ser Asn
            195                 200                 205

Glu His Phe Thr Pro Gly Asn Pro Pro Pro His Leu Pro Ala Asp Val
```

```
                210                 215                 220
Asp Pro Lys Thr Gly Ile Pro Arg Pro Pro His Pro Asp Ile Ser
225                 230                 235                 240

Pro Tyr Tyr Pro Leu Ser Pro Gly Thr Val Gly Gln Ile Pro His Pro
                245                 250                 255

Leu Gly Trp Leu Val Pro Gln Gln Gly Gln Pro Val Tyr Pro Ile Thr
                260                 265                 270

Thr Gly Gly Phe Arg His Pro Tyr Pro Thr Ala Leu Thr Val Asn Ala
                275                 280                 285

Ser Met Ser Arg Phe Pro Pro His Met Val Pro Pro His His Thr Leu
                290                 295                 300

His Thr Thr Gly Ile Pro His Pro Ala Ile Val Thr Pro Thr Val Lys
305                 310                 315                 320

Gln Glu Ser Ser Gln Ser Asp Val Gly Ser Leu His Ser Ser Lys His
                325                 330                 335

Gln Asp Ser Lys Lys Glu Glu Lys Lys Pro His Ile Lys Lys
                340                 345                 350

Pro Leu Asn Ala Phe Met Leu Tyr Met Lys Glu Met Arg Ala Lys Val
                355                 360                 365

Val Ala Glu Cys Thr Leu Lys Glu Ser Ala Ala Ile Asn Gln Ile Leu
370                 375                 380

Gly Arg Arg Trp His Ala Leu Ser Arg Glu Glu Gln Ala Lys Tyr Tyr
385                 390                 395                 400

Glu Leu Ala Arg Lys Glu Arg Gln Leu His Met Gln Leu Tyr Pro Gly
                405                 410                 415

Trp Ser Ala Arg Asp Asn Tyr Gly Lys Lys Lys Arg Lys Arg Asp
                420                 425                 430

Lys Gln Pro Gly Glu Thr Asn Asp Ala Asn Thr Pro Lys Lys Cys Arg
                435                 440                 445

Ala Leu Phe Gly Leu Asp Arg Gln Thr Leu Trp Cys Lys Pro Cys Arg
450                 455                 460

Arg Lys Lys Lys Cys Val Arg Tyr Ile Gln Gly Glu Gly Ser Cys Leu
465                 470                 475                 480

Ser Pro Pro Ser Ser Asp Gly Ser Leu Leu Asp Ser Pro Pro Ser
                485                 490                 495

Pro Asn Leu Leu Gly Ser Pro Pro Arg Asp Ala Lys Ser Gln Thr Glu
                500                 505                 510

Gln Thr Gln Pro Leu Ser Leu Ser Leu Lys Pro Asp Pro Leu Ala His
                515                 520                 525

Leu Ser Met Met Pro Pro Pro Ala Leu Leu Leu Ala Glu Ala Thr
530                 535                 540

His Lys Ala Ser Ala Leu Cys Pro Asn Gly Ala Leu Asp Leu Pro Pro
545                 550                 555                 560

Ala Ala Leu Gln Pro Ala Ala Pro Ser Ser Ser Ile Ala Gln Pro Ser
                565                 570                 575

Thr Ser Ser Leu His Ser His Ser Ser Leu Ala Gly Thr Gln Pro Gln
                580                 585                 590

Pro Leu Ser Leu Val Thr Lys Ser Leu Glu
                595                 600

<210> SEQ ID NO 71
<211> LENGTH: 2161
<212> TYPE: DNA
<213> ORGANISM: Homo sapiens
```

-continued

```
<220> FEATURE:
<221> NAME/KEY: CDS
<222> LOCATION: (152)..(1489)

<400> SEQUENCE: 71
gcgacggtta acggggccc aaggcagggg tggcgggtca gtgctgctcg ggggcttctc      60
catccaggtc cctggagttc ctggtccctg gagctccgca cttggcggcg caacctgcgt    120
gaggcagcgc gactctggcg actggccggc c atg cct tcc cgg gct gag gac       172
                                   Met Pro Ser Arg Ala Glu Asp
                                     1               5 tat gaa gtg ttg tac acc att ggc aca ggc tcc tac ggc cgc tgc cag      220
Tyr Glu Val Leu Tyr Thr Ile Gly Thr Gly Ser Tyr Gly Arg Cys Gln
         10                  15                  20 aag atc cgg agg aag agt gat ggc aag ata tta gtt tgg aaa gaa ctt      268
Lys Ile Arg Arg Lys Ser Asp Gly Lys Ile Leu Val Trp Lys Glu Leu
 25                  30                  35 gac tat ggc tcc atg aca gaa gct gag aaa cag atg ctt gtt tct gaa      316
Asp Tyr Gly Ser Met Thr Glu Ala Glu Lys Gln Met Leu Val Ser Glu
 40                  45                  50                  55 gtg aat ttg ctt cgt gaa ctg aaa cat cca aac atc gtt cgt tac tat      364
Val Asn Leu Leu Arg Glu Leu Lys His Pro Asn Ile Val Arg Tyr Tyr
                 60                  65                  70 gat cgg att att gac cgg acc aat aca aca ctg tac att gta atg gaa      412
Asp Arg Ile Ile Asp Arg Thr Asn Thr Thr Leu Tyr Ile Val Met Glu
         75                  80                  85 tat tgt gaa gga ggg gat ctg gct agt gta att aca aag gga acc aag      460
Tyr Cys Glu Gly Gly Asp Leu Ala Ser Val Ile Thr Lys Gly Thr Lys
     90                  95                 100 gaa agg caa tac tta gat gaa gag ttt gtt ctt cga gtg atg act cag      508
Glu Arg Gln Tyr Leu Asp Glu Glu Phe Val Leu Arg Val Met Thr Gln
105                 110                 115 ttg act ctg gcc ctg aag gaa tgc cac aga cga agt gat ggt ggt cat      556
Leu Thr Leu Ala Leu Lys Glu Cys His Arg Arg Ser Asp Gly Gly His
120                 125                 130                 135 acc gta ttg cat cgg gat ctg aaa cca gcc aat gtt ttc ctg gat ggc      604
Thr Val Leu His Arg Asp Leu Lys Pro Ala Asn Val Phe Leu Asp Gly
                140                 145                 150 aag caa aac gtc aag ctt gga gac ttt ggg cta gct aga ata tta aac      652
Lys Gln Asn Val Lys Leu Gly Asp Phe Gly Leu Ala Arg Ile Leu Asn
        155                 160                 165 cat gac acg agt ttt gca aaa aca ttt gtt ggc aca cct tat tac atg      700
His Asp Thr Ser Phe Ala Lys Thr Phe Val Gly Thr Pro Tyr Tyr Met
    170                 175                 180 tct cct gaa caa atg aat cgc atg tcc tac aat gag aaa tca gat atc      748
Ser Pro Glu Gln Met Asn Arg Met Ser Tyr Asn Glu Lys Ser Asp Ile
185                 190                 195 tgg tca ttg ggc tgc ttg ctg tat gag tta tgt gca tta atg cct cca      796
Trp Ser Leu Gly Cys Leu Leu Tyr Glu Leu Cys Ala Leu Met Pro Pro
200                 205                 210                 215 ttt aca gct ttt agc cag aaa gaa ctc gct ggg aaa atc aga gaa ggc      844
Phe Thr Ala Phe Ser Gln Lys Glu Leu Ala Gly Lys Ile Arg Glu Gly
                220                 225                 230 aaa ttc agg cga att cca tac cgt tac tct gat gaa ttg aat gaa att      892
Lys Phe Arg Arg Ile Pro Tyr Arg Tyr Ser Asp Glu Leu Asn Glu Ile
        235                 240                 245 att acg agg atg tta aac tta aag gat tac cat cga cct tct gtt gaa      940
Ile Thr Arg Met Leu Asn Leu Lys Asp Tyr His Arg Pro Ser Val Glu
    250                 255                 260 gaa att ctt gag aac cct tta ata gca gat ttg gtt gca gac gag caa      988
Glu Ile Leu Glu Asn Pro Leu Ile Ala Asp Leu Val Ala Asp Glu Gln
```

```
               Glu Ile Leu Glu Asn Pro Leu Ile Ala Asp Leu Val Ala Asp Glu Gln
                   265                 270                 275 aga aga aat ctt gag aga aga ggg cga caa tta gga gag cca gaa aaa       1036
Arg Arg Asn Leu Glu Arg Arg Gly Arg Gln Leu Gly Glu Pro Glu Lys
280                 285                 290                 295 tcg cag gat tcc agc cct gta ttg agt gag ctg aaa ctg aag gaa att       1084
Ser Gln Asp Ser Ser Pro Val Leu Ser Glu Leu Lys Leu Lys Glu Ile
                    300                 305                 310 cag tta cag gag cga gag cga gct ctc aaa gca aga gaa gaa aga ttg       1132
Gln Leu Gln Glu Arg Glu Arg Ala Leu Lys Ala Arg Glu Glu Arg Leu
                315                 320                 325 gag cag aaa gaa cag gag ctt tgt gtt cgt gag aga cta gca gag gac       1180
Glu Gln Lys Glu Gln Glu Leu Cys Val Arg Glu Arg Leu Ala Glu Asp
            330                 335                 340 aaa ctg gct aga gca gaa aat ctg ttg aag aac tac agc ttg cta aag       1228
Lys Leu Ala Arg Ala Glu Asn Leu Leu Lys Asn Tyr Ser Leu Leu Lys
345                 350                 355 gaa cgg aag ttc ctg tct ctg gca agt aat cca gaa ctt ctt aat ctt       1276
Glu Arg Lys Phe Leu Ser Leu Ala Ser Asn Pro Glu Leu Leu Asn Leu
360                 365                 370                 375 cca tcc tca gta att aag aag aaa gtt cat ttc agt ggg gaa agt aaa       1324
Pro Ser Ser Val Ile Lys Lys Lys Val His Phe Ser Gly Glu Ser Lys
                    380                 385                 390 gag aac atc atg agg agt gag aat tct gag agt cag ctc aca tct aag       1372
Glu Asn Ile Met Arg Ser Glu Asn Ser Glu Ser Gln Leu Thr Ser Lys
                395                 400                 405 tcc aag tgc aag gac ctg aag aaa agg ctt cac gct gcc cag ctg cgg       1420
Ser Lys Cys Lys Asp Leu Lys Lys Arg Leu His Ala Ala Gln Leu Arg
            410                 415                 420 gct caa gcc ctg tca gat att gag aaa aat tac caa ctg aaa agc aga       1468
Ala Gln Ala Leu Ser Asp Ile Glu Lys Asn Tyr Gln Leu Lys Ser Arg
        425                 430                 435 cag atc ctg ggc atg cgc tag ccaggtagag agacacagag ctgtgtacag          1519
Gln Ile Leu Gly Met Arg
440                 445 gatgtaatat taccaacctt taaagactga tattcaaatg ctgtagtgtt gaatacttgg     1579
ttccatgagc catgcctttc tgtatagtac acatgatatt tcggaattgg ttttactgtt    1639
cttcagcaac tattgtacaa aatgttcaca tttaattttt ctttcttctt ttaagaacat    1699
attataaaaa gaatactttc ttggttgggc ttttaatcct gtgtgtgatt actagtagga    1759
acatgagatg tgacattcta aatcttggga gaaaaataa tgttaggaaa aaatattta      1819 tgcaggaaga gtagcactca ctgaatagtt ttaaatgact gagtggtatg cttacaattg    1879
tcatgtctag atttaaattt taagtctgag attttaaatg ttttgagct tagaaaaccc     1939 agttagatgc aatttggtca ttaataccat gacatcttgc ttataaatat tccattgctc    1999
tgtagttcaa atctgttagc tttgtgaaaa ttcatcactg tgatgtttgt attctttttt    2059
tttttctgtt taacagaata tgagctgtct gtcatttacc tacttctttc ccactaaata    2119
aaagaattct tcagtttccc tgtaaaaaaa aaaaaaaaa aa                        2161

<210> SEQ ID NO 72
<211> LENGTH: 445
<212> TYPE: PRT
<213> ORGANISM: Homo sapiens

<400> SEQUENCE: 72

Met Pro Ser Arg Ala Glu Asp Tyr Glu Val Leu Tyr Thr Ile Gly Thr
1               5                   10                  15
```

```
Gly Ser Tyr Gly Arg Cys Gln Lys Ile Arg Arg Lys Ser Asp Gly Lys
            20                  25                  30

Ile Leu Val Trp Lys Glu Leu Asp Tyr Gly Ser Met Thr Glu Ala Glu
        35                  40                  45

Lys Gln Met Leu Val Ser Glu Val Asn Leu Leu Arg Glu Leu Lys His
    50                  55                  60

Pro Asn Ile Val Arg Tyr Tyr Asp Arg Ile Ile Asp Arg Thr Asn Thr
65                  70                  75                  80

Thr Leu Tyr Ile Val Met Glu Tyr Cys Glu Gly Gly Asp Leu Ala Ser
                85                  90                  95

Val Ile Thr Lys Gly Thr Lys Glu Arg Gln Tyr Leu Asp Glu Glu Phe
            100                 105                 110

Val Leu Arg Val Met Thr Gln Leu Thr Leu Ala Leu Lys Glu Cys His
        115                 120                 125

Arg Arg Ser Asp Gly Gly His Thr Val Leu His Arg Asp Leu Lys Pro
    130                 135                 140

Ala Asn Val Phe Leu Asp Gly Lys Gln Asn Val Lys Leu Gly Asp Phe
145                 150                 155                 160

Gly Leu Ala Arg Ile Leu Asn His Asp Thr Ser Phe Ala Lys Thr Phe
                165                 170                 175

Val Gly Thr Pro Tyr Tyr Met Ser Pro Glu Gln Met Asn Arg Met Ser
            180                 185                 190

Tyr Asn Glu Lys Ser Asp Ile Trp Ser Leu Gly Cys Leu Leu Tyr Glu
        195                 200                 205

Leu Cys Ala Leu Met Pro Pro Phe Thr Ala Phe Ser Gln Lys Glu Leu
    210                 215                 220

Ala Gly Lys Ile Arg Glu Gly Lys Phe Arg Arg Ile Pro Tyr Arg Tyr
225                 230                 235                 240

Ser Asp Glu Leu Asn Glu Ile Ile Thr Arg Met Leu Asn Leu Lys Asp
                245                 250                 255

Tyr His Arg Pro Ser Val Glu Glu Ile Leu Glu Asn Pro Leu Ile Ala
            260                 265                 270

Asp Leu Val Ala Asp Glu Gln Arg Arg Asn Leu Glu Arg Arg Gly Arg
        275                 280                 285

Gln Leu Gly Glu Pro Glu Lys Ser Gln Asp Ser Ser Pro Val Leu Ser
    290                 295                 300

Glu Leu Lys Leu Lys Glu Ile Gln Leu Gln Glu Arg Glu Arg Ala Leu
305                 310                 315                 320

Lys Ala Arg Glu Glu Arg Leu Glu Gln Lys Glu Gln Glu Leu Cys Val
                325                 330                 335

Arg Glu Arg Leu Ala Glu Asp Lys Leu Ala Arg Ala Glu Asn Leu Leu
            340                 345                 350

Lys Asn Tyr Ser Leu Leu Lys Glu Arg Lys Phe Leu Ser Leu Ala Ser
        355                 360                 365

Asn Pro Glu Leu Leu Asn Leu Pro Ser Ser Val Ile Lys Lys Lys Val
    370                 375                 380

His Phe Ser Gly Glu Ser Lys Glu Asn Ile Met Arg Ser Glu Asn Ser
385                 390                 395                 400

Glu Ser Gln Leu Thr Ser Lys Ser Lys Cys Lys Asp Leu Lys Lys Arg
                405                 410                 415

Leu His Ala Ala Gln Leu Arg Ala Gln Ala Leu Ser Asp Ile Glu Lys
            420                 425                 430
```

```
Asn Tyr Gln Leu Lys Ser Arg Gln Ile Leu Gly Met Arg
        435                 440                 445

<210> SEQ ID NO 73
<211> LENGTH: 2655
<212> TYPE: DNA
<213> ORGANISM: Homo sapiens
<220> FEATURE:
<221> NAME/KEY: CDS
<222> LOCATION: (122)..(550)

<400> SEQUENCE: 73
cccagaaggc cgcgggggt ggaccgccta agagggcgtg cgctcccgac atgccccgcg        60
gcgcgccatt aaccgccaga tttgaatcgc gggacccgtt ggcagaggtg gcggcggcgg      120 c atg ggt gcc ccg acg ttg ccc cct gcc tgg cag ccc ttt ctc aag gac      169
  Met Gly Ala Pro Thr Leu Pro Pro Ala Trp Gln Pro Phe Leu Lys Asp
  1               5                  10                  15 cac cgc atc tct aca ttc aag aac tgg ccc ttc ttg gag ggc tgc gcc        217
His Arg Ile Ser Thr Phe Lys Asn Trp Pro Phe Leu Glu Gly Cys Ala
            20                  25                  30 tgc acc ccg gag cgg atg gcc gag gct ggc ttc atc cac tgc ccc act        265
Cys Thr Pro Glu Arg Met Ala Glu Ala Gly Phe Ile His Cys Pro Thr
        35                  40                  45 gag aac gag cca gac ttg gcc cag tgt ttc ttc tgc ttc aag gag ctg        313
Glu Asn Glu Pro Asp Leu Ala Gln Cys Phe Phe Cys Phe Lys Glu Leu
    50                  55                  60 gaa ggc tgg gag cca gat gac gac ccc ata gag gaa cat aaa aag cat        361
Glu Gly Trp Glu Pro Asp Asp Asp Pro Ile Glu Glu His Lys Lys His
65                  70                  75                  80 tcg tcc ggt tgc gct ttc ctt tct gtc aag aag cag ttt gaa gaa tta        409
Ser Ser Gly Cys Ala Phe Leu Ser Val Lys Lys Gln Phe Glu Glu Leu
                85                  90                  95 acc ctt ggt gaa ttt ttg aaa ctg gac aga gaa aga gcc aag aac aaa        457
Thr Leu Gly Glu Phe Leu Lys Leu Asp Arg Glu Arg Ala Lys Asn Lys
            100                 105                 110 att gca aag gaa acc aac aat aag aag aaa gaa ttt gag gaa act gcg        505
Ile Ala Lys Glu Thr Asn Asn Lys Lys Lys Glu Phe Glu Glu Thr Ala
        115                 120                 125 gag aaa gtg cgc cgt gcc atc gag cag ctg gct gcc atg gat tga            550
Glu Lys Val Arg Arg Ala Ile Glu Gln Leu Ala Ala Met Asp
    130                 135                 140 ggcctctggc cggagctgcc tggtcccaga gtggctgcac cacttccagg gtttattccc       610
tggtgccacc agccttcctg tgggcccctt agcaatgtct taggaaagga gatcaacatt       670
ttcaaattag atgtttcaac tgtgctcttg ttttgtcttg aaagtggcac cagaggtgct       730
tctgcctgtg cagcgggtgc tgctggtaac agtggctgct tctctctctc tctctctttt       790
ttgggggctc attttgctg ttttgattcc cgggcttacc aggtgagaag tgagggagga       850
agaaggcagt gtcccttttg ctagagctga cagctttgtt cgcgtgggca gagccttcca       910
cagtgaatgt gtctggacct catgttgttg aggctgtcac agtcctgagt gtggacttgg       970
caggtgcctg ttgaatctga gctgcaggtt ccttatctgt cacacctgtg cctcctcaga      1030
ggacagtttt tttgttgttg tgttttttg tttttttttt tttggtagat gcatgacttg      1090
tgtgtgatga gagaatggag acagagtccc tggctcctct actgtttaac aacatggctt      1150
tcttattttg tttgaattgt taattcacag aatagcacaa actacaatta aaactaagca      1210
caaagccatt ctaagtcatt ggggaaacgg ggtgaacttc aggtggatga ggagacagaa      1270
tagagtgata ggaagcgtct ggcagatact ccttttgcca ctgctgtgtg attagacagg      1330
```

```
cccagtgagc cgcggggcac atgctggccg ctcctccctc agaaaaaggc agtggcctaa    1390
atccttttta aatgacttgg ctcgatgctg tggggactg gctgggctgc tgcaggccgt     1450
gtgtctgtca gcccaacctt cacatctgtc acgttctcca cacggggag agacgcagtc     1510
cgcccaggtc cccgctttct ttggaggcag cagctcccgc agggctgaag tctggcgtaa    1570
gatgatggat ttgattcgcc ctcctccctg tcatagagct gcagggtgga ttgttacagc    1630
ttcgctggaa acctctggag gtcatctcgg ctgttcctga gaataaaaaa gcctgtcatt    1690
tcaaacactg ctgtggaccc tactgggttt ttaaaatatt gtcagttttt catcgtcgtc    1750
cctagcctgc caacagccat ctgcccagac agccgcagtg aggatgagcg tcctggcaga    1810
gacgcagttg tctctgggcg cttgccagag ccacgaaccc cagacctgtt tgtatcatcc    1870
gggctccttc cgggcagaaa caactgaaaa tgcacttcag acccacttat ttctgccaca    1930
tctgagtcgg cctgagatag acttttccct ctaaactggg agaatatcac agtggttttt    1990
gttagcagaa aatgcactcc agcctctgta ctcatctaag ctgcttattt ttgatatttg    2050
tgtcagtctg taaatggata cttcacttta ataactgttg cttagtaatt ggctttgtag    2110
agaagctgga aaaaaatggt tttgtcttca actcctttgc atgccaggcg gtgatgtgga    2170
tctcggcttc tgtgagcctg tgctgtgggc agggctgagc tggagccgcc cctctcagcc    2230
cgcctgccac ggcctttcct taaaggccat ccttaaaacc agaccctcat ggctaccagc    2290
acctgaaagc ttcctcgaca tctgttaata aagccgtagg ccccttgtcta agtgcaaccg   2350
cctagacttt ctttcagata catgtccaca tgtccatttt tcaggttctc taagttggag    2410
tggagtctgg gaagggttgt gaatgaggct tctgggctat gggtgaggtt ccaatggcag    2470
gttagagccc ctcgggccaa ctgccatcct ggaaagtaga gacagcagtg cccgctgccc    2530
agaagagacc agcaagccaa actggagccc ccattgcagg ctgtcgccat gtggaaagag    2590
taactcacaa ttgccaataa agtctcatgt ggtttttatct aaaaaaaaaa aaaaaaaaa    2650
aaaaa                                                                2655
```

<210> SEQ ID NO 74
<211> LENGTH: 142
<212> TYPE: PRT
<213> ORGANISM: Homo sapiens

<400> SEQUENCE: 74

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Asp Pro Ile Glu His Lys Lys His
65                  70                  75                  80

Ser Ser Gly Cys Ala Phe Leu Ser Val Lys Lys Gln Phe Glu Glu Leu
                85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Lys Glu Phe Glu Glu Thr Ala
        115                 120                 125

```
      Glu Lys Val Arg Arg Ala Ile Glu Gln Leu Ala Ala Met Asp
          130                 135                 140

<210> SEQ ID NO 75
<211> LENGTH: 4107
<212> TYPE: DNA
<213> ORGANISM: Homo sapiens
<220> FEATURE:
<221> NAME/KEY: CDS
<222> LOCATION: (209)..(1261)

<400> SEQUENCE: 75
gcgcaaccct ccggaagctg ccgccccttt cccttttat gggaatactt ttttaaaaa      60 aaaagagttc gctggcgcca ccccgtagga ctggccgccc taaaaccgtg ataaaggagc    120
tgctcgccac ttctcacttc cgcttccttc cagtaaggag tcggggtctt ccccagtttt    180
ctcagccagg cggcggcggc gactggca atg ttt ggc ctc aaa aga aac gcg       232
                                 Met Phe Gly Leu Lys Arg Asn Ala
                                   1               5 gta atc gga ctc aac ctc tac tgt ggg ggg gcc ggc ttg ggg gcc ggc      280
Val Ile Gly Leu Asn Leu Tyr Cys Gly Gly Ala Gly Leu Gly Ala Gly
    10                  15                  20 agc ggc ggc gcc acc cgc ccg gga ggg cga ctt ttg gct acg gag aag      328
Ser Gly Gly Ala Thr Arg Pro Gly Gly Arg Leu Leu Ala Thr Glu Lys
 25                  30                  35                  40 gag gcc tcg gcc cgg cga gag ata ggg gga ggg gag gcc ggc gcg gtg      376
Glu Ala Ser Ala Arg Arg Glu Ile Gly Gly Gly Glu Ala Gly Ala Val
                 45                  50                  55 att ggc gga agc gcc ggc gca agc ccc ccg tcc acc ctc acg cca gac      424
Ile Gly Gly Ser Ala Gly Ala Ser Pro Pro Ser Thr Leu Thr Pro Asp
             60                  65                  70 tcc cgg agg gtc gcg cgg ccg ccg ccc att ggc gcc gag gtc ccc gac      472
Ser Arg Arg Val Ala Arg Pro Pro Pro Ile Gly Ala Glu Val Pro Asp
         75                  80                  85 gtc acc gcg acc ccc gcg agg ctg ctt ttc ttc gcg ccc acc cgc cgc      520
Val Thr Ala Thr Pro Ala Arg Leu Leu Phe Phe Ala Pro Thr Arg Arg
     90                  95                 100 gcg gcg ccg ctt gag gag atg gaa gcc ccg gcc gct gac gcc atc atg      568
Ala Ala Pro Leu Glu Glu Met Glu Ala Pro Ala Ala Asp Ala Ile Met
105                 110                 115                 120 tcg ccc gaa gag gag ctg gac ggg tac gag ccg gag cct ctc ggg aag      616
Ser Pro Glu Glu Glu Leu Asp Gly Tyr Glu Pro Glu Pro Leu Gly Lys
                125                 130                 135 cgg ccg gct gtc ctg ccg ctg ctg gag ttg gtc ggg gaa tct ggt aat      664
Arg Pro Ala Val Leu Pro Leu Leu Glu Leu Val Gly Glu Ser Gly Asn
            140                 145                 150 aac acc agt acg gac ggg tca cta ccc tcg acg ccg ccg cca gca gag      712
Asn Thr Ser Thr Asp Gly Ser Leu Pro Ser Thr Pro Pro Pro Ala Glu
        155                 160                 165 gag gag gag gac gag ttg tac cgg cag tcg ctg gag att atc tct cgg      760
Glu Glu Glu Asp Glu Leu Tyr Arg Gln Ser Leu Glu Ile Ile Ser Arg
    170                 175                 180 tac ctt cgg gag cag gcc acc ggc gcc aag gac aca aag cca atg ggc      808
Tyr Leu Arg Glu Gln Ala Thr Gly Ala Lys Asp Thr Lys Pro Met Gly
185                 190                 195                 200 agg tct ggg gcc acc agc agg aag gcg ctg gag acc tta cga cgg gtt      856
Arg Ser Gly Ala Thr Ser Arg Lys Ala Leu Glu Thr Leu Arg Arg Val
                205                 210                 215 ggg gat ggc gtg cag cgc aac cac gag acg gcc ttc caa ggc atg ctt      904
Gly Asp Gly Val Gln Arg Asn His Glu Thr Ala Phe Gln Gly Met Leu
            220                 225                 230
```

| | | |
|---|---|---|
| cgg aaa ctg gac atc aaa aac gaa gac gat gtg aaa tcg ttg tct cga<br>Arg Lys Leu Asp Ile Lys Asn Glu Asp Asp Val Lys Ser Leu Ser Arg<br>235 240 245 | | 952 |
| gtg atg atc cat gtt ttc agc gac ggc gta aca aac tgg ggc agg att<br>Val Met Ile His Val Phe Ser Asp Gly Val Thr Asn Trp Gly Arg Ile<br>250 255 260 | | 1000 |
| gtg act ctc att tct ttt ggt gcc ttt gtg gct aaa cac ttg aag acc<br>Val Thr Leu Ile Ser Phe Gly Ala Phe Val Ala Lys His Leu Lys Thr<br>265 270 275 280 | | 1048 |
| ata aac caa gaa agc tgc atc gaa cca tta gca gaa agt atc aca gac<br>Ile Asn Gln Glu Ser Cys Ile Glu Pro Leu Ala Glu Ser Ile Thr Asp<br>285 290 295 | | 1096 |
| gtt ctc gta agg aca aaa cgg gac tgg cta gtt aaa caa aga ggc tgg<br>Val Leu Val Arg Thr Lys Arg Asp Trp Leu Val Lys Gln Arg Gly Trp<br>300 305 310 | | 1144 |
| gat ggg ttt gtg gag ttc ttc cat gta gag gac cta gaa ggt ggc atc<br>Asp Gly Phe Val Glu Phe Phe His Val Glu Asp Leu Glu Gly Gly Ile<br>315 320 325 | | 1192 |
| agg aat gtg ctg ctg gct ttt gca ggt gtt gct gga gta gga gct ggt<br>Arg Asn Val Leu Leu Ala Phe Ala Gly Val Ala Gly Val Gly Ala Gly<br>330 335 340 | | 1240 |
| ttg gca tat cta ata aga tag ccttactgta agtgcaatag ttgactttta<br>Leu Ala Tyr Leu Ile Arg<br>345 350 | | 1291 |
| accaaccacc accaccacca aaaccagttt atgcagttgg actccaagct gtaacttcct | | 1351 |
| agagttgcac cctagcaacc tagccagaaa agcaagtggc aagaggatta tggctaacaa | | 1411 |
| gaataaatac atgggaagag tgctccccat tgattgaaga gtcactgtct gaaagaagca | | 1471 |
| aagttcagtt tcagcaacaa acaaactttg tttgggaagc tatggaggag gacttttaga | | 1531 |
| tttagtgaag atggtagggt ggaaagactt aatttccttg ttgagaacag gaaagtggcc | | 1591 |
| agtagccagg caagtcatag aattgattac ccgccgaatt cattaattta ctgtagtgtt | | 1651 |
| aagagaagca ctaagaatgc cagtgacctg tgtaaaagtt acaagtaata gaactatgac | | 1711 |
| tgtaagcctc agtactgtac aagggaagct tttcctctct ctaattagct ttcccagtat | | 1771 |
| acttcttaga aagtccaagt gttcaggact tttatacctg ttatactttg gcttggtttc | | 1831 |
| catgattctt actttattag cctagtttat caccaataat acttgacgga aggctcagta | | 1891 |
| attagttatg aaatatggata tcctcaattc ttaagacagc ttgtaaatgt atttgtaaaa | | 1951 |
| attgtatata tttttacaga aagtctattt ctttgaaacg aaggaagtat cgaatttaca | | 2011 |
| ttagtttttt tcatacccctt ttgaactttg caacttccgt aattaggaac ctgtttctta | | 2071 |
| cagcttttct atgctaaact ttgttctgtt cagttctaga gtgtatacag aacgaattga | | 2131 |
| tgtgtaactg tatgcagact ggttgtagtg gaacaaatct gataactatg caggtttaaa | | 2191 |
| ttttcttatc tgattttggt aagtattcct tagataggtt tttctttgaa aacctgggat | | 2251 |
| tgagaggttg atgaatggaa attctttcac ttcattatat gcaagttttc ataattagg | | 2311 |
| tctaagtgga gttttaaggt tactgatgac ttacaaataa tgggctctga ttgggcaata | | 2371 |
| ctcatttgag ttccttccat ttgacctaat ttaactggtg aaatttaaag tgaattcatg | | 2431 |
| ggctcatctt taaagctttt actaaaagat tttcagctga atggaactca ttagctgtgt | | 2491 |
| gcatataaaa agatcacatc aggtggatgg agagacattt gatcccttgt ttgcttaata | | 2551 |
| aattataaaa tgatggcttg gaaaagcagg ctagtctaac catggtgcta ttattaggct | | 2611 |
| tgcttgttac acacacaggt ctaagcctag tatgtcaata aagcaaatac ttactgtttt | | 2671 |

```
gtttctatta atgattccca aaccttgttg caagttttttg cattggcatc tttggatttc    2731
agtcttgatg tttgttctat cagacttaac ctttttattc ctgtccttcc ttgaaattgc    2791
tgattgttct gctccctcta cagatattta tatcaattcc tacagctttc ccctgccatc    2851
cctgaactct ttctagccct tttagatttt ggcactgtga aaccctgct ggaaacctga     2911
gtgaccctcc ctccccacca agagtccaca gacctttcat ctttcacgaa cttgatcctg    2971
ttagcaggtg gtaataccat gggtgctgtg acactaacag tcattgagag gtgggaggaa    3031
gtccctttc cttggactgg tatcttttca actattgttt tatcctgtct ttgggggcaa    3091
tgtgtcaaaa gtcccctcag gaattttcag aggaaagaac attttatgag ctttctcta    3151
aagtttcctt tgtataggag tatgctcact taaatttaca gaaagaggtg agctgtgtta    3211
aacctcagag tttaaaagct actgataaac tgaagaaagt gtctatattg gaactagggt    3271
catttgaaag cttcagtctc ggaacatgac ctttagtctg tggactccat ttaaaaatag    3331
gtatgaataa gatgactaag aatgtaatgg ggaagaactg ccctgcctgc ccatctcaga    3391
gccataaggt catctttgct agagctattt ttacctatgt atttatcgtt cttgatcata    3451
agccgcttat ttatatcatg tatctctaag gacctaaaag cactttatgt agtttttaat    3511
taatcttaag atctggttac ggtaactaaa aaagcctgtc tgccaaatcc agtggaaaca    3571
agtgcataga tgtgaattgg ttttaggggg ccccacttcc caattcatta ggtatgactg    3631
tggaaataca gacaaggatc ttagttgata ttttgggctt ggggcagtga gggcttagga    3691
caccccaagt ggtttgggaa aggaggaggg gagtggtggg tttataggg gaggaggagg    3751
caggtggtct aagtgctgac tggctacgta gttcgggcaa atcctccaaa agggaaaggg    3811
aggatttgct tagaaggatg gcgctcccag tgactacttt ttgacttctg tttgtcttac    3871
gcttctctca gggaaaaaca tgcagtcctc tagtgtttca tgtacattct gtgggggtg    3931
aacaccttgg ttctggttaa acagctgtac ttttgatagc tgtgccagga agggttagga    3991
ccaactacaa attaatgttg gttgtcaaat gtagtgtgtt tccctaactt tctgtttttc    4051
ctgagaaaaa aaaataaatc ttttattcaa atacagggaa aaaaaaaaaa aaaaaa       4107
```

<210> SEQ ID NO 76
<211> LENGTH: 350
<212> TYPE: PRT
<213> ORGANISM: Homo sapiens

<400> SEQUENCE: 76

Met Phe Gly Leu Lys Arg Asn Ala Val Ile Gly Leu Asn Leu Tyr Cys
1               5                   10                  15

Gly Gly Ala Gly Leu Gly Ala Gly Ser Gly Gly Ala Thr Arg Pro Gly
                20                  25                  30

Gly Arg Leu Leu Ala Thr Glu Lys Glu Ala Ser Ala Arg Arg Glu Ile
            35                  40                  45

Gly Gly Gly Glu Ala Gly Ala Val Ile Gly Gly Ser Ala Gly Ala Ser
        50                  55                  60

Pro Pro Ser Thr Leu Thr Pro Asp Ser Arg Arg Val Ala Arg Pro Pro
65                  70                  75                  80

Pro Ile Gly Ala Glu Val Pro Asp Val Thr Ala Thr Pro Ala Arg Leu
                85                  90                  95

Leu Phe Phe Ala Pro Thr Arg Arg Ala Ala Pro Leu Glu Glu Met Glu
            100                 105                 110

Ala Pro Ala Ala Asp Ala Ile Met Ser Pro Glu Glu Leu Asp Gly
        115                 120                 125

-continued

```
Tyr Glu Pro Glu Pro Leu Gly Lys Arg Pro Ala Val Leu Pro Leu Leu
    130                 135                 140

Glu Leu Val Gly Glu Ser Gly Asn Asn Thr Ser Thr Asp Gly Ser Leu
145                 150                 155                 160

Pro Ser Thr Pro Pro Ala Glu Glu Glu Asp Glu Leu Tyr Arg
                165                 170                 175

Gln Ser Leu Glu Ile Ile Ser Arg Tyr Leu Arg Glu Gln Ala Thr Gly
                180                 185                 190

Ala Lys Asp Thr Lys Pro Met Gly Arg Ser Gly Ala Thr Ser Arg Lys
            195                 200                 205

Ala Leu Glu Thr Leu Arg Arg Val Gly Asp Gly Val Gln Arg Asn His
        210                 215                 220

Glu Thr Ala Phe Gln Gly Met Leu Arg Lys Leu Asp Ile Lys Asn Glu
225                 230                 235                 240

Asp Asp Val Lys Ser Leu Ser Arg Val Met Ile His Val Phe Ser Asp
                245                 250                 255

Gly Val Thr Asn Trp Gly Arg Ile Val Thr Leu Ile Ser Phe Gly Ala
            260                 265                 270

Phe Val Ala Lys His Leu Lys Thr Ile Asn Gln Glu Ser Cys Ile Glu
        275                 280                 285

Pro Leu Ala Glu Ser Ile Thr Asp Val Leu Val Arg Thr Lys Arg Asp
    290                 295                 300

Trp Leu Val Lys Gln Arg Gly Trp Asp Gly Phe Val Glu Phe Phe His
305                 310                 315                 320

Val Glu Asp Leu Glu Gly Gly Ile Arg Asn Val Leu Leu Ala Phe Ala
                325                 330                 335

Gly Val Ala Gly Val Gly Ala Gly Leu Ala Tyr Leu Ile Arg
            340                 345                 350

<210> SEQ ID NO 77
<211> LENGTH: 2204
<212> TYPE: DNA
<213> ORGANISM: Homo sapiens
<220> FEATURE:
<221> NAME/KEY: CDS
<222> LOCATION: (54)..(1865)

<400> SEQUENCE: 77
gagcggtgcg gaggctctgc tcggatcgag gtctgcagcg cagcttcggg agc atg        56
                                                         Met
                                                         1 agt gct gca gtg act gca ggg aag ctg gca cgg gca ccg gcc gac cct       104
Ser Ala Ala Val Thr Ala Gly Lys Leu Ala Arg Ala Pro Ala Asp Pro
        5                  10                  15 ggg aaa gcc ggg gtc ccc gga gtt gca gct ccc gga gct ccg gcg gcg       152
Gly Lys Ala Gly Val Pro Gly Val Ala Ala Pro Gly Ala Pro Ala Ala
    20                  25                  30 gct cca ccg gcg aaa gag atc ccg gag gtc cta gtg gac cca cgc agc       200
Ala Pro Pro Ala Lys Glu Ile Pro Glu Val Leu Val Asp Pro Arg Ser
35                  40                  45 cgg cgg cgc tat gtg cgg ggc cgc ttt ttg ggc aag ggc ggc ttt gcc       248
Arg Arg Arg Tyr Val Arg Gly Arg Phe Leu Gly Lys Gly Gly Phe Ala
50                  55                  60                  65 aag tgc ttc gag atc tcg gac gcg gac acc aag gag gtg ttc gcg ggc       296
Lys Cys Phe Glu Ile Ser Asp Ala Asp Thr Lys Glu Val Phe Ala Gly
            70                  75                  80 aag att gtg cct aag tct ctg ctg ctc aag ccg cac cag agg gag aag       344
```

```
                Lys Ile Val Pro Lys Ser Leu Leu Lys Pro His Gln Arg Glu Lys
                            85                  90                  95 atg tcc atg gaa ata tcc att cac cgc agc ctc gcc cac cag cac gtc      392
Met Ser Met Glu Ile Ser Ile His Arg Ser Leu Ala His Gln His Val
            100                 105                 110 gta gga ttc cac ggc ttt ttc gag gac aac gac ttc gtg ttc gtg gtg      440
Val Gly Phe His Gly Phe Phe Glu Asp Asn Asp Phe Val Phe Val Val
            115                 120                 125 ttg gag ctc tgc cgc cgg agg tct ctc ctg gag ctg cac aag agg agg      488
Leu Glu Leu Cys Arg Arg Arg Ser Leu Leu Glu Leu His Lys Arg Arg
130                 135                 140                 145 aaa gcc ctg act gag cct gag gcc cga tac tac cta cgg caa att gtg      536
Lys Ala Leu Thr Glu Pro Glu Ala Arg Tyr Tyr Leu Arg Gln Ile Val
                150                 155                 160 ctt ggc tgc cag tac ctg cac cga aac cga gtt att cat cga gac ctc      584
Leu Gly Cys Gln Tyr Leu His Arg Asn Arg Val Ile His Arg Asp Leu
                165                 170                 175 aag ctg ggc aac ctt ttc ctg aat gaa gat ctg gag gtg aaa ata ggg      632
Lys Leu Gly Asn Leu Phe Leu Asn Glu Asp Leu Glu Val Lys Ile Gly
                180                 185                 190 gat ttt gga ctg gca acc aaa gtc gaa tat gac ggg gag agg aag aag      680
Asp Phe Gly Leu Ala Thr Lys Val Glu Tyr Asp Gly Glu Arg Lys Lys
195                 200                 205 acc ctg tgt ggg act cct aat tac ata gct ccc gag gtg ctg agc aag      728
Thr Leu Cys Gly Thr Pro Asn Tyr Ile Ala Pro Glu Val Leu Ser Lys
210                 215                 220                 225 aaa ggg cac agt ttc gag gtg gat gtg tgg tcc att ggg tgt atc atg      776
Lys Gly His Ser Phe Glu Val Asp Val Trp Ser Ile Gly Cys Ile Met
                230                 235                 240 tat acc ttg tta gtg ggc aaa cca cct ttt gag act tct tgc cta aaa      824
Tyr Thr Leu Leu Val Gly Lys Pro Pro Phe Glu Thr Ser Cys Leu Lys
            245                 250                 255 gag acc tac ctc cgg atc aag aag aat gaa tac agt att ccc aag cac      872
Glu Thr Tyr Leu Arg Ile Lys Lys Asn Glu Tyr Ser Ile Pro Lys His
            260                 265                 270 atc aac ccc gtg gcc gcc tcc ctc atc cag aag atg ctt cag aca gat      920
Ile Asn Pro Val Ala Ala Ser Leu Ile Gln Lys Met Leu Gln Thr Asp
275                 280                 285 ccc act gcc cgc cca acc att aac gag ctg ctt aat gac gag ttc ttt      968
Pro Thr Ala Arg Pro Thr Ile Asn Glu Leu Leu Asn Asp Glu Phe Phe
290                 295                 300                 305 act tct ggc tat atc cct gcc cgt ctc ccc atc acc tgc ctg acc att      1016
Thr Ser Gly Tyr Ile Pro Ala Arg Leu Pro Ile Thr Cys Leu Thr Ile
                310                 315                 320 cca cca agg ttt tcg att gct ccc agc agc ctg gac ccc agc aac cgg      1064
Pro Pro Arg Phe Ser Ile Ala Pro Ser Ser Leu Asp Pro Ser Asn Arg
            325                 330                 335 aag ccc ctc aca gtc ctc aat aaa ggc ttg gag aac ccc ctg cct gag      1112
Lys Pro Leu Thr Val Leu Asn Lys Gly Leu Glu Asn Pro Leu Pro Glu
            340                 345                 350 cgt ccc cgg gaa aaa gaa gaa cca gtg gtt cga gag aca ggt gag gtg      1160
Arg Pro Arg Glu Lys Glu Glu Pro Val Val Arg Glu Thr Gly Glu Val
            355                 360                 365 gtc gac tgc cac ctc agt gac atg ctg cag cag ctg cac agt gtc aat      1208
Val Asp Cys His Leu Ser Asp Met Leu Gln Gln Leu His Ser Val Asn
370                 375                 380                 385 gcc tcc aag ccc tcg gag cgt ggg ctg gtc agg caa gag gag gct gag      1256
Ala Ser Lys Pro Ser Glu Arg Gly Leu Val Arg Gln Glu Glu Ala Glu
                390                 395                 400
```

```
gat cct gcc tgc atc ccc atc ttc tgg gtc agc aag tgg gtg gac tat      1304
Asp Pro Ala Cys Ile Pro Ile Phe Trp Val Ser Lys Trp Val Asp Tyr
            405                 410                 415 tcg gac aag tac ggc ctt ggg tat cag ctc tgt gat aac agc gtg ggg      1352
Ser Asp Lys Tyr Gly Leu Gly Tyr Gln Leu Cys Asp Asn Ser Val Gly
        420                 425                 430 gtg ctc ttc aat gac tca aca cgc ctc atc ctc tac aat gat ggt gac      1400
Val Leu Phe Asn Asp Ser Thr Arg Leu Ile Leu Tyr Asn Asp Gly Asp
    435                 440                 445 agc ctg cag tac ata gag cgt gac ggc act gag tcc tac ctc acc gtg      1448
Ser Leu Gln Tyr Ile Glu Arg Asp Gly Thr Glu Ser Tyr Leu Thr Val
450                 455                 460                 465 agt tcc cat ccc aac tcc ttg atg aag aag atc acc ctc ctt aaa tat      1496
Ser Ser His Pro Asn Ser Leu Met Lys Lys Ile Thr Leu Leu Lys Tyr
                470                 475                 480 ttc cgc aat tac atg agc gag cac ttg ctg aag gca ggt gcc aac atc      1544
Phe Arg Asn Tyr Met Ser Glu His Leu Leu Lys Ala Gly Ala Asn Ile
            485                 490                 495 acg ccg cgc gaa ggt gat gag ctc gcc cgg ctg ccc tac cta cgg acc      1592
Thr Pro Arg Glu Gly Asp Glu Leu Ala Arg Leu Pro Tyr Leu Arg Thr
        500                 505                 510 tgg ttc cgc acc cgc agc gcc atc atc ctg cac ctc agc aac ggc agc      1640
Trp Phe Arg Thr Arg Ser Ala Ile Ile Leu His Leu Ser Asn Gly Ser
    515                 520                 525 gtg cag atc aac ttc ttc cag gat cac acc aag ctc atc ttg tgc cca      1688
Val Gln Ile Asn Phe Phe Gln Asp His Thr Lys Leu Ile Leu Cys Pro
530                 535                 540                 545 ctg atg gca gcc gtg acc tac atc gac gag aag cgg gac ttc cgc aca      1736
Leu Met Ala Ala Val Thr Tyr Ile Asp Glu Lys Arg Asp Phe Arg Thr
                550                 555                 560 tac cgc ctg agt ctc ctg gag gag tac ggc tgc tgc aag gag ctg gcc      1784
Tyr Arg Leu Ser Leu Leu Glu Glu Tyr Gly Cys Cys Lys Glu Leu Ala
            565                 570                 575 agc cgg ctc cgc tac gcc cgc act atg gtg gac aag ctg ctg agc tca      1832
Ser Arg Leu Arg Tyr Ala Arg Thr Met Val Asp Lys Leu Leu Ser Ser
        580                 585                 590 cgc tcg gcc agc aac cgt ctc aag gcc tcc taa tagctgccct cccctccgga   1885
Arg Ser Ala Ser Asn Arg Leu Lys Ala Ser
    595                 600 ctggtgccct cctcactccc acctgcatct ggggcccata ctggttggct cccgcggtgc    1945
catgtctgca gtgtgccccc cagccccggt ggctgggcag agctgcatca tccttgcagg    2005
tgggggttgc tgtgtaagtt atttttgtac atgttcgggt gtgggttcta cagccttgtc    2065
cccctccccc tcaaccccac catatgaatt gtacagaata tttctattga attcggaact    2125
gtcctttcct tggctttatg cacattaaac agatgtgaat attcaaaaaa aaaaaaaaa     2185 aaaaaaaaa aaaaaaaa                                                   2204

<210> SEQ ID NO 78
<211> LENGTH: 603
<212> TYPE: PRT
<213> ORGANISM: Homo sapiens

<400> SEQUENCE: 78

Met Ser Ala Ala Val Thr Ala Gly Lys Leu Ala Arg Ala Pro Ala Asp
1               5                   10                  15

Pro Gly Lys Ala Gly Val Pro Gly Val Ala Pro Gly Ala Pro Ala
            20                  25                  30

Ala Ala Pro Pro Ala Lys Glu Ile Pro Glu Val Leu Val Asp Pro Arg
```

-continued

```
                35                  40                  45
Ser Arg Arg Arg Tyr Val Arg Gly Arg Phe Leu Gly Lys Gly Gly Phe
 50                  55                  60
Ala Lys Cys Phe Glu Ile Ser Asp Ala Asp Thr Lys Glu Val Phe Ala
 65                  70                  75                  80
Gly Lys Ile Val Pro Lys Ser Leu Leu Leu Lys Pro His Gln Arg Glu
                 85                  90                  95
Lys Met Ser Met Glu Ile Ser Ile His Arg Ser Leu Ala His Gln His
                100                 105                 110
Val Val Gly Phe His Gly Phe Phe Glu Asp Asn Asp Phe Val Phe Val
                115                 120                 125
Val Leu Glu Leu Cys Arg Arg Arg Ser Leu Leu Glu Leu His Lys Arg
                130                 135                 140
Arg Lys Ala Leu Thr Glu Pro Glu Ala Arg Tyr Tyr Leu Arg Gln Ile
145                 150                 155                 160
Val Leu Gly Cys Gln Tyr Leu His Arg Asn Arg Val Ile His Arg Asp
                165                 170                 175
Leu Lys Leu Gly Asn Leu Phe Leu Asn Glu Asp Leu Glu Val Lys Ile
                180                 185                 190
Gly Asp Phe Gly Leu Ala Thr Lys Val Glu Tyr Asp Gly Glu Arg Lys
                195                 200                 205
Lys Thr Leu Cys Gly Thr Pro Asn Tyr Ile Ala Pro Glu Val Leu Ser
210                 215                 220
Lys Lys Gly His Ser Phe Glu Val Asp Val Trp Ser Ile Gly Cys Ile
225                 230                 235                 240
Met Tyr Thr Leu Leu Val Gly Lys Pro Pro Phe Glu Thr Ser Cys Leu
                245                 250                 255
Lys Glu Thr Tyr Leu Arg Ile Lys Lys Asn Glu Tyr Ser Ile Pro Lys
                260                 265                 270
His Ile Asn Pro Val Ala Ala Ser Leu Ile Gln Lys Met Leu Gln Thr
                275                 280                 285
Asp Pro Thr Ala Arg Pro Thr Ile Asn Glu Leu Leu Asn Asp Glu Phe
                290                 295                 300
Phe Thr Ser Gly Tyr Ile Pro Ala Arg Leu Pro Ile Thr Cys Leu Thr
305                 310                 315                 320
Ile Pro Pro Arg Phe Ser Ile Ala Pro Ser Ser Leu Asp Pro Ser Asn
                325                 330                 335
Arg Lys Pro Leu Thr Val Leu Asn Lys Gly Leu Glu Asn Pro Leu Pro
                340                 345                 350
Glu Arg Pro Arg Glu Lys Glu Pro Val Val Arg Glu Thr Gly Glu
                355                 360                 365
Val Val Asp Cys His Leu Ser Asp Met Leu Gln Gln Leu His Ser Val
                370                 375                 380
Asn Ala Ser Lys Pro Ser Glu Arg Gly Leu Val Arg Gln Glu Glu Ala
385                 390                 395                 400
Glu Asp Pro Ala Cys Ile Pro Ile Phe Trp Val Ser Lys Trp Val Asp
                405                 410                 415
Tyr Ser Asp Lys Tyr Gly Leu Gly Tyr Gln Leu Cys Asp Asn Ser Val
                420                 425                 430
Gly Val Leu Phe Asn Asp Ser Thr Arg Leu Ile Leu Tyr Asn Asp Gly
                435                 440                 445
Asp Ser Leu Gln Tyr Ile Glu Arg Asp Gly Thr Glu Ser Tyr Leu Thr
                450                 455                 460
```

```
Val Ser Ser His Pro Asn Ser Leu Met Lys Lys Ile Thr Leu Leu Lys
465                 470                 475                 480

Tyr Phe Arg Asn Tyr Met Ser Glu His Leu Leu Lys Ala Gly Ala Asn
                485                 490                 495

Ile Thr Pro Arg Glu Gly Asp Glu Leu Ala Arg Leu Pro Tyr Leu Arg
            500                 505                 510

Thr Trp Phe Arg Thr Arg Ser Ala Ile Ile Leu His Leu Ser Asn Gly
        515                 520                 525

Ser Val Gln Ile Asn Phe Phe Gln Asp His Thr Lys Leu Ile Leu Cys
    530                 535                 540

Pro Leu Met Ala Ala Val Thr Tyr Ile Asp Glu Lys Arg Asp Phe Arg
545                 550                 555                 560

Thr Tyr Arg Leu Ser Leu Leu Glu Glu Tyr Gly Cys Cys Lys Glu Leu
                565                 570                 575

Ala Ser Arg Leu Arg Tyr Ala Arg Thr Met Val Asp Lys Leu Leu Ser
            580                 585                 590

Ser Arg Ser Ala Ser Asn Arg Leu Lys Ala Ser
        595                 600
```

METHOD OF PREDICTING A RESPONSE TO AN ANTI-TUMOR TREATMENT

CROSS-REFERENCE TO RELATED APPLICATION

This application is the U.S. national stage application of International Patent Application No. PCT/EP2014/077024, filed Dec. 9, 2014.

FIELD OF THE INVENTION

The present invention relates to a method of predicting a response to an anti-tumor treatment, more particularly to the identification of markers for predicting whether certain pro-apoptotic peptides would be effective for treating a tumor in a patient.

BACKGROUND OF THE INVENTION

Apoptosis is a genetically programmed cell death and its deregulation is associated among other pathologies, with cancer. While apoptosis is known to rely on the Bcl-2 family members and caspases, data suggest that two major families of serine/threonine phosphatases, PP1 and PP2A, are key actors involved in cell life or cell death decision. The Ser/Thre phosphatase PP2A has been implicated in both induction and prevention of apoptosis, pointing to a complex interplay of phosphatase actions. PP2A was shown to interact with caspase-9 through a particular sequence from the C-terminal portion of caspase-9. This sequence was identified as being YVETLDGIFEQWAHSEDL (SEQ ID NO: 1 for human caspase-9. This binding domain to PP2Ac corresponds to amino acid positions 363-380 of human caspase-9 (NCBI accession number NP 001 220) and is described in international patent application WO2010/112471. The counterpart sequence from the human PP2Ac subunit which interacts with its partner caspase-9 was then identified as being DTLDHIRALDRLQEVPHEGP (SEQ ID NO: 2), positions 175-194 of human PPA2c sequence (Swiss-Prot accession number P67775-1), as described in international patent application WO2012/042038. These interaction motifs between caspase 9 and PP2A have been proposed as pro-apoptotic peptides, and have proved very promising, in particular when fused to cell penetrating peptides.

As the choices of treatment for cancer have expanded, the need to identify predictive biomarkers to tailor treatment strategies to individual tumor has become necessary. Such strategies have the potential of maximizing antitumor effect while minimizing toxicity and improving clinical benefit. Advances in molecular therapeutics in the past decades have opened up possibilities for treating cancer patients with personalized therapies.

Some examples of predictive biomarkers being used in the daily clinical oncology practice are estrogen and progesterone receptors to predict sensitivity to endocrine therapy in breast cancer, HER2 to predict sensitivity to Herceptin treatment and KRAS mutation to predict resistance to EGFR antibody therapy. Such signatures predicting anti-cancer therapy response a priori or early in treatment enable an evidence-based decision making on available treatment options.

Similarly, there is a need for methods of predicting whether a patient would respond or not to a treatment with pro-apoptotic peptides.

SUMMARY OF THE INVENTION

It is now provided an in vitro method for determining the likelihood for a patient affected with a tumor to respond to a treatment with a pro-apoptotic peptide able to disrupt interaction between caspase 9 and PP2A. According to the invention, this method comprises determining expression level of at least each of VIM, MK167, TCF7L2, NEK2, BIRC5, MCL1, and PLK1 genes, in a biological sample of said patient.

As will be described in greater details below, the pro-apoptotic peptide may comprise a binding domain to PP2A, or a binding domain to caspase 9.

Preferably, the pro-apoptotic peptide is fused to a cell-penetrating peptide, whereby forming a chimeric peptide.

In a particular embodiment, the chimeric peptide is VKK-KKIKREIKI-YVETLDGIFEQWAHSEDL (SEQ ID NO: 49), also designated DPT-C9h.

The tumor may be any tumor or cancer, such as a breast tumor, an ovarian tumor, a lung tumor or a prostate tumor.

The invention further provides a method for monitoring the patient's response to the treatment.

At last it is provided a kit for use in such methods, comprising primers and/or probes specific of each of VIM, MK167, TCF7L2, NEK2, BIRC5, MCL1, and PLK1 genes.

It is further provided a method for treating a patient affected with a tumor, which method comprises administering a pro-apoptotic or chimeric peptide as described herein, optionally in combination with an anti-tumor agent, such as a chemotherapeutic agent, to said patient, wherein said patient has been previously classified as "responder" by the method described herein, comprising determining expression level of at least each of VIM, MK167, TCF7L2, NEK2, BIRC5, MCL1, and PLK1 genes, in a biological sample of said patient, before or during the course of the treatment.

DETAILED DESCRIPTION OF THE INVENTION

Definitions:

The term "patient" refers to a human or non human animal, preferably a mammal, including male, female, adult and children in need of a treatment wherein a pro-apoptotic effect is desired.

As used herein, the term "treatment" or "therapy" includes curative and/or prophylactic treatment. More particularly, curative treatment refers to any of the alleviation, amelioration and/or elimination, reduction and/or stabilization (e.g., failure to progress to more advanced stages) of a symptom, as well as delay in progression of a symptom of a particular disorder.

Prophylactic treatment refers to any of: halting the onset, reducing the risk of development, reducing the incidence, delaying the onset, reducing the development, as well as increasing the time to onset of symptoms of a particular disorder.

The term "responder, or responsive to a treatment" refers to a subject in whom the onset of at least one of the symptoms is delayed or prevented, upon or after treatment, or whose symptoms or at least one of the symptom stabilize, diminish or disappear, or whose tumor growth, volume or spread stops or decreases, e.g. decreases of at least 30% in the sum of lesion diameter (RECIST criteria).

The term "resistant to a treatment" or "non-responsive to a treatment" refers to a subject in whom the onset of symptoms is not delayed nor prevented, upon or after treatment, who shows no stabilization, diminution, nor disappearance of any of the symptoms, and whose tumor growth, volume and spread does not stop nor decrease, in particular does not decrease of more than 30% in the sum of lesion diameter (RECIST criteria).

The term "penetrating peptide" or "cell-penetrating peptide" (or "CPP") or "shuttle peptide", as used interchangeably, means that the peptide is able to translocate into cells without causing substantial membrane damage, and can be used as a vector of other molecules when linked to them. The terms refer to cationic cell penetrating peptides, also called transport peptides, carrier peptides, or peptide transduction domains. The CPP, as shown herein, have the capability of inducing cell penetration of a peptide fused to the CPP within 30%, 40%, 50%, 60%, 70%, 80%, 90%, or 100% of cells of a given cell culture population, including all integers in between, and allow macromolecular translocation within multiple tissues in vivo upon systemic administration. A cell-penetrating peptide may also refers to a peptide which, when brought into contact with a cell under appropriate conditions, passes from the external environment in the intracellular environment, including the cytoplasm, organelles such as mitochondria, or the nucleus of the cell, in conditions significantly greater than passive diffusion. This property may be assessed by various methods known by the skilled person.

Two amino acid sequences are "homologous", "substantially homologous" or "substantially similar" when one or more amino acid residue are replaced by a biologically similar residue or when greater than 80% of the amino acids are identical, or greater than about 90%, preferably greater than about 95%, are similar (functionally identical). Preferably, the similar or homologous sequences are identified by alignment using, for example, the GCG (Genetics Computer Group, Program Manual for the GCG Package, Version 7, Madison, Wis.) pileup program, or any of the programs known in the art (BLAST, FASTA, etc.). Preferably, these homologous peptides do not include two cysteine residues, so that cyclization is prevented.

The term "conservative substitution" as used herein denotes the replacement of an amino acid residue by another, without altering the overall conformation and function of the peptide, including, but not limited to, replacement of an amino acid with one having similar properties (such as, for example, polarity, hydrogen bonding potential, acidic, basic, shape, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Neutral hydrophilic amino acids, which can be substituted for one another, include asparagine, glutamine, serine and threonine.

By "substituted" or "modified" the present invention includes those amino acids that have been altered or modified from naturally occurring amino acids.

As such, it should be understood that in the context of the present invention, a conservative substitution is recognized in the art as a substitution of one amino acid for another amino acid that has similar properties. Examples of conservative substitutions are set out in the Table A below:

TABLE A

Conservative Substitutions I

| SIDE CHAIN CHARACTERISTIC | AMINO ACID |
|---|---|
| Non-polar | G A P I L V |
| Polar-uncharged | C S T M N Q |
| Polar-charged | D E K R |
| Aromatic | H F W Y |
| Other | N Q D E |

Alternatively, conservative amino acids can be grouped as described in Lehninger, 1975, as set out in Table B, immediately below.

TABLE B

Conservative Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W |
| C. Sulfur-containing. | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

As still another alternative, exemplary conservative substitutions are set out in Table C, immediately below.

TABLE C

Conservative Substitutions III

| Original Residue | Exemplary Substitution |
|---|---|
| Ala (A) | Val (V), Leu (L), Ile (I) |
| Arg (R) | Lys (K), Gln (Q), Asn (N) |
| Asn (N) | Gln (Q), His (H), Lys (K), Arg (R) |
| Asp (D) | Glu (E) |
| Cys (C) | Ser (S) |
| Gln (Q) | Asn (N) |
| Glu (E) | Asp (D) |
| His (H) | Asn (N), Gln (Q), Lys (K), Arg (R) |
| Ile (I) | Leu (L), Val (V), Met (M), Ala (A), Phe (F) |
| Leu (L) | Ile (I), Val (V), Met (M), Ala (A), Phe (F) |
| Lys (K) | Arg (R), Gln (Q), Asn (N) |
| Met (M) | Leu (L), Phe (F), Ile (I) |
| Phe (F) | Leu (L), Val (V), Ile (I), Ala (A) |
| Pro (P) | Gly (G) |
| Ser (S) | Thr (T) |
| Thr (T) | Ser (S) |
| Trp (W) | Tyr (T) |
| Tyr (Y) | Trp (W), Phe (F), Thr (T), Ser (S) |
| Val (V) | Ile (I), Leu (L), Met (M), Phe (F), Ala (A) |

The Predictive Signature:

It has now been found that marker sets consisting of particular genes differentially expressed in tumors advantageously provide improved accuracy of predicting effectiveness of a treatment against a cancer with a pro-apoptotic peptide as defined herein.

The marker sets of the present invention may be used in a clinical setting to provide information about the likelihood that a cancer patient would or would not respond to a treatment with such pro-apoptotic peptide. The marker sets of the present invention makes it possible to classify the patient as either a potential responder or a non-responder.

The method involves determining the expression level of at least each of VIM, MK167, TCF7L2, NEK2, BIRC5, MCL1, and PLK1 genes, in a biological sample of said patient.

The term "each of VIM, MK167, TCF7L2, NEK2, BIRC5, MCL1, and PLK1 genes" means that the expression level of all said genes is assessed.

VIM is the gene that encodes vimentin, which is responsible for maintaining cell shape, integrity of the cytoplasm, and stabilizing cytoskeletal interactions. A sequence of human VIM mRNA is available on Genbank Access Number NM_003380 (SEQ ID NO: 63 and 64).

MK167 (marker of proliferation Ki-67) encodes a nuclear protein that is associated with and may be necessary for cellular proliferation. Human alternatively spliced transcript variants have been described. The longer transcript is described in Genbank as NM_002417 (SEQ ID NO: 65 and 66), the shorter is described as NM_001145966 (SEQ ID NO: 67 and 68).

TCF7L2 (transcription factor 7-like 2 (T-cell specific, HMG-box) gene encodes a high mobility group (HMG) box-containing transcription factor that plays a key role in the Wnt signaling pathway. Several transcript variants encoding multiple different isoforms have been found for this gene. Variant 1 encodes the longest isoform (Genbank access number NM_001146274) (SEQ ID NO: 69 and 70).

NEK2 (NIMA-related kinase 2) encodes a serine/threonine-protein kinase that is involved in mitotic regulation. This protein is localized to the centrosome, and undetectable during G1 phase, but accumulates progressively throughout the S phase, reaching maximal levels in late G2 phase. Alternatively spliced transcript variants encoding different isoforms with distinct C-termini have been noted for this gene. Variant 1 disclosed as NM_002497 on Genbank represents the predominant transcript, and encodes the longest isoform (1, also known as NEK2A). (SEQ ID NO: 71 and 72).

BIRC5 (Homo sapiens baculoviral IAP repeat containing 5) encodes a negative regulatory protein that prevents apoptosis. Alternatively spliced transcript variants encoding distinct isoforms have been found for this gene. The most frequently occurring transcript is shown as NM_001168 in Genbank (SEQ ID NO: 73 and 74). MCL1, also designated myeloid cell leukemia sequence 1 (BCL2-related) encodes an anti-apoptotic protein, which is a member of the Bcl-2 family. Alternative splicing results in multiple transcript variants. The longest gene product (isoform 1) enhances cell survival by inhibiting apoptosis while the alternatively spliced shorter gene products (isoform 2 and isoform 3) promote apoptosis and are death-inducing. The longest transcript which encodes the longest isoform is variant 1, disclosed as NM_021960 on Genbank (SEQ ID NO: 75 and 76).

PLK1 is a protooncogene that encodes polo-like kinase 1, also known as serine/threonine-protein kinase. A Homo sapiens mRNA sequence thereof is shown as NM_005030 on Genbank (SEQ ID NO: 77 and 78).

The biological sample is preferably a sample comprising tumor DNA or RNA, preferably a tumor tissue biopsy. For instance, it may be formalin-fixed paraffin embedded tumor tissue or fresh frozen tumor tissue.

The method then generally involves comparing the expression level of said genes to at least one control value.

The term "control value" is a reference value corresponding to the expression level of each of said genes in a group of tumors showing a predetermined response profile, i.e. a group of responder patients or a group of resistant patients (unlikely to respond to the treatment).

Based on the gene expression levels, the classification of the patient may be determined using any commonly used suitable algorithm, such as, for example, the nearest shrunken centroid (NSC) algorithm or Prediction Analysis of Microarrays" (PAM), the support vector machine (SVM) algorithm, or the k-nearest neighbour algorithm. Preferably, PAM is used, as described in Tibshirani et al., PNAS 2002, 99(10):6567-6572). "Prediction Analysis of Microarrays" (PAM) performs sample classification from gene expression data using the nearest shrunken centroid method.

The method further comprises determining whether the expression levels of said genes are high or low compared to the reference expression level(s). For instance, a decreased expression of said genes compared to the control value may be indicative of a patient being likely to respond to the treatment, or wherein an increased expression of said genes compared to the control value may be indicative of a patient being unlikely to respond to the treatment.

The reference expression level(s) may be the expression level of a gene having a stable expression in responsive patients and/or the expression level of a gene having a stable expression in resistant patients. Scores can be predetermined, as described in greater details in the experimental section below.

The reference expression levels may also be the mean expression levels of said genes among a cohort of human tumor samples. The combined expression profile of these genes is informative of the status of the patient who, before any treatment, can be classified as (i) likely to respond, and for whom a treatment with a pro-apoptotic peptide described herein is recommended, and (ii) unlikely to respond, and for whom a treatment with such pro-apoptotic peptides is not recommended.

The combined expression profile of these genes may also be informative to monitor the efficacy of said treatment, during the course of the treatment. In that situation, the term "control value" may refer to the expression level of the genes at a different time.

In a particular embodiment, the method may further comprise determining the expression level of at least one other gene, preferably selected from the group consisting of VCAM, VEGFA, TNFAIP3, and BBC3.

Determination of Expression:

Determination of the level of expression of a gene can be performed by a variety of techniques, from a biological sample.

Preferably, the determination comprises contacting the sample with selective reagents such as probes, primers or ligands, and thereby measuring the amount, of nucleic acids of interest originally in the sample. Contacting may be performed in any suitable device, such as a plate, microtiter dish, test tube, well, glass, column, and so forth In specific embodiments, the contacting is performed on a substrate coated with the reagent, such as a nucleic acid array or a specific ligand array. The substrate may be a solid or semi-solid substrate such as any suitable support comprising glass, plastic, nylon, paper, metal, polymers and the like. The substrate may be of various forms and sizes, such as a slide, a membrane, a bead, a column, a gel, etc. The contacting may be made under any condition suitable for a detectable complex, such as a nucleic acid hybrid, to be formed between the reagent and the nucleic acids of the sample.

The expression may be typically determined by measuring the quantity of mRNA.

Methods for measuring the quantity of mRNA are well known in the art. For example the nucleic acid contained in the samples (e.g., cell or tissue prepared from the patient) is first extracted according to standard methods, for example using lytic enzymes or chemical solutions or extracted by nucleic-acid-binding resins following the manufacturer's instructions. The extracted mRNA is then detected by hybridization (e. g., Northern blot analysis) and/or amplification (e.g., RT-PCR). Preferably quantitative or semi-quantitative RT-PCR is preferred. Real-time quantitative or semi-quantitative RT-PCR is particularly advantageous. Other methods of Amplification include ligase chain reaction (LCR), transcription-mediated amplification, strand displacement amplification (SDA) and nucleic acid sequence based amplification (NASBA).

Nucleic acids having at least 10 nucleotides and exhibiting sequence complementarity or homology to the mRNA of interest herein find utility as hybridization probes or amplification primers. It is understood that such nucleic acids need not be identical, but are typically at least about 80% identical to the homologous region of comparable size, more preferably 85% identical and even more preferably 90-95% identical. In certain embodiments, it will be advantageous to use nucleic acids in combination with appropriate means, such as a detectable label, for detecting hybridization. A wide variety of appropriate indicators are known in the art including, fluorescent, radioactive, enzymatic or other ligands (e. g. avidin/biotin).

The preferred method uses quantitative RT-PCR employing primers of about at least 10 nucleotides that specifically hybridize with of a region of the gene to detect (e.g. that specifically hybridize with SEQ ID NO: 63, 65, 67, 69, 71, 73, 75 or 77 respectively). Two primers that anneal to opposite strands of the target region so as to form an amplification product during a PCR reaction. The amplicon size is typically between about 60 to about 500 bp, preferably about 80 to about 250 bp.

The primer oligonucleotides generally comprise from 10 to 40 nucleotides, preferably from 10 to 30 nucleotides, still preferably from 15 to 25 nucleotides. The primer oligonucleotides preferably have a melting temperature (Tm) around 56-64° C. The primer oligonucleotides are preferably 100% complementary to a portion of the target sequence.

The RT-qPCR can also advantageously use a probe that is an oligonucleotide that anneals to a sequence on the target DNA found between the forward (5') and reverse (3') PCR primer binding sites. Tm of the probe is generally higher than Tm of the primers.

The PCR described herein is thus preferably repeated for two or more cycles, preferably from 10 to 50 cycles. The length and temperature of each step of a PCR cycle, as well as the number of cycles, are adjusted according to the stringency requirements in effect. Annealing temperature and timing are determined both by the efficiency with which a primer is expected to anneal to a template. An annealing temperature of between 30° C. and 72° C. is used. Initial denaturation of the template molecules normally occurs at between 92° C. and 99° C. for about 15 seconds, preferably for about 1 or 4 minutes to about 10-15 minutes, followed by 20-50 cycles consisting of denaturation (94-99° C. for 15 seconds to 1 minute), annealing (e.g. 60° C.; from 15 s to 2 minutes), and extension (72° C. for 1 minute) for a simple PCR (the extension and the annealing occurring at the same time, in a 60° C. step, for 1 min, in a q-PCR). An optional final extension step (useful in simple PCR) is generally carried out for about 4 minutes at 72° C., and may be followed by an indefinite (0-24 hour) step at 4° C.

Real-time reaction conditions further utilize a nucleic acid detection agent (e.g., dye or probe) in order to measure/detect the PCR product as it is produced. In another embodiment, the expression level is determined by DNA chip analysis. Such DNA chip or nucleic acid microarray consists of different nucleic acid probes that are chemically attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes comprise nucleic acids such as cDNAs or oligonucleotides that may be about 10 to about 60 base pairs. To determine the expression level, a sample from a test subject, optionally first subjected to a reverse transcription, is labelled and contacted with the microarray in hybridization conditions, leading to the formation of complexes between target nucleic acids that are complementary to probe sequences attached to the microarray surface. The labelled hybridized complexes are then detected and can be quantified or semi-quantified. Labelling may be achieved by various methods, e.g. by using radioactive or fluorescent labelling. Many variants of the microarray hybridization technology are available to the man skilled in the art.

In a particular embodiment, the expression level is determined by determining the number of copies of the genes. Comparative genomic hybridization (CGH) was developed to survey DNA copy-number variations across a whole genome. With CGH, differentially labelled test and reference genomic DNAs are co-hybridized to normal metaphase chromosomes, and fluorescence ratios along the length of chromosomes provide a cytogenetic representation of DNA copy-number variation. Array-based CGH, in which fluorescence ratios at arrayed DNA elements provide a locus-by-locus measure of DNA copy-number variation, represents another means of achieving increased mapping resolution.

In a particular embodiment, the level of expression is determined by assessing the quantity of protein expressed by said gene, e.g. by Western blot. Measuring the quantity of protein may be performed in place, or in addition, to measuring the quantity of mRNA.

The Patient:

The patient to treat, who is preferably a human patient, is affected with a tumor, in particular a cancer tumor.

The tumor may be a haematologic cancer, in particular acute myelogenous leukaemia (AML), chronic lymphocytic leukaemia (CLL), multiple myeloma, Hodgkin's disease, non-Hodgkin's lymphoma, B cell, cutaneous T cell lymphoma, or a non-haematologic cancer, for instance brain, epidermoid (in particular lung, breast, ovarian), head and neck (squamous cell), bladder, gastric, pancreatic, head, neck, renal, colon, prostate, colorectal, oesophageal or thyroid cancer, and melanoma.

Different types of cancers may include, but are not limited to fibrosarcoma, myxosarcoma, liposarcoma, chondrosarcoma, osteogenic sarcoma, chordoma, angiosarcoma, endotheliosarcoma, lymphangiosarcoma, lymphangioendothelio-sarcoma, synovioma, mesothelioma, Ewing's tumor, leiomyosarcoma, rhabdomyosarcoma, lymphoma, leukemia, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma, uveal melanoma and breast cancer.

In a preferred embodiment, the cancer tumor is a breast cancer.

Pro-Apoptotic Peptide:

It is now provided an in vitro method for determining the likelihood for a patient affected with a tumor to respond to a treatment with a pro-apoptotic peptide able to disrupt interaction between caspase 9 and PP2A, or a method for monitoring the efficacy of said treatment.

In a first embodiment, the pro-apoptotic peptide comprises a binding domain to PP2A, more particularly, it may comprise a PP2A binding domain of a caspase-9 protein, or may derive therefrom.

Accordingly, the pro-apoptotic peptide may comprise, or consist in the following amino acid sequence:

$$Y-X_{4a}-ETLD-X_{4b}-I-X_5-EQWA-X_6-S-X_7 \quad \text{(SEQ ID NO: 3)}$$

wherein
$X_{4a}$ is valine or isoleucine;
$X_{4b}$ is aspartic acid or glycine;
$X_5$ is phenylalanine or leucine;
$X_6$ is arginine or histidine;
$X_7$ is vacant or is glutamate, or glutamate-aspartate, or glutamate-aspartate-leucine; or
a proteolysis-resistant peptide deriving from said pro-apoptotic peptide by one or more chemical modifications, or a substantially homologous peptide, preferably at least 80% identical to SEQ ID NO: 3 while still inducing cell apoptosis, still preferably deriving from SEQ ID NO:3 by one or more conservative substitutions.

Such proteolysis-resistant or homologous peptides induce cell apoptosis, in vitro and/or in vivo. Assays for determining if a molecule, for instance a peptide, induces cell apoptosis are well-known in the art and include, for instance, incubating cells with the candidate peptide and determining if apoptosis is induced by said candidate peptide, e.g. by Annexin V and PI labelling of cells and identifying as apoptotic cells, those being Annexin V$^+$ and PI$^-$.

In a preferred embodiment, $X_{4a}$ is valine; $X_{4b}$ is aspartic acid; $X_5$ is phenylalanine; and $X_6$ is histidine.

The pro-apoptotic peptide may then advantageously comprise or consist of sequence YVETLDDIFEQWAHSEDL (SEQ ID NO: 4) or YVETLDGIFEQWAHSEDL (SEQ ID NO: 1).

In a second embodiment, the pro-apoptotic peptide comprises a binding domain to caspase-9, more particularly, it may comprise a caspase-9 binding domain of a PP2A protein, or may derive therefrom.

Accordingly, the pro-apoptotic peptide may comprise, or consist in the following amino acid sequence:
the amino acid sequence DTLDHIRALDRLQEVPHEGP (SEQ ID NO: 5);
a proteolysis-resistant peptide deriving from said pro-apoptotic peptide by one or more chemical modifications, or a substantially homologous peptide, preferably at least 80% identical to SEQ ID NO: 5 while still inducing cell apoptosis, still preferably deriving from SEQ ID NO:5 by one or more conservative substitutions.

Such proteolysis-resistant or homologous peptides induce cell apoptosis, in vitro and/or in vivo. Assays for determining if a molecule, for instance a peptide, induces cell apoptosis are well-known in the art and include, for instance, incubating cells with the candidate peptide and determining if apoptosis is induced by said candidate peptide, e.g. by Annexin V and PI labelling of cells and identifying as apoptotic cells, those being Annexin V$^+$ and PI$^-$.

Preferably, it induces apoptosis in Daudi cells as well as in primary cells isolated from xenograft models of lung cancer, uveal melanoma and breast cancer. Preferably, the peptide comprises or consists of a sequence at least 80% identical to SEQ ID NO: 5, or a proteolysis-resistant peptide derived therefrom by one or more chemical modifications. The sequence at least 80% identical to SEQ ID NO: 5 may be in particular a natural variant of amino acid positions 175-194 of human PP2Ac (Swiss-Prot P67775-1), or the sequence corresponding to amino acid positions 175-194 of human PP2Ac in a mammalian counterpart {e.g. mouse, rat, monkey, cat, dog, horse) sequence of In particular, the peptide comprising or consisting of a sequence at least 80% identical to SEQ ID NO: 5 may have a deletion of one, two, three or four amino acids of the N-terminal or C-terminal part of SEQ ID NO: 5, for example, said peptide may be TLDHIRALDRLQEVPHEGP (SEQ ID NO: 6), LDHIRALDRLQEVPHEGP (SEQ ID NO: 7), DHIRALDRLQEVPHEGP (SEQ ID NO: 8), HIRALDRLQEVPHEGP (SEQ ID NO: 9), DTLDHIRALDRLQEVPHEG (SEQ ID NO: 10), DTLDHIRALDRLQEVPHE (SEQ ID NO: 11), DTLDHIRALDRLQEVPH (SEQ ID NO: 12), or DTLDHIRALDRLQEVP (SEQ ID NO: 13). The peptide comprising or consisting of a sequence at least 80% identical to SEQ ID NO: 5 may also have a deletion of one or two amino acids on the C-terminal part of SEQ ID NO:5 and a deletion of one or two amino acids of the N-terminal part of SEQ ID NO:3, for example said PP2Ac peptide may have the sequence TLDHIRALDRLQEVPHEG (SEQ ID NO: 14), LDHIRALDRLQEVPHE (SEQ ID NO: 15), TLDHIRALDRLQEVPHE (SEQ ID NO: 16), or LDHIRALDRLQEVPHEG (SEQ ID NO: 17).

In a particularly preferred embodiment, the peptide comprising or consisting of a sequence at least 80% identical to SEQ ID NO:5 is LDHIRALDRLQEVPHEGP (SEQ ID NO: 7). Preferably, the peptide comprises or consists of the sequence DTLDHIRALDRLQEVPHEGP (SEQ ID NO:5).

Cell Penetrating Peptides:

In preferred embodiments, the pro-apoptotic peptide is linked with at least one cell penetrating peptide, forming a chimeric peptide construct.

Cell penetrating peptides (CPP) are molecules which can translocate into cells without causing membrane damage, leading to their proposed use as vectors for delivering therapeutic cargo. Several CPP have been identified such as Tat, antennapedia, or SHV1 VP22. These peptides can cross the cell membrane and reach the cytoplasm and/or the nucleus. This approach, named "Drug Phosphatase Technology" (DPT), was described in International patent applications WO2003/011898 and WO2004/01 1595.

Preferably the pro-apoptotic peptide is fused at the C-term of the penetrating peptide.

In a particular embodiment, the pro-apoptotic peptide may be linked to two, three or more penetrating peptides.

Preferably, the cell penetrating peptide comprises or consists of:

a)
$$X_1\text{-KKKIK-}\Psi\text{-EI-}X_2\text{-}X_3$$ (SEQ ID NO: 18)

Wherein $X_1$ is vacant, is a lysine residue, or valine-lysine;
$X_2$ is vacant, is a lysine residue, or lysine-isoleucine;
$X_3$ is vacant or is an amino acid sequence of one to 4 amino acids;
and $\Psi$ is any amino-acid;
or a proteolysis-resistant peptide deriving from SEQ ID NO:18 by one or more chemical modifications, or a substantially homologous peptide, especially peptides deriving from SEQ ID NO:18 by one or more conservative substitutions.

b) $(RQKRLI)_3$ (SEQ ID NO: 19), $(RHSRIG)_3$ (SEQ ID NO: 20), RHSRIGIIQQRRTRNG (SEQ ID NO: 21), RHSRIGVTRQRRARNG (SEQ ID NO: 22), RRRRRRRSRGRRRTY (SEQ ID NO: 23), or homologous peptides;

c) Tat peptide, polyarginines peptide, HA2-$R_9$ peptide, Penetratin peptide (Antenna pedia), Transportan peptide, Vectocell® peptide, maurocalcine peptide, decalysine peptide, HIV-Tat derived PTD4 peptide, Hepatitis B virus Translocation Motif (PTM) peptide, mPrP$_{1-28}$ peptide, POD, pVEC, EB1, Rath, CADY, Histatin 5, Antp peptide, Cyt$^{86-101}$ peptide.

In an embodiment, in the cell penetrating peptide of a), X3 is vacant, i.e. the cell penetrating peptide is X1-KKKIK-$\Psi$-EI-X2 (SEQ ID NO: 24).

In another embodiment, in the cell penetrating peptide of a), X1 is VK, X2 is KI and X3 is vacant, i.e. the cell penetrating peptide is VKKKKIK-$\Psi$-EIKI (SEQ ID NO: 25).

Preferably $\Psi$ is arginine, lysine, asparagine, or alanine.

The cell-penetrating peptide can thus be VKKKKIKREIKI (SEQ ID NO:26), VKKKKIKAEIKI (SEQ ID NO:27), VKKKKIKKEIKI (SEQ ID NO:28) or VKKKKIKNEIKI (SEQ ID NO:29).

By "Tat peptide", it is meant a peptide having the sequence RKKRRQRRR (SEQ ID NO: 30, Tat peptide 2) or YGRKKRRQRRR, (SEQ ID NO: 31).

By "polyarginines peptide", it is meant a peptide consisting of at least 9 arginines. Preferably, a polyarginine peptide is a peptide having the sequence $R_9$ (SEQ ID NO: 32) or $R_{11}$ (SEQ ID NO: 33).

By "HA2-$R_9$ peptide", it is meant a peptide having the sequence GLFEAIEGFIENGWEGMIDGWYG-$R_9$ (SEQ ID NO: 34).

By "Penetratin peptide", it is meant a peptide having the sequence RQIKIWFQNRRMKWKK (SEQ ID NO: 35).

By "Transportan peptide" (also called "Antp peptide"), it is meant a peptide having the sequence GWTLNSAGYL-LGKINLKALAALAKKIL (SEQ ID NO: 36).

By "Vectocell® peptide", it is meant a peptide originating from human heparin binding proteins and/or anti-DNA antibodies.

By "Maurocalcine peptide", it is meant a peptide having the sequence GDCLPHLKLCKENKDCCSKKCKRRGT-NIEKRCR (SEQ ID NO: 37).

By "decalysine peptide", it is meant a peptide having the sequence KKKKKKKKKK ($K_{10}$) (SEQ ID NO: 38).

By "HIV-Tat derived PTD4 peptide", it is meant a peptide having the sequence YARAAARQARA (SEQ ID NO: 39).

By "Hepatitis B virus Translocation Motif (PTM) peptide", it is meant a peptide having the sequence PLSSIF-SRIGDP (SEQ ID NO: 40).

By "mPrP$_{1-28}$ peptide", it is meant a peptide having the sequence MANLGYWLLALFVTMWTDVGLCKKRPKP (SEQ ID NO: 41).

By "POD peptide", it is meant a peptide having the sequence GGG(ARKKAAKA)$_4$ (SEQ ID NO: 42).

By "pVEC peptide", it is meant a peptide having the sequence LLIILRRRRIRKQAHAHSK (SEQ ID NO: 43).

By "EB1 peptide", it is meant a peptide having the sequence LIRLWSHLIHIWFQNRRLKWKKK (SEQ ID NO: 44).

By "Rath peptide", it is meant a peptide having the sequence TPWWRLWTKWHHKRRDLPRKPE (SEQ ID NO: 45).

By "CADY peptide", it is meant a peptide having the sequence GLWRALWRLLRSLWRLLWRA (SEQ ID NO: 46).

By "Histatin 5 peptide", it is meant a peptide having the sequence DSHAKRHHGYKRKFHEKHHSHRGY (SEQ ID NO: 47).

By "Cyt$^{86-101}$ peptide", it is meant a peptide having the sequence KKKEERADLIAYLKKA (SEQ ID NO: 48).

Chimeric Constructs:

The method of the invention advantageously allows for determining the likelihood for a patient affected with a tumor to respond to a treatment with a chimeric peptide including a pro-apoptotic peptide able to disrupt interaction between caspase 9 and PP2A, fused to a cell-penetrating peptide, or a method for monitoring the efficacy of said treatment.

The chimeric peptide induces cell apoptosis, in vitro and/or in vivo.

The chimeric peptide may preferably have a length comprised between 17 to 80 amino acids, preferably between 20 to 70 amino acids, still preferably between 23 to 40 amino acids.

In a preferred embodiment, the chimeric peptide comprises or consists of a sequence selected from the group consisting of

```
                                            (SEQ ID NO: 49)
VKKKKIKREIKI-YVETLDGIFEQWAHSEDL (SEQ ID NO: 50)
VKKKKIKREIKI-YIETLDGILEQWARSEDL (SEQ ID NO: 51)
VKKKKIKAEIKI-YVETLDGIFEQWAHSEDL (SEQ ID NO: 52)
VKKKKIKAEIKI-YIETLDGILEQWARSEDL (SEQ ID NO: 53)
VKKKKIKKEIKI-YVETLDGIFEQWAHSEDL (SEQ ID NO: 54)
VKKKKIKKEIKI-YIETLDGILEQWARSEDL (SEQ ID NO: 55)
VKKKKIKNEIKI-YVETLDGIFEQWAHSEDL (SEQ ID NO: 56)
VKKKKIKNEIKI-YIETLDGILEQWARSEDL (SEQ ID NO: 57)
VKKKKIKREIKI-DTLDHIRALDRLQEVPHEGP (SEQ ID NO: 58)
(RQKRLI)3-DTLDHIRALDRLQEVPHEGP,
```

-continued (RHSRIG)3-DTLDHIRALDRLQEVPHEGP, (SEQ ID NO: 59)

RHSRIGIIQQRRTRNG-DTLDHIRALDRLQEVPHEGP, (SEQ ID NO: 60)

RHSRIGVTRQRRARNG-DTLDHIRALDRLQEVPHEGP, (SEQ ID NO: 61)

RRRRRRSRGRRRTY-DTLDHIRALDRLQEVPHEGP, (SEQ ID NO: 62)

is a proteolysis-resistant peptide deriving from said chimeric peptide by one or more chemical modifications, or a substantially homologous peptide, preferably deriving from the amino acid sequence SEQ ID NO: 49 to 62 by one or more conservative substitutions.

Peptide Preparation:

Peptides described herein have been disclosed in patent applications WO2010/112471 or WO2012/042038, and can be synthesized using standard synthetic methods known to those skilled in the art, for example chemical synthesis or genetic recombination. Alternatively, the peptide may be synthesized using recombinant techniques. In this case, a nucleic acid and/or a genetic construct, comprising or consisting of a nucleotide sequence encoding a peptide according to the invention, polynucleotides with nucleotide sequences complementary to one of the above sequences and sequences hybridizing to said polynucleotides under stringent conditions.

Further Protection Against Proteolysis:

The N- and C-termini of the peptides described herein may be optionally protected against proteolysis. For instance, the N-terminus may be in the form of an acetyl group, and/or the C-terminus may be in the form of an amide group. Internal modifications of the peptides to be resistant to proteolysis are also envisioned, e.g. wherein at least a —CONH— peptide bond is modified and replaced by a (CH2NH) reduced bond, a (NHCO) retro-inverso bond, a (CH2-O) methylene-oxy bond, a (CH2-S) thiomethylene bond, a (CH2CH2) carba bond, a (CO—CH2) cetomethylene bond, a (CHOH—CH2) hydroxyethylene bond), a (N—N) bound, a E-alcene bond or also a —CH=CH-bond.

For instance the peptide may be modified by acetylation, acylation, amidation, cross-linking, cyclization, disulfide bond formation, formation of covalent cross-links, formation of cysteine, formation of pyroglutamate, formylation, gamma-carboxylation, glycosylation, GPI anchor formation, hydroxylation, iodination, methylation, myristylation, oxidation, phosphorylation, and the like.

The peptides may be composed of amino acid(s) in D configuration, which render the peptides resistant to proteolysis. They may also be stabilized by intramolecular crosslinking, e.g. by modifying at least two amino acid residues with olefinic side chains, preferably C3-C8 alkenyl chains, preferably penten-2-yl chains) followed by chemical crosslinking of the chains, according to the so-called "staple" technology. For instance, amino acids at position i and i+4 to i+7 can be substituted by non-natural aminoacids that show reactive olefinic residues. All these proteolysis-resistant chemically-modified peptides are encompassed in the present invention.

In another aspect of the invention, peptides are covalently bound to a polyethylene glycol (PEG) molecule by their C-terminal terminus or a lysine residue, notably a PEG of 1500 or 4000 MW, for a decrease in urinary clearance and in therapeutic doses used and for an increase of the half-life in blood plasma. In yet another embodiment, peptide half-life is increased by including the peptide in a biodegradable and biocompatible polymer material for drug delivery system forming microspheres. Polymers and copolymers are, for instance, poly(D,L-lactide-co-glycolide) (PLGA) (as illustrated in US2007/0184015).

Treatment:

The pro-apoptotic or chimeric peptides as defined herein, can be used alone or in combination with an anti-tumor agent, preferably a chemotherapeutic agent, for simultaneous administration (i.e., at the same time, as a single composition or separate compositions), or sequential administration.

The peptides, generally formulated in association with a pharmaceutically acceptable carrier, may be administered by any convenient route including intravenous, oral, transdermal, subcutaneous, mucosal, intramuscular, intrapulmonary, intranasal, parenteral, rectal, vaginal and topical. Intranasal route is of particular interest. Advantageously, intra-tumoral administration is also contemplated.

The dosing is selected by the skilled person so that a pro-apoptotic effect is achieved, and depends on the route of administration and the dosage form that is used. Total daily dose administered to a subject in single or divided doses may be in amounts, for example, of from about 0.001 to about 100 mg/kg body weight daily and preferably 0.01 to 10 mg/kg/day. A daily dosage of about 5 mg/kg is preferred. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

Further aspects and advantages of the present invention will be disclosed in the following experimental section, which should be regarded as illustrative and not limiting the scope of the present application.

Example 1

Identification of Predictive Markers of Response by RT-qPCR

Materials and Methods

1. Mice Models

Breast-cancer patient xenografts (PDXs) were obtained by direct implant of patient tumor fragments in immunocompromised mice. (Arrouss Et al, PlosOne. 2013. 8, e60816).

Melanoma patient xenografts were obtained as described in Laurent C, et al. Mol Oncol 203; 7:625-36 and Nemati F, et al. Clinical Cancer Res 2010; 16:2352-2362.

The chimeric peptide is VKKKKIKREIKI-YVETLDG-IFEQWAHSEDL (SEQ ID NO: 49), also designated DPT-C9h.

Nine models treated by DPT-C9h (5 mg/kg/d IP, 5 days weekly, 4 to 6 weeks) were selected for the study, i.e. 7 breast cancer PDXs (BC11, BC52, BC143, BC146, BC173, BC227, and BC256), and 2 ovarian cancer PDXs (OV14 and OVM33). Three tumors of both control and treated groups were collected at the end of therapy, except for the BC146 for which 2 control tumors and 3 treated tumors were obtained. For each collected tumor, tumor volume was estimated according to the following formulae: $V = a \times b2/2$, where a and b are the largest and the smallest perpendicular tumor diameters.

Hence, in a first time, for each included tumor, a Tumor Growth Rate (TGR) was calculated using the following formula: TGR=(Vf/V1), where Vf is the tumor volume at the end of therapy and V1 the tumor volume at initiation of therapy (day 1). In a second time, a median TGR was defined for the control and treated groups of each PDX model. Finally, a ratio was calculated for each PDX model, as: median TGR of the treated group/median TGR of the corresponding control group. The inventors considered that a model was responder to DPT-C9h if the ratio was ≤0.5 (p<0.05), and resistant if the ratio was ≥0.8. In this, 3 models were considered as responder (BC52, BC173 and OV14), 4 as resistant (BC11, BC146, BC227, and BC256), and 2 remained undefined and were excluded from analyses (BC143 and OVM33) (Table 1).

TABLE 1

Mean TGR in control and treated groups of the 9 included PDXs

|  | BC52 | BC227 | OVM33 | BC143 | BC173 | BC146 | OV14 | BC11 | BC256 |
| --- | --- | --- | --- | --- | --- | --- | --- | --- | --- |
| Mean TGR DPT | 15.3 | 6.0 | 35.0 | 27.7 | 6.0 | 34.7 | 10.7 | 24.3 | 38.7 |
| Mean TGR CTRL | 40.0 | 4.3 | 54.0 | 40.7 | 13.3 | 36.0 | 24.3 | 27.0 | 31.3 |
| Ratio TGR | 0.38 | 1.38 | 0.65 | 0.68 | 0.45 | 0.96 | 0.44 | 0.90 | 1.23 |
| Ttest value | 0.027 | 0.279 | 0.492 | 0.131 | 0.038 | 0.842 | 0.041 | 0.730 | 0.418 |
| conclusion | + | − | ND | ND | + | − | + | − | − |

+: responder;
−: resistant;
ND: unidentified

2. RT-qPCR Study

Total RNA was isolated from cell sorting fractions using the RNeasy Plus Micro kit (Qiagen, Inc.). The RNA quality was assessed by capillary electrophoresis (Bioanalyzer, Agilent, Inc.) based on RNA 6000 Pico LabChip kits that assign per sample quantification and integrity.

The expression of 31 human genes has been studied, in which orthologous mouse and Human gene expressions could be available, namely:

Proliferation: MKI67, PLK1, AURKA, BBC3 (PUMA), NEK2, NDC80, AURKB, TPX2.
Apoptosis: BCL2, BCL-$X_L$, p21/CDKN1A, TRAF2, MCL1, BIRC5 (Survivin), CASP9, BIRC2/IAP1, BIRC3/IAP2, BIRC4/XIAP, GADD45B, BCL2A1, LEF1, TCF7L2/TCF4.
Wt: TCF7L2/TCF4.
Migration/Invasion: MMP9 HS.
EMT: VIM, CDH1.
Vascularisation: VEGFA HS.
NF$_K$B: TNFAIP3, RELB.
Immunity/Inflammation: IL8, SELE, VCAM, CSF2, PTGS2/COX2, TNF, CCL2, CCL8.
Stem cell: CD133.
Metabolism: SLC2A1 (GLUT1).

Controls were defined as RT-qPCR value of both human and mouse TBP (TATA box binding protein).

3. Bioinformatics Analyses

Bioinformatics analyses of RT-qPCR data included unsupervised clustering, correlation with TGR, analysis of differentially expressed genes, and definition of a minimum gene signature.

Results

1. Unsupervised Clustering:

Unsupervised clustering showed that all tumors originated from the same model, except one BC11 tumor, clustered together. Moreover, the 4 resistant PDXs clustered together, suggesting that a specific gene expression profile could be related to the in vivo efficacy of DPT-C9h.

2. Differentially Expressed Genes:

Analysis of differentially expressed genes (Fold-Change ≥1.5 and p-value ≤0.01) between responding and resistant tumors was presented in the Table 2.

TABLE 2

Significantly differentially expressed genes°

| Gene symbol | Regulation | Fold-Change | p-value |
| --- | --- | --- | --- |
| VIM | Down | 121 | $2.7 \cdot 10^{-4}$ |
| VCAM | Down | 8 | $1 \cdot 10^{-2}$ |

TABLE 2-continued

Significantly differentially expressed genes°

| Gene symbol | Regulation | Fold-Change | p-value |
| --- | --- | --- | --- |
| TCF7L2 | Down | 3.32 | $1.3 \cdot 10^{-9}$ |
| NEK2 | Down | 3.26 | $8.15 \cdot 10^{-6}$ |
| MKI67 | Down | 3.24 | $2.03 \cdot 10^{-4}$ |
| VEGFA | Down | 3.03 | $8.85 \cdot 10^{-3}$ |
| GADD45B | Down | 2.85 | $7.66 \cdot 10^{-3}$ |
| BIRC5 | Down | 2.68 | $4.92 \cdot 10^{-4}$ |
| PLK1 | Down | 2.48 | $3.17 \cdot 10^{-3}$ |
| TNFAIP3 | Down | 2.29 | $6.53 \cdot 10^{-3}$ |
| MCL1 | Down | 1.86 | $1.76 \cdot 10^{-3}$ |
| BBC3 | Down | 1.8 | $1.04 \cdot 10^{-3}$ |

°All genes are down-regulated.

3. Minimum Gene Signature:

3.1. Score Definition and Sample Classification:

Finally, predictive signature was defined using PAM (Tibshirani et al., PNAS 2002, 99(10):6567-6572). "Prediction Analysis of Microarrays" (PAM) performs sample classification from gene expression data using the nearest shrunken centroid method. PAM provides a list of significant genes whose expression characterizes each sample group. The software was developed at Stanford University.

S scores were defined using RT-qPCR gene expression values from 7 untreated models known to be resistant or responder (responder models: BC52, BC173 and OV14; resistant models: BC227, BC146, BC11 and BC256).

Responder score and resistant score were defined according to the following formulas:

$$S_{Responder} = \sum_{i=1}^{7} \left(\frac{Exp_i - Mean_{i\ Responder}}{StdDev_{i\ Responder}}\right)^2 \alpha_{i\ Responder}$$

$$S_{Resistant} = \sum_{i=1}^{7} \left(\frac{Exp_i - Mean_{i\ Resistant}}{StdDev_{i\ Resistant}}\right)^2 \alpha_{i\ Resistant}$$

$Exp_i$: RT-qPCR expression value of $gene_i$ $Mean_{i\ Responder}$: Mean expression of gene, defined in table "Responder values" in Table 3.

$StdDev_{i\ Responder}$: Standard deviation of expression of gene, defined in table "Responder values" in Table 3.

$\alpha_{i\ Responder}$: Weight factor of $gene_i$ defined in table "Responder values" in Table 4 (from PAM signature)

$Mean_{i\ Resistant}$: Mean expression of $gene_i$ defined in table "Resistant values" in Table 3.

$StdDev_{i\ Resistant}$: Standard deviation of expression of $gene_i$ defined in table "Resistant values" in Table 3.

$\alpha_{i\ Resistant}$: Weight factor of $gene_i$ defined in table "Resistant values" in Table 3 (from PAM signature)

Score interpretation:

Sample is considered as responder if $S_{Responder} < 2$ and $S_{Resistant} > 5$.

Sample is considered as resistant if $S_{Responder} > 50$ and $S_{Resistant} < 2$.

Sample is considered as undefined otherwise.

TABLE 3

| Responder and Resistant reference values | | | | |
|---|---|---|---|---|
| Gene Symbol | i | Mean | StdDev | α |
| Responder values: | | | | |
| VIM | 1 | 914.322 | 1739.860 | 0.543 |
| MKI67 | 2 | 1380.054 | 803.760 | 0.130 |
| TCF7L2 | 3 | 318.665 | 64.459 | 0.095 |
| NEK2 | 4 | 396.319 | 192.776 | 0.084 |
| BIRC5 | 5 | 762.647 | 503.070 | 0.075 |
| MCL1 | 6 | 2578.211 | 691.032 | 0.059 |
| PLK1 | 7 | 446.161 | 161.070 | 0.014 |
| Resistant values: | | | | |
| VIM | 1 | 26149.972 | 8805.582 | 0.543 |
| MKI67 | 2 | 4559.266 | 2191.937 | 0.130 |
| TCF7L2 | 3 | 1105.052 | 290.120 | 0.095 |
| NEK2 | 4 | 1319.659 | 447.542 | 0.084 |
| BIRC5 | 5 | 1709.735 | 416.526 | 0.075 |

TABLE 3-continued

| Responder and Resistant reference values | | | | |
|---|---|---|---|---|
| Gene Symbol | i | Mean | StdDev | α |
| MCL1 | 6 | 4791.188 | 1892.428 | 0.059 |
| PLK1 | 7 | 1185.272 | 494.268 | 0.014 |

3.2. Definition of the Signature:

Hence, the inventors defined a minimum 7 gene signature between responder and resistant samples (VIM, MKI67, TCF7L2, NEK2, BIRC5, MCL1, and VEGFA) (Table 4).

TABLE 4

| Minimum gene signature | | |
|---|---|---|
| Gene symbol | PAM value (responder) | PAM value (resistant) |
| VIM | −1.5966 | 1.1611 |
| MKI67 | −0.3823 | 0.278 |
| TCF7L2 | −0.281 | 0.2043 |
| NEK2 | −0.2474 | 0.1799 |
| BIRC5 | −0.2214 | 0.161 |
| MCL1 | −0.1731 | 0.1259 |
| PLK1 | −0.0407 | 0.0296 |

4. Validation of the Defined Minimum Gene Signature:

The previously defined gene signature was then confirmed using all control tumors of the seven PDXs models included in the analysis. The inventors clearly discriminates two groups (responder and resistant) without misclassified sample.

Example 2

Applicability of the defined minimum gene signature

The gene signature identified in Example 1 was then addressed in various tumor populations, i.e. the panel of breast cancer PDXs developed in the laboratory of preclinical investigation (LIP) of the Institut Curie, a population of breast cancer patients (de Cremoux, 2011, BMC Cancer, 11, pp. 215), the panel of uveal melanoma PDXs developed in the LIP, and the panel of ovarian cancer PDXs developed in the LIP. In all cases, the inventors observed that gene signature discriminated two different groups, one being supposed as "responder" to DPT-C9h and the other one supposed as "resistant".

The invention claimed is:

1. A method for treating a tumor in a patient, which method comprises
   a) determining expression level of at least each of VIM, MK167, TCF7L2, NEK2, BIRC5, MCL1, and PLK1 genes, in a biological sample of a patient with a tumor, wherein a decreased expression of said genes compared to control values for said genes is indicative of a patient being likely to respond to a treatment with a chimeric peptide comprising i) a pro-apoptotic peptide that comprises SEQ ID NO: 4 or SEQ ID NO: 1 fused at the C-terminus to ii) a cell-penetrating peptide that comprises a sequence selected from the group consisting of SEQ ID NO: 26, 27, 28 and 29; and
   b) administering said chimeric peptide to a patient having decreased expression of at least each of VIM, MK167, TCF7L2, NEK2, BIRC5, MCL1, and PLK1 genes compared to control values for said genes.

2. The method of claim 1, wherein the pro-apoptotic peptide is SEQ ID NO: 4 and the cell-penetrating peptide is SEQ ID NO: 26 or SEQ ID NO: 27.

3. The method of claim 1, wherein the tumor is a cancer selected from the group consisting of a breast tumor, an ovarian tumor, a lung tumor, a colon tumor and a prostate tumor, or is a tumor selected from the group consisting of acute myelogenous leukaemia, chronic lymphocytic leukaemia, multiple myeloma, Hodgkin's disease, non-Hodgkin's lymphoma, B cell, cutaneous T cell lymphoma, brain, head and neck, bladder, gastric, pancreatic, head, neck, renal, prostate, colorectal, oesophageal, thyroid cancer, uveal melanoma and melanoma.

4. The method of claim 1, wherein the expression levels of said genes is determined by RT-PCR amplification.

* * * * *